(12) United States Patent
Saaski et al.

(10) Patent No.: US 7,651,869 B2
(45) Date of Patent: Jan. 26, 2010

(54) OPTICAL ASSAY APPARATUS AND METHODS

(75) Inventors: Elric W. Saaski, Bothell, WA (US); David A. McCrae, Richmond, CA (US)

(73) Assignee: Research International, Inc., Monroe, WA (US)

( * ) Notice: Subject to any disclaimer, the term of this patent is extended or adjusted under 35 U.S.C. 154(b) by 351 days.

(21) Appl. No.: 11/374,934

(22) Filed: Mar. 14, 2006

(65) Prior Publication Data
US 2009/0296083 A1    Dec. 3, 2009

(51) Int. Cl.
*G01N 33/543* (2006.01)
(52) U.S. Cl. .................. 436/518; 385/12; 356/246; 422/58; 422/82.05; 422/82.11; 435/288.7; 435/808; 436/164; 436/165; 436/524; 436/527; 436/805
(58) Field of Classification Search .............. None
See application file for complete search history.

(56) References Cited

U.S. PATENT DOCUMENTS

| | | |
|---|---|---|
| 3,604,927 A | 9/1971 | Hirschfeld |
| 4,050,895 A | 9/1977 | Hardy et al. |
| 4,133,639 A | 1/1979 | Harte |
| 4,244,694 A | 1/1981 | Farina et al. |
| 4,257,671 A | 3/1981 | Barbaudy et al. |
| 4,321,057 A | 3/1982 | Buckles |
| 4,399,099 A | 8/1983 | Buckles |
| 4,447,546 A | 5/1984 | Hirschfeld |
| 4,477,578 A | 10/1984 | Miles et al. |
| 4,558,014 A | 12/1985 | Hirschfeld et al. |
| 4,582,809 A | 4/1986 | Block et al. |
| 4,595,833 A | 6/1986 | Sting |
| 4,639,242 A | 1/1987 | Babson |
| 4,654,532 A | 3/1987 | Hirschfeld |

(Continued)

FOREIGN PATENT DOCUMENTS

EP    0 128 723 A2    12/1984

(Continued)

OTHER PUBLICATIONS

Li Li, C. et al., "Application of Electromodulated Fluorescence To The . . .", Langmuir 2000, vol. 16, No. 10, pp. 4672-4677, American Chemical Society, U.S., 2000.

(Continued)

*Primary Examiner*—Christopher L Chin
(74) *Attorney, Agent, or Firm*—Gregory W. Moravan

(57) ABSTRACT

Optical assay apparatus and methods are provided having an optical assay cup for detecting analytes in a sample fluid. The cup's sidewall may include an optical waveguide having a detection coating on its inner surface. During use, the waveguide receives evanescent or darkfield interrogation light, interrogates at least part of cup's interior volume with it, and emits signal light as a function of the analytes. The detection coating may have fluid or non-fluid detection layers, at least part of which may form at least part of a waveguide for the interrogation light. The cup may be spun during use, such as to centrifugally-concentrate any high-density analytes towards cup's sidewall. The assay apparatus may further include an interrogation light source, a cover or spinning apparatus for the cup, and an optical detector for the signal light.

51 Claims, 19 Drawing Sheets

U.S. PATENT DOCUMENTS

| | | | |
|---|---|---|---|
| 4,671,938 A | 6/1987 | Cook | |
| 4,716,121 A | 12/1987 | Block et al. | |
| 4,844,869 A | 7/1989 | Glass | |
| 4,852,967 A | 8/1989 | Cook et al. | |
| 4,909,990 A | 3/1990 | Block et al. | |
| 4,979,821 A * | 12/1990 | Schutt et al. | 356/246 |
| 5,055,408 A | 10/1991 | Higo et al. | |
| 5,061,857 A | 10/1991 | Thompson et al. | |
| 5,084,240 A | 1/1992 | Babson | |
| 5,093,569 A | 3/1992 | Krumboltz et al. | |
| 5,098,845 A | 3/1992 | Babson | |
| 5,111,221 A | 5/1992 | Fare et al. | |
| 5,149,501 A | 9/1992 | Babson et al. | |
| 5,152,962 A | 10/1992 | Lackie | |
| 5,156,976 A | 10/1992 | Slovacek et al. | |
| 5,164,318 A | 11/1992 | Sato et al. | |
| 5,171,533 A | 12/1992 | Fine et al. | |
| 5,225,374 A | 7/1993 | Fare et al. | |
| 5,242,797 A | 9/1993 | Hirschfeld | |
| 5,244,635 A | 9/1993 | Rabson et al. | |
| 5,249,077 A | 9/1993 | Laronga et al. | |
| 5,258,309 A | 11/1993 | Babson et al. | |
| 5,268,486 A | 12/1993 | Waggoner et al. | |
| 5,290,398 A | 3/1994 | Feldman et al. | |
| 5,310,523 A | 5/1994 | Smethers et al. | |
| 5,318,748 A | 6/1994 | Babson et al. | |
| 5,340,715 A | 8/1994 | Slovacek et al. | |
| 5,359,681 A | 10/1994 | Jorgenson et al. | |
| 5,399,866 A | 3/1995 | Feldman et al. | |
| 5,428,690 A | 6/1995 | Bacus et al. | |
| 5,430,813 A | 7/1995 | Anderson et al. | |
| 5,442,448 A | 8/1995 | Knoll | |
| 5,468,606 A | 11/1995 | Bogart et al. | |
| 5,492,674 A | 2/1996 | Meserol | |
| 5,494,793 A | 2/1996 | Schindele et al. | |
| 5,512,492 A | 4/1996 | Herron et al. | |
| 5,525,466 A | 6/1996 | Slovacek et al. | |
| 5,538,691 A * | 7/1996 | Tosa et al. | 422/102 |
| 5,545,517 A | 8/1996 | Thompson et al. | |
| 5,569,766 A | 10/1996 | Waggoner et al. | |
| 5,580,790 A | 12/1996 | Wall et al. | |
| 5,582,796 A | 12/1996 | Carey et al. | |
| 5,606,170 A | 2/1997 | Saaski et al. | |
| 5,627,041 A | 5/1997 | Shartle | |
| 5,719,063 A | 2/1998 | Block | |
| 5,723,092 A | 3/1998 | Babson | |
| 5,858,800 A | 1/1999 | Shigemori et al. | |
| 5,885,529 A | 3/1999 | Babson et al. | |
| 5,910,288 A | 6/1999 | Schembri | |
| 5,912,134 A | 6/1999 | Shartle | |
| 5,955,377 A | 9/1999 | Maul et al. | |
| 5,989,913 A | 11/1999 | Anderson et al. | |
| 6,001,556 A | 12/1999 | Charych et al. | |
| 6,007,996 A | 12/1999 | McNamara et al. | |
| 6,008,057 A | 12/1999 | Glass et al. | |
| 6,063,589 A | 5/2000 | Kellogg et al. | |
| 6,080,581 A | 6/2000 | Anderson et al. | |
| 6,082,185 A | 7/2000 | Saaski | |
| 6,110,749 A | 8/2000 | Obremski et al. | |
| 6,136,611 A | 10/2000 | Saaski et al. | |
| 6,143,247 A | 11/2000 | Sheppard, Jr. et al. | |
| 6,143,248 A | 11/2000 | Kellogg et al. | |
| 6,192,168 B1 | 2/2001 | Feldstein et al. | |
| 6,259,557 B1 | 7/2001 | Miyashita et al. | |
| 6,302,134 B1 | 10/2001 | Kellogg et al. | |
| 6,312,886 B1 | 11/2001 | Lee et al. | |
| 6,319,468 B1 | 11/2001 | Sheppard, Jr. et al. | |
| 6,319,469 B1 | 11/2001 | Mian et al. | |
| 6,342,349 B1 | 1/2002 | Virtanen | |
| 6,399,361 B2 | 6/2002 | Brotherston et al. | |
| 6,449,088 B1 | 9/2002 | Pettingell et al. | |
| 6,527,432 B2 | 3/2003 | Kellogg et al. | |
| 6,548,788 B2 | 4/2003 | Kellogg et al. | |
| 6,565,813 B1 | 5/2003 | Garyantes | |
| 6,582,662 B1 | 6/2003 | Kellogg et al. | |
| 6,597,522 B2 | 7/2003 | Freber | |
| 6,632,399 B1 | 10/2003 | Kellogg et al. | |
| 6,656,430 B2 | 12/2003 | Sheppard, Jr. et al. | |
| 6,704,140 B1 | 3/2004 | Richardson | |
| 6,706,519 B1 | 3/2004 | Kellogg et al. | |
| 6,709,869 B2 | 3/2004 | Mian et al. | |
| 6,719,682 B2 | 4/2004 | Willis et al. | |
| 6,809,862 B2 | 10/2004 | Behnsen et al. | |
| 6,816,249 B2 | 11/2004 | Fairley et al. | |
| 6,818,435 B2 | 11/2004 | Carvalho et al. | |
| 6,833,916 B2 | 12/2004 | Osipchuk et al. | |
| 6,884,395 B2 | 4/2005 | Tooke et al. | |
| 6,888,627 B2 | 5/2005 | Leslie et al. | |
| 6,933,109 B2 | 8/2005 | Anderson | |
| 6,953,550 B2 | 10/2005 | Sheppard, Jr. et al. | |
| 6,967,101 B1 | 11/2005 | Larsson et al. | |
| 6,992,819 B2 | 1/2006 | Vodyanoy | |
| 6,998,596 B2 | 2/2006 | Fein et al. | |
| 7,002,677 B2 | 2/2006 | Bevis et al. | |
| 7,033,747 B2 | 4/2006 | Gordon | |
| 7,035,001 B2 | 4/2006 | Chuang et al. | |
| 2005/0260677 A1 | 11/2005 | Saaski | |
| 2006/0039643 A1 | 2/2006 | Saaski | |

FOREIGN PATENT DOCUMENTS

| | | |
|---|---|---|
| EP | 0 535 690 A1 | 4/1993 |
| JP | H02-191674 | 7/1990 |
| JP | 03-072263 | 3/1991 |
| JP | H03-272466 | 12/1991 |
| JP | H04-225144 | 8/1992 |
| JP | H05-203574 | 8/1993 |
| JP | H06-308031 | 11/1994 |
| JP | H07-063756 | 3/1995 |
| JP | H07-174692 | 7/1995 |
| JP | H07-181132 | 7/1995 |
| JP | H07-318481 | 12/1995 |
| JP | 08-029330 | 2/1996 |
| JP | S63-273042 | 11/1998 |
| JP | 2004-205268 | 7/2004 |
| WO | WO 84/00817 | 3/1984 |
| WO | WO 90 09574 | 8/1990 |
| WO | WO 92/08966 | 5/1992 |
| WO | WO 9531711 | 12/1995 |
| WO | WO 02/063349 A2 | 8/2002 |

OTHER PUBLICATIONS

Anderson, George P. et al., "A Fiber Optic Biosensor: Combination Tapered Fibers Designed For Improved Signal . . . ", Bio-Sensors & Bioelectronics 8:249-256, 1993.

Anis, N.A., et al., "A Fiber-Optic Immunosensor For Detecting Parathion", Analytical Letters 25(4):627-635, 1992.

Gao, Harry H. et al., "Tapered Fiber Tips For Fiber Optic Biosensors", Optical Engineering 34(12):3465-3470, 1995.

Glass, Thomas R., et al, "Effect Of Numerical Aperture On Signal Level In Cylindrical Waveguide Evanescent Fluorosensors", Applied Optics 26(11):2181-2187, 1987.

Golden, Joel P. et al., "Fluorometer And Tapered Fiber optic Probes For Sensing In The Evanscent Wave", Optical Engineering 31(7):1458-1462, 1992.

Golden, Joel P. et al., "Portable Multichannel Fiber Optic Biosensor For Field Detection", 1997 Optical Engineering 36(4), 1008-1013, Apr. 1997.

Golden, Joel P. et al., "Ray Tracing Determination Of Evanescent Wave Penetration Depth . . . ", Chemical, Biochemical, and Environmental Fiber Sensors IV 1796:9-13, 1992.

Hale, Z.M., et al., "Fluorescent Sensors Based On Tapered Single-Mode Optical Fibers", Sensors And Actuators B. 17:233-240, 1994.

Hobbs, J.R., "Fluorescence Reveals Toxins On Antibody-Coated Fiberoptic Probe", Laser Focus World 28(5):83-86, 1992.

Huber, W., et al., "Direct Optical Immunosensing (Sensitivity And Selectivity)", Sensors And Actuators B. 6:122-126, 1992.

Jorgenson, R.C., et al., "A Fiber-Optic Chemical Sensor Based On Surface Plasmon Resonance", Sensors And Actuators B. 12, (3):213-220, 1993.

Jung, C.C., et al., "Chemical Electrode Surface Plasmon Resonance Sensor", Sensors And Actuators B. 32(2):143-147, 1996.

Ligler, F.S., et al., "Evanescent Wave Fiber Optic Biosensor", Proc. Biosensors, A.P.F. Turner, ed., pp. 308-315, 1992.

Rogers, Kim R., et al., "Acetylcholine Receptor Fiber-Optic Evanescent Fluorosensor", Analytical Biochemistry 182:353-359, 1989.

Wong, R.B., et al., "Reusable Fiber-Optic-Based Immunosensor For Rapid Detection Of Imazethapyr Herbicide", Analytica Chimica Acta, 279:141-147, 1993.

Saaski, Elric W., "Research International, A Universe Of Solutions"; shown, but not published, on Aug. 27, 2002, 62 pages, Tokyo, Japan.

Jung, Chuck C., et al., "RAPTOR: A Fluoroimmunoassay-Based Fiber Optic Sensor For Detection Of Biological Threats", IEEE Sensors Journal, vol. 3, No. 4, Aug. 2003, pp. 352-360, USA.

International Search Report, 2 pages, dated Sep. 4, 2008 regarding PCT/US 07/05691.

Written Opinion of International Searching Authority, 7 pages, dated Sep. 4, 2008 regarding PCT/US 07/05691.

Official Letter From Japanese Patent Office mailed Oct. 2, 2007 Regarding Corresponding Japanese Patent Application No. 2007-065910, 3 pages.

* cited by examiner

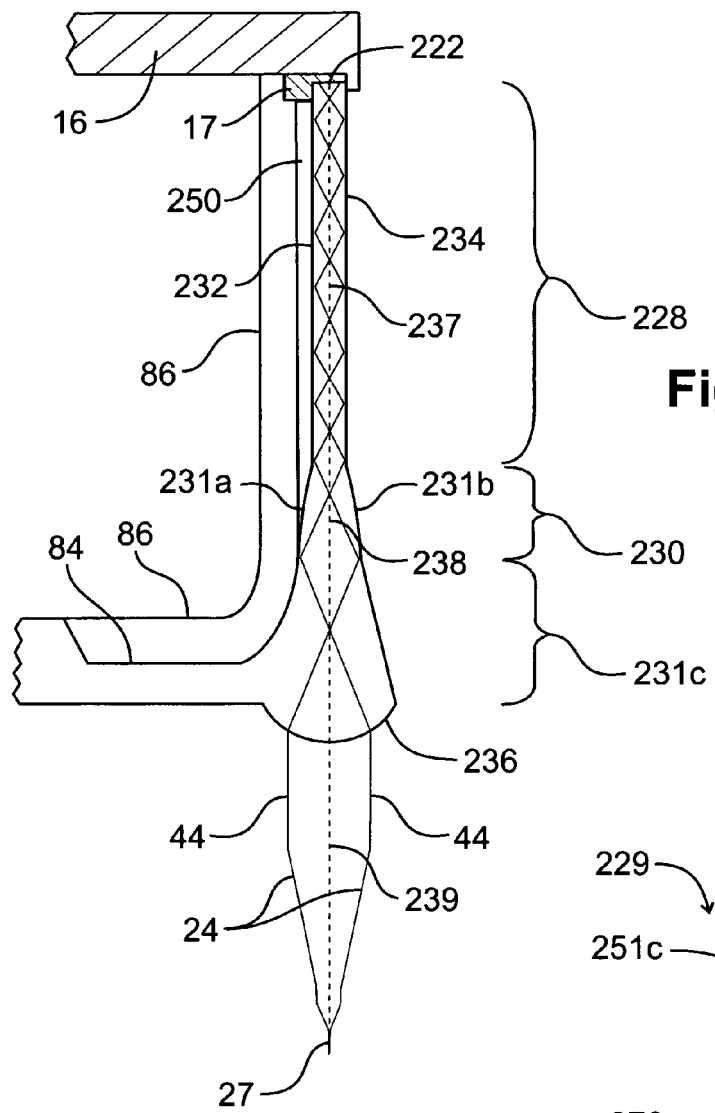
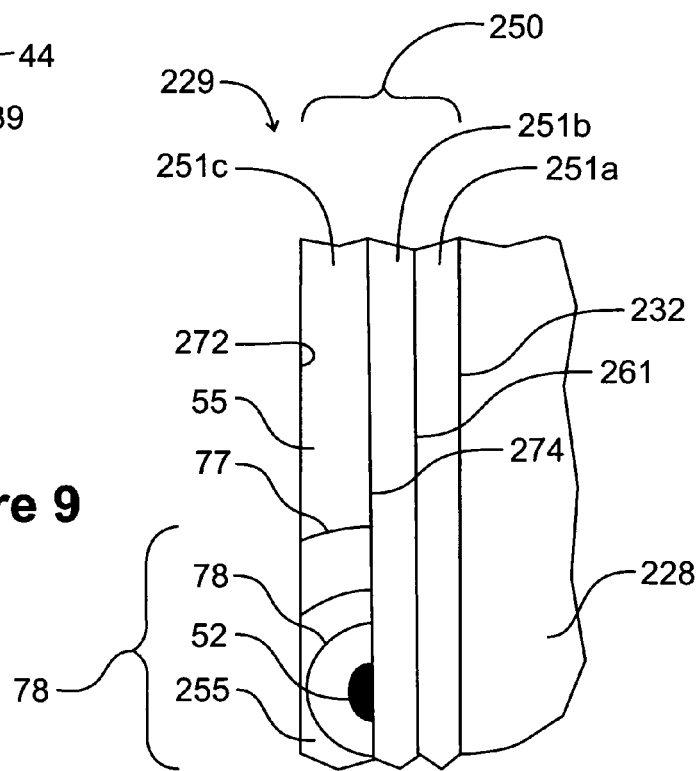
Figure 8
Figure 9

OPTICAL ASSAY APPARATUS AND METHODS

BACKGROUND OF THE INVENTION

This invention relates generally to apparatus and methods for chemical and biochemical detection and assays, and more particularly it relates to optics-based apparatus and methods for such detection and assays.

BRIEF SUMMARY OF THE INVENTION

There exists a need for a highly sensitive and specific technology directed to chemical and biochemical detection and assays, such as where the analytes are, for example, human pathogens or toxins in food, water, or the environment.

As used herein, an "analyte" is defined to be anything that may be present in the sample fluid that is of interest to the user of the present invention, and that is detectable by the present invention. Unless the context should clearly indicate otherwise, the term "analytes" means more than one kind of analyte may be present in the sample fluid, such as where two, or more, different kinds of analytes may be present in the sample fluid; and it also means that more than one of a particular kind of analyte may be present in the sample fluid, such as where the analyte is a bacterium, and there are two, or more, individuals of that particular kind of bacterium in the sample fluid.

The optical assay apparatus and methods of the present invention are adapted to detect at least one particular kind of analyte that may be present in a sample fluid. In addition, the present invention may also be adapted to be so sensitive that it may detect in the sample fluid even a single one of a particular kind of analyte, such as single bacterium or spore. In either event, such detection may include, for example, detecting the presence, quantity, number, or at least one targeted distinguishing characteristic of the analytes.

In basic form, the optical assay apparatus of the present invention may include an optical assay cup. The assay apparatus may further include a light source that produces an output of light source interrogation light, an optical detector, and a cover for the cup.

The cup may have a light conveying sidewall and an interior volume at least partially defined by the sidewall. The sidewall may have an optical waveguide portion and a reflector portion. Hereinafter, for simplicity, the optical waveguide portion of the cup's sidewall will be referred to as the waveguide, and the reflector portion of the cup's sidewall will be referred to as the reflector.

The cup's interior volume may include a detection coating for the analytes. The detection coating may be located on the waveguide's inner surface and may include at least one fluid or non-fluid detection layer.

During use, the sample fluid may be added to the cup and the waveguide may receive an input of waveguide interrogation light, which may be evanescent interrogation light or darkfield interrogation light. The waveguide interrogation light may be used to interrogate at least a part of the cup's interior volume. At least part of the detection coating, and any of its fluid or non-fluid detection layers, may form at least a portion of an optical waveguide for at least part of the waveguide interrogation light.

The waveguide interrogation light may be received directly from the light source, in which case the waveguide interrogation light may comprise at least part of the output of light source interrogation light.

Alternatively, the waveguide interrogation light may be received indirectly from the light source, such as where the cup's sidewall includes a reflector that receives an input of reflector interrogation light from the light source, and produces in response thereto an output of reflector interrogation light. In such a case, the input of reflector interrogation light may comprise at least part of the output of light source interrogation light, and the waveguide interrogation light may comprise at least part of the output of reflector interrogation light.

In either case, in response to interrogation of at least a part of the cup's interior volume by the waveguide interrogation light, the waveguide's outer surface may then emit an output of signal light from signal-generating processes occurring on or near the waveguide's inner surface, with these signal-generating processes being a function of any analytes that may be present in the sample fluid. Such signal light may be emitted as a function of, for example, the presence, quantity, number, or at least one targeted distinguishing characteristic of the analytes.

Alternatively, interrogation light may not be required for optical detection of the analytes. For example, in a luminescence optical detection method, reagents may be added to the cup that trigger luminescence when the targeted analytes are present in the sample fluid. The waveguide's outer surface may then emit an output of signal light as a function of any analytes that may be present in the sample fluid. Such signal light may be emitted as a function of, for example, the presence, quantity, number, or at least one targeted distinguishing characteristic of the analytes. As another alternative, a combination of interrogation light and luminescence detection methods may be used. This may provide, for example, greater assurance of accurate test results, or provide the ability to monitor different kinds of analytes at the same time.

In all cases the optical detector may receive at least part of the signal light from the waveguide's outer surface, and produce electrical output signals as a function of the signal light that it receives.

Generation of signal light (and the resulting electrical output signals), may be based on interrogation of at least a part of the cup's interior volume by evanescent interrogation or darkfield interrogation. In evanescent interrogation, rays of evanescent interrogation light traveling within the waveguide are reflected back into the waveguide at the waveguide's surfaces, but generate induced evanescent electric fields outside the waveguide that decay exponentially with distance from the waveguide's surfaces. These evanescent electric fields may be useful in determining the presence of analytes by interrogating or stimulating optically active substances such as dyes that are present on or near the waveguide's inner surface.

Darkfield interrogation as taught herein is superficially similar to darkfield microscopy, but is designed specifically for waveguide-based sensing of analytes. In darkfield microscopy, the analytes are illuminated obliquely so that light does not directly enter the microscope objective; rather, the majority of light entering the microscope has been reflected, refracted or scattered into the objective lens by optical discontinuities and irregularities associated with the analytes. In darkfield interrogation, rays of darkfield interrogation light are prevented from directly entering the optical detector by waveguide surface reflections similar to those that occur in evanescent interrogation. However, in this case the analytes are directly excited by the darkfield interrogation light's electric fields, instead of by induced evanescent electric fields.

Which mode of interrogation or combinations thereof are used may be determined in any suitable way such as, for example, by suitably adjusting the angles that the rays of waveguide interrogation light make with respect to the selected interface. This may be done in any suitable way, such as by providing the cup's sidewall with a reflector that may receive an input of reflector interrogation light from the light source, and which may then produce an output of reflector interrogation light that enters the waveguide at a desired angle, or at a desired range of angles, with respect to the waveguide's inner surface or optical surface of symmetry.

Alternatively, or in addition, which or both modes of interrogation are used may be determined, by way of further example, by suitably positioning the light source at a desired angle, or at a desired range of angles, with respect to the waveguide or the reflector, or with respect to their respective optical surfaces of symmetry.

The relatively large surface area of the inner surface of the detection coating, or of the waveguide (if there is no detection coating), may desirably enhance the speed, sensitivity, or accuracy of any measurements taken by the present invention of the analytes in the cup, as compared to conventional optical assay devices, such as those employing a fiber optic sensing element, which may have a comparatively much smaller sensing surface area.

During use of the optical assay apparatus of the present invention, the cup may be spun on its axis by any suitable spinning apparatus, which may comprise part of the optical assay apparatus.

Such spinning of the cup on its axis may serve one or more of several purposes. In the following discussion, it will be assumed by way of example that the fluid in the cup is the sample fluid, it being understood that similar comments may apply equally well regarding any other fluid in the cup, such as a reagent fluid, a wash fluid, or water, for example.

One of the purposes served by spinning the cup may be, for example, to exert a centrifugal force on the sample fluid in the cup in order to centrifugally concentrate any high-density analytes in the sample fluid (i.e., analytes that are denser than the sample fluid) towards, and eventually onto, the waveguide's inner surface (if there is no non-fluid detection layer); or towards, and eventually onto, the inner surface of the innermost non-fluid detection layer that may be present on the waveguide's inner surface.

Such centrifugal concentration of high density analytes may be highly desirable because, for example, the greater the quantity or number of high-density analytes that have been concentrated onto the waveguide's inner surface or onto the inner surface of the innermost non-fluid detection layer, the greater the amount of signal light that may be emitted from the waveguide's outer surface. Greater amounts of signal light may desirably translate into faster detection of the high-density analytes; into more sensitivity to the high-density analytes, so that as few as one individual analyte of a particular kind of high-density analyte may be detected in some cases; and into more accuracy in measurements taken of the high-density analytes.

The centrifugal force imparted by such spinning of the cup may also serve, for example, to centrifugally-concentrate any low-density debris in the sample fluid (i.e., debris that is less dense than the sample fluid, such as lipids for example) towards, and eventually along the inner surface of the layer of the sample fluid that is formed while the cup is spinning. Such centrifugal-concentration of low-density debris may be highly desirable because, for example, it may help to reduce any measurement errors that might otherwise be caused by such low-density debris if it remained along the waveguide's inner surface (if there is no non-fluid detection layer); or remained along the inner surface of the innermost non-fluid detection layer that may be present on the waveguide's inner surface.

The centrifugal force imparted by such spinning of the cup may also serve, for example, to form the sample fluid into a thin layer on the waveguide's inner surface (if there is no detection layer), or on the inner surface of the innermost non-fluid detection layer that may be present on the waveguide's inner surface. The thin layer of the sample fluid may have an optically flat inner surface. This may be highly desirable because, for example, it may enable the thin layer of the sample fluid to act as one of the detection layers in the detection coating on the waveguide's inner surface.

Spinning of the cup may also serve, for example, to circulate the sample fluid within the cup, such as if the cup is spun at varying rotational velocities. This may be highly desirable because, for example, it may help to expose any high-density analytes in the sample fluid to any non-fluid detection layer on the waveguide's inner surface.

The cup's waveguide may be divided into at least one circumferential waveguide, the inner surface of which may define at least one respective circumferential or axial testing segment. Any particular testing segment may be provided with a respective reservoir for fluid storage, and the cup's interior volume may include a respective analyte detection coating for at least one of the testing segments.

Any particular pair of adjacent circumferential waveguides and their respective testing segments or reservoirs may be separated from each other by any suitable kind of demarcation. A particular demarcation may comprise any suitable demarcating structure or substance. For example, a particular demarcation may comprise a ridge that extends into the cup's interior volume. Alternatively, or in addition, a particular demarcation may comprise a hydrophobic coating applied to a portion of the inner surface of the waveguide or of the cup's base. All demarcations may not be the same.

A particular demarcation may serve one or more of the following functions: (a) providing a local null reference zone (such as, for example, by being selected to be inert with respect to a particular assay with which the cup may be used); (b) isolating a particular pair of adjacent testing segments or reservoirs from each other, thereby helping to prevent cross-contamination of their respective fluids; (c) providing a marker for identifying a particular testing segment or reservoir; and (d) helping to channel the reservoir fluid from a particular reservoir to its respective testing segment when the cup is spun.

Providing such circumferential testing segments may be desirable for one or more of the following reasons, which are given by way of example. They may permit the cup to be used to test for at least two different kinds of analytes at the same time, or to test for at least two different targeted distinguishing characteristics of the same kind of analyte at the same time. They may permit measurement accuracy to be increased by providing for the redundant testing for a particular kind of analyte, or for the redundant testing for the same targeted distinguishing characteristic of a particular kind of analyte. They may permit measurement errors in the testing to be reduced, such as by enabling the use of ratiometric analysis of the signal light emitted from the circumferential waveguides' outer surfaces at their respective demarcations or testing segments.

The present invention may be mass produced, low in cost, disposable, very compact, highly sensitive, and need only small volumes of fluids or detection coatings for proper operation.

The present invention may also be very versatile since, in general, it may be used with any suitable conventional assay for any particular kind of analyte.

In addition, in situations where the analytes may be found only infrequently, the cost per assay may be low. This is because, as in a sandwich format immunoassay for example, the assay cup of the present invention may remain active, i.e., not be used up, until the capture agents included in a detection layer in the detection coating have been substantially neutralized by the binding of the analytes to the capture agents.

It should be understood that the foregoing summary of the present invention does not set forth all of its objects, features, advantages, characteristics, structures, materials, methods and processes; since these and further objects, features, advantages, characteristics, structures, materials, methods and processes of the present invention will be directly or inherently disclosed to those of ordinary skill in the art to which it pertains in view of all of the disclosures herein.

BRIEF DESCRIPTION OF THE SEVERAL VIEWS OF THE DRAWING

FIG. 8 is an enlarged view of a portion of the FIG. 7 embodiment, taken partly in cross section along line 8-8 of FIG. 7;

FIG. 9 is an enlarged cross sectional view of a portion of FIG. 8;

Figure 1:
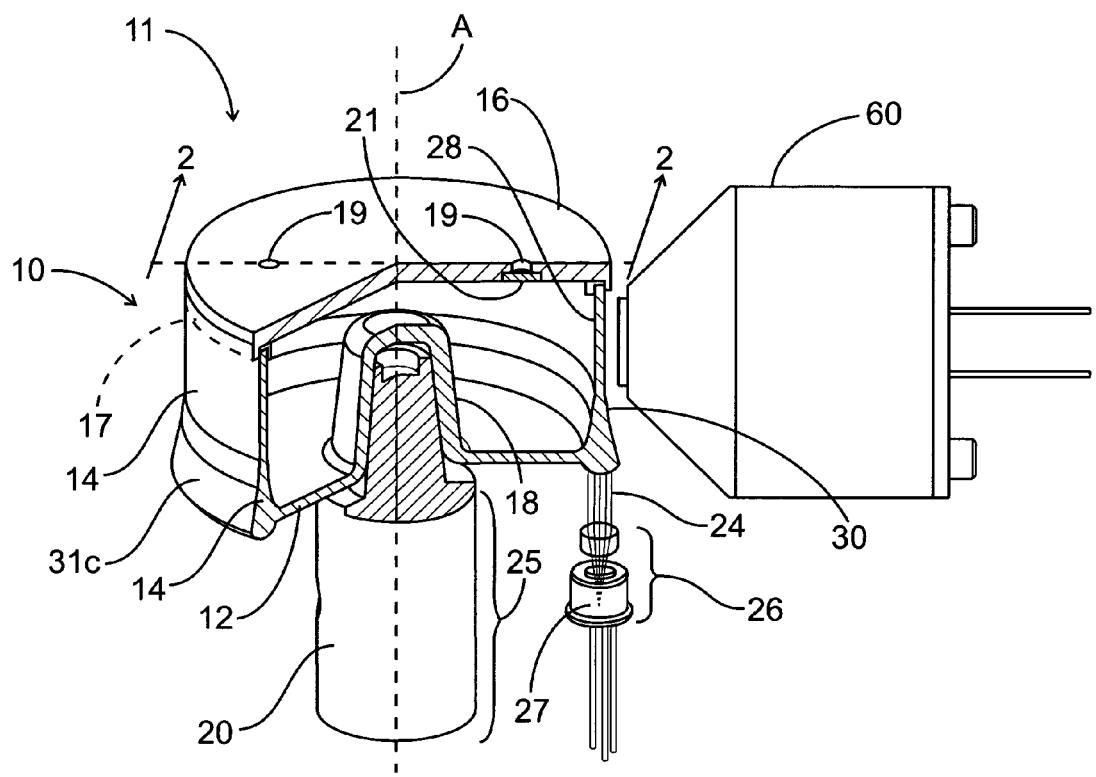
FIG. 1 is a diagrammatic perspective view of one embodiment of the optical assay apparatus of the present invention, partly in cross section to show internal features.

In many of the Figures, some or all of the parts described as being shown in cross section have not been hatched, for clarity and ease of understanding.

DETAILED DESCRIPTION OF THE INVENTION

Overview of Optical Assay Apparatus 11

Turning now to FIGS. 1-3 and 5, as has been mentioned the optical assay apparatus 11 of the present invention may be used to detect any analytes 52 of interest to the user. For example, the analytes 52 may be any organic or inorganic thing or material. Organic analytes 52 may be, for example, living or dead pathogens such as bacteria, viruses or spores; or may be any other biochemical or organic compounds of interest, such as toxins, small molecules or proteins. Inorganic analytes 52 may be, for example, chemical elements, such as metals; or may be inorganic compounds of interest.

Optical assay apparatus 11 may comprise an optical assay cup 10; and may further comprise a cover 16 for cup 10. It is understood that cups 10, 210, 210a, 310, and 410 are the same as each other, or are at least similar to each other, in any particular respect such as with respect to their respective mountings, locations, quantities (how many), sizes, shapes, designs, materials, compositions, constructions, manufactures, physical properties, dimensions, specifications, variations, operations, methods, and uses, except for those differences which will be made apparent by all of the disclosures herein.

Similarly, it is understood that cover 16 for cup 10 and cover 316 for cup 310 are the same as each other, or are at least similar to each other, in any particular respect such as with respect to their respective mountings, locations, quantities (how many), sizes, shapes, designs, materials, compositions, constructions, manufactures, physical properties, dimensions, specifications, variations, operations, methods, and uses, except for those differences which will be made apparent by all of the disclosures herein. Covers 16 or 316 may be used with one or more of cups 10, 210, 210a, 310 or 410.

As seen in FIGS. 1-3 and 5, optical assay apparatus 11 may further comprise a light source 26 for emitting light source interrogation light 24; a detector 60 for detecting output signal light 58 emitted from waveguide 28's outer surface 34 as a function of the presence, quantity, number, or at least one distinguishing characteristic of the analytes 52; and a spinning apparatus 25 for causing cup 10 (and any cover 16) to spin on their central A-axis.

Any suitable mounting apparatus (not illustrated, for clarity), may be used to mount cup 10, light source 26, detector 60 and spinning apparatus 25 in any suitable way with respect to each other so that any and all of these components may operate together and perform their various respective functions as described herein. For example, the mounting apparatus may simply comprise a base to which any of cup 10, light source 26, detector 60 and spinning apparatus 25 may be mounted directly, or indirectly as through the use of any suitable respective supports. Cup 10 may, for example, be mounted to spinning apparatus 25 which may then, in turn, be mounted to such a base directly, or indirectly.

Any suitable spinning apparatus 25 may be used to cause cup 10 to spin on its A-axis in any suitable way. For example, spinning apparatus 25 may comprise any suitable motor, gearbox, or drive train (not illustrated, for clarity) having a drive shaft 20; in which case the cup 10's base 12 may be provided with a drive shaft holder 18 that is sized to receive shaft 20. Alternatively, cup 10's cover 16 may be provided with a drive shaft holder 18, so that the spinning apparatus may spin cover 16, which, in turn, may spin cup 10.

Alternatively, the spinning apparatus may comprise any suitable turntable that is caused to spin in any suitable way, such as by any suitable motor, gearbox or drive train; in which case cup 10 or its cover 16 may then be mounted to such a spinning apparatus in any suitable way, so that as the turntable is spun, cup 10 is also spun. In such a case drive shaft holder 18 may be eliminated and cup 10's base 12 may be unbroken and extend from sidewall 14 to the A-axis. Numerous other ways of mounting cup 10 or its cover 16 and causing cup 10 to spin, either directly or indirectly, will be apparent to those of ordinary skill in the art, and so will not be discussed further herein.

Physical Construction of Cup 10 and Cover 16

Figure 2:
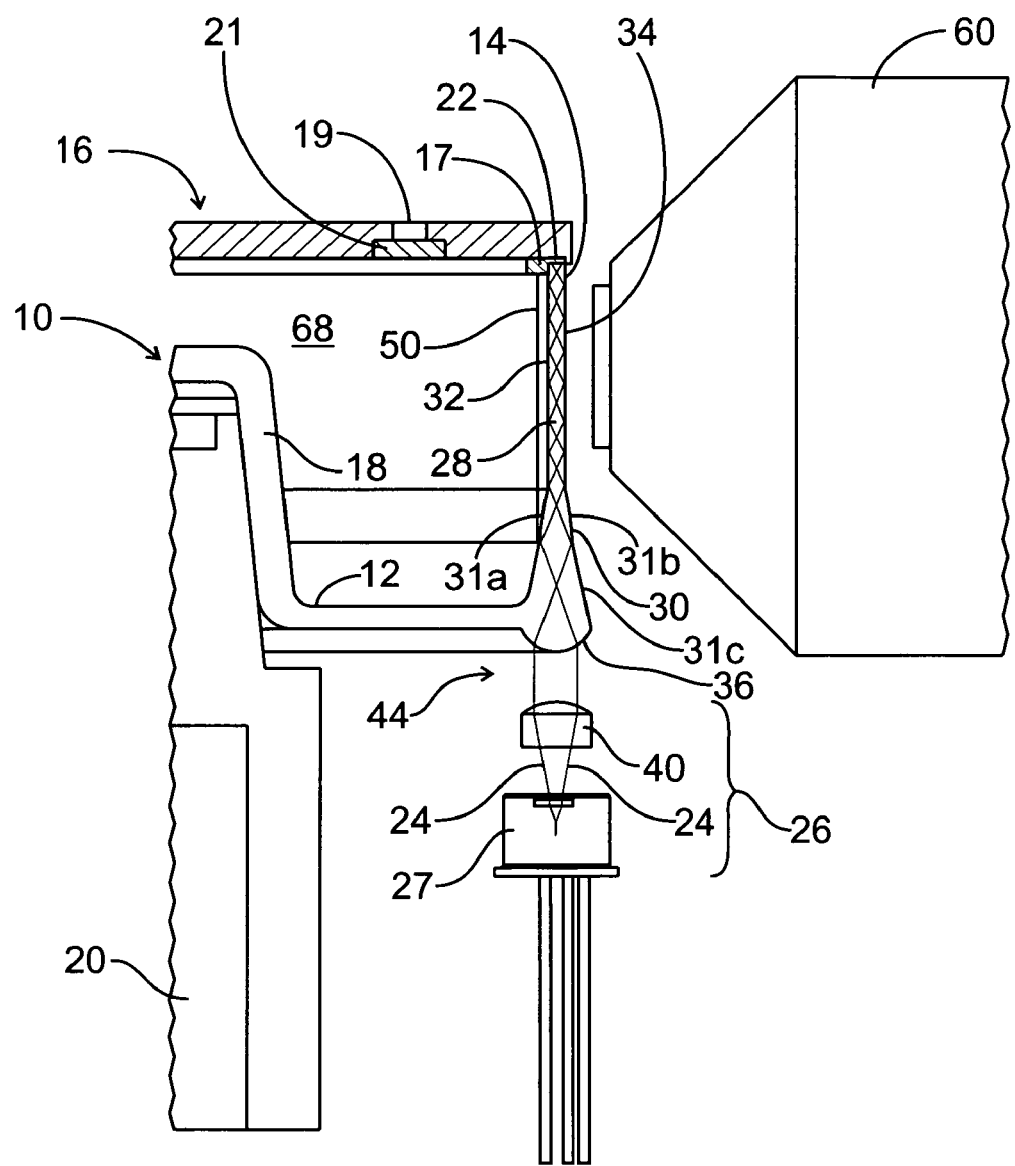
FIG. 2 is an enlarged, side elevational view of a portion of the FIG. 1 embodiment, taken partly in cross section along line 2-2 of FIG. 1.
Figure 3:
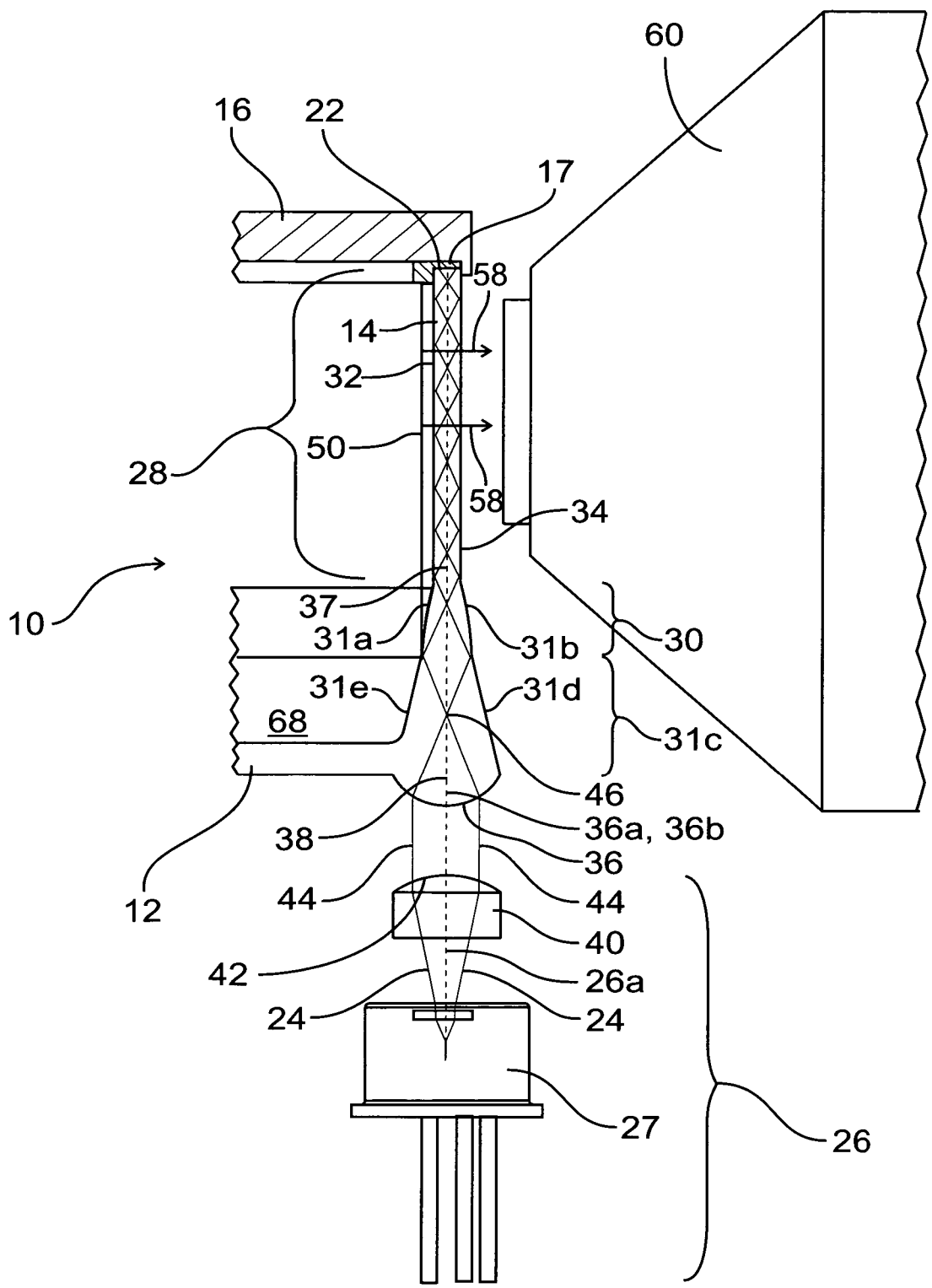
FIG. 3 is an enlarged view of a portion of FIG. 2, taken partly in cross section.

As seen in FIGS. 1-3, cup 10 may comprise a base 12 and a sidewall 14. Sidewall 14 may comprise an optical waveguide portion 28 having inner and outer optical surfaces 32, 34; a reflective surface portion 30 having inner and outer optically reflective surfaces 31a, 31b; and a lens support portion 31c, having inner and outer surfaces 31e, 31d, that extends between reflective surface portion 30 and a proximal edge 36.

Hereinafter, for simplicity, the optical waveguide portion 28 will be referred to as waveguide 28; the reflective surface portion 30 will be referred to as reflector 30; and lens support portion 31c will be referred to as lens support 31c.

Cup 10 may be of any suitable size, as determined by such factors as the needs of the user, the quantity of sample fluid 55, the nature of a particular kind of analyte 52 that may be present in sample fluid 55 (not shown in FIGS. 1-3), and the desired measurement sensitivity or accuracy, for example.

By way of example, cup 10 may have an outer diameter of from about 0.5 cm to about 10 cm, a sidewall 14 from about 0.1 to about 2.0 cm tall, and a volume of from about 0.020 cc to about 150 cc; although any of these parameters may be greater or smaller.

By way of further example, for a cup 10 having an inside diameter of 3.6 cm, and a sidewall 14 having a height of 1.3 cm, waveguide 28 may have a length of up to about 1.0 cm and a thickness of about 0.15 cm; and reflector 30 may have a length of about 0.24 cm, and a maximum thickness of about 0.22 cm; and lens support 31c may have a length of about 0.06 cm and a maximum thickness at its proximal edge 36 of about 0.22 cm. Cover 16 may be sized appropriately to fit cup 10.

As used herein regarding cup 10, cover 16 and their various parts and related components, unless the context should clearly indicate otherwise, the term "inner" refers to something that is closer, or closest to, the A-axis of cup 10 and cover 16; while the term "outer" refers to something that is further, or furthest away from, the A-axis. For example, waveguide 28's inner surface 32 is closer to the A-axis than is its outer surface 34.

Cup 10 may be manufactured in any suitable way. For example, it may be integrally formed in any suitable way, such as by injection molding. Alternatively, cup 10 may comprise several separate pieces that may then be joined together in any suitable way.

If integrally formed, its mold may be made in any suitable way, such as by using diamond turning methods, or by use of a precision CNC (computer numerically controlled) lathe and post-machining polishing.

Cover 16 may similarly be manufactured in any suitable way.

As best seen in FIG. 3, a fluid-tight seal 17 may be provided between cover 16 and distal edge 22 of cup 10's sidewall 14, to prevent leakage of any fluids placed in cup 10, such as sample fluid 55, for example. Seal 17 may be of any suitable construction such as, for example, a gasket. Alternatively, a separate seal 17 may be eliminated, and the desired seal may be provided in any suitable way, such as by providing a fluid-tight fit between cover 16 and distal edge 22, or by providing a fluid-tight joint between cover 16 and distal edge 22 by laser joining or ultrasonic welding, for example.

Cover 16 may be provided with any suitable means for adding and removing fluids from cup 10's interior volume 68 without leakage of the fluids from cup 10, such as one or more holes 19 and respective needle septums 21 comprising a self-sealing elastomeric material. Alternatively, one or more of holes 19 may be used without a respective needle septum 21, in which case such a hole 19 may preferably be located towards cup 10's A-axis, so that fluids inside of cup 10 do not leak from such a hole 19 while cup 10 is being spun during use.

A separate cover 16 may be optional, in which case at least some of the functions of cover 16 (e.g., to retain fluids within cup 10, and to keep foreign matter out of cup 10's interior volume 68), may be at least partially performed by providing a radially inwardly extending lip on distal edge 22 of cup 10's sidewall 14 that extends partly, or wholly, from sidewall 14 to cup 10's A-axis.

Although cup 10's base 12 is illustrated as being circular, flat, and as having a uniform thickness, base 12 may comprise any other regular or irregular geometric or non-geometric shape, all or part of base 12 may or may not be flat, and base 12 may or may not have a uniform thickness.

Alternatively, cup 10's base 12 may be reduced in size, or eliminated, such as if it were replaced by one or more spokes that extended between the drive shaft holder 18 and sidewall 14. In such an event, the proximal and distal edges 36, 22 of sidewall 14 may be provided with respective rims (not illustrated, for clarity) that extend towards the A-axis a respective distance that may be selected to be sufficient to contain whatever volume of fluid cup 10 may hold while it is being spun.

Although cup 10's sidewall 14 is illustrated as having a circular cross-sectional configuration relative to axis A, sidewall 14's cross-sectional configuration may comprise any other regular or irregular geometric or non-geometric shape; sidewall 14's cross-sectional configuration may or may not be the same from its proximal edge 36 to its distal edge 22 (e.g., its cross-sectional configuration may change in shape, size, or thickness from its proximal edge 36 to its distal edge 22); and sidewall 14 may not be of uniform shape, size, or thickness as one travels about the circumference of cup 10's sidewall 14. In addition, cup 10's sidewall 14, and thus its waveguide 28 and reflector 30, may not be continuous as one travels about sidewall 14's periphery, but instead may have gaps or openings of any size.

Figure 5:
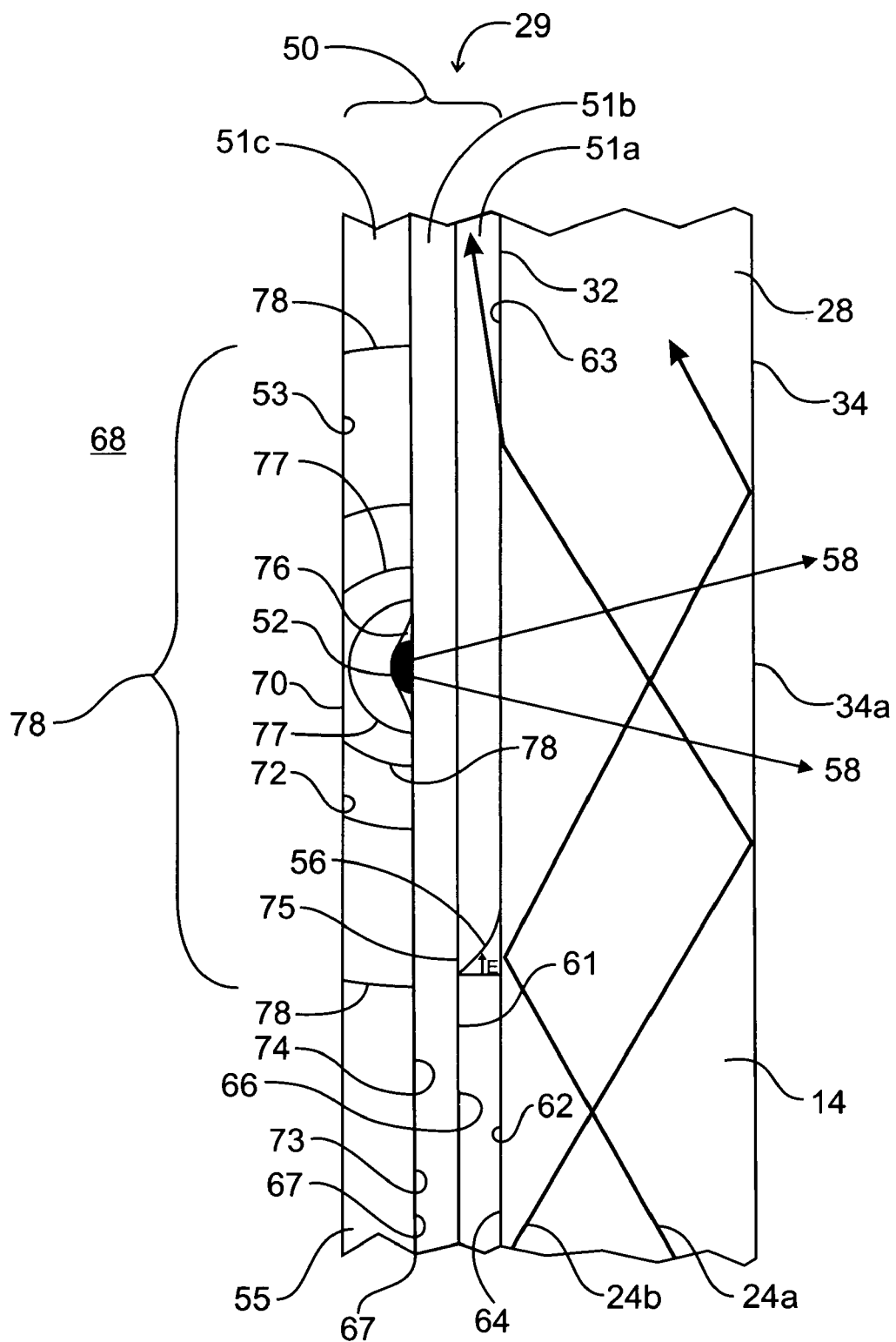
FIG. 5 is an enlarged cross sectional view of a portion of FIG. 2, showing the waveguide and the detection layers on the waveguide's inner surface.

As has been mentioned, and as best seen in FIGS. 2-3 and 5, cup 10's sidewall 14 may comprise a waveguide 28 and a reflector 30.

Waveguide 28 and reflector 30 may each have respective circumferential arc lengths that are less than, or equal to, the total circumference of sidewall 14. In addition, sidewall 14's circumference may be divided into two, or more, individual waveguides 28 and reflectors 30, not illustrated for clarity.

Waveguide 28 may have a length that extends partly or completely between the reflector 30 and distal edge 22 of sidewall 14. Minimizing the length of waveguide 28 to that which is strictly needed for optical and assay purposes may have the advantage of reducing the cost of manufacturing cup 10, since the needed optically smooth inner and outer surfaces 32, 34 of waveguide 28 are costly to create. For example, if cup 10 is an injection molded part, minimizing the length of waveguide 28 may minimize injection mold construction costs; and may allow more draft to be built into the mold, which will allow cup 10 to be removed more easily from the mold and minimize scratches on the optically smooth surfaces 32, 34 during extraction of cup 10 from its mold.

Alternatively, no reflector 30 may be provided, in which case waveguide 28 may have a length that extends partly or completely between sidewall 14's distal edge 22 and lens support 31c. If no reflector 30 is provided, then at least some of the functions of reflector 30 which are described below in detail, may be provided by any suitable optics (including reflectors), that may be located either interiorly or exteriorly of cup 10's sidewall 14.

Alternatively, no lens support 31c may be provided, in which case waveguide 28 may have a length that extends partly or completely between sidewall 14's proximal and distal edges 36, 22; or reflector 30 may have a length that extends partly or completely from waveguide 28 to sidewall 14's proximal edge 36.

Waveguide 28 may have an optical surface of symmetry 37 and may be of at least substantially uniform thickness as defined between its inner and outer surfaces 32, 34. Alternatively, waveguide 28 may not be of uniform size, shape, or thickness along its length or circumferential arc width. For example it may taper, increase, decrease or change in thickness along part or all of its length or circumferential arc width.

Reflector 30 may have a length that extends partly or completely between sidewall 14's proximal edge 36 and waveguide 28. Reflector 30 may have an optical surface of symmetry 38 that lies between its inner and outer surfaces 31a, 31b. Inner and outer surfaces 31a, 31b may converge towards optical surface of symmetry 38 along part or all of their respective lengths as one moves from proximal edge 36 to waveguide 28. Although both inner and outer surfaces 31a, 31b are illustrated as so converging, only one of them may so converge, and if both such surfaces 31a, 31b converge, they may not converge by the same amounts along part, or all, of their respective lengths. Reflector 30 may include only one optically reflective surface, which may be either surface 31a or 31b.

Reflector 30 may be of at least substantially uniform size or shape along its length or circumferential arc width. Alternatively, it may taper, increase, decrease or change in size or shape along part or all of its length or circumferential arc width.

Waveguide 28 and reflector 30 may be cylindrically symmetrical relative to cup 10's A-axis as best seen in FIG. 1. In such an event, their respective optical surfaces of symmetry 37, 38 (see FIG. 3) may each comprise a respective cylindrical shape, and may form a common optical surface of symmetry 39 if extended towards each other (see FIG. 4).

However, the term "cylindrical" as used herein with respect to waveguide 28, reflector 30, or their respective optical surfaces of symmetry 37, 38, may have a broader meaning than the common, literal definition of the term "cylindrical" and may encompass, for example, a waveguide 28 or a reflector 30 (and hence their corresponding optical surfaces of symmetry 37, 38) which are bowed inwardly or outwardly, which form an inwardly or outwardly diverging funnel-like shape, or which are skewed sideways, all with respect to cup 10's A-axis.

In addition, waveguide 28 or reflector 30 (and hence their corresponding respective optical surfaces of symmetry 37, 38) may be different, in that they may be bowed inwardly or outwardly by differing amounts, may form inwardly or outwardly diverging funnel-like shapes of differing sizes, or may be skewed sideways by differing amounts, all with respect to cup 10's A-axis.

As best seen in FIG. 3, part or all of the proximal edge 36 of cup 10's sidewall 14 may comprise any suitable refractive surface profile (i.e., an edge lens 36) for focusing part or all of interrogation light 24 from light source 26 onto reflector 30's inner and outer surfaces 31a, 31b, or directly into waveguide 28.

For the discussion herein it will be assumed, for simplicity, that light source 26 is located so that its optical axis 26a is coincident with reflector 30's optical surface of symmetry 38, as seen in FIG. 3. However, in other cases it may be advantageous to rotate the respective optical axes 26a, 36a of light source 26 and edge lens 36 so that either or both of those axes are not on reflector 30's optical surface of symmetry 38, yet are still positioned so that rays of interrogation light 24 are made to pass through a curved focal line 46 of lens 36 and reflector 30 that is on reflector 30's optical surface of symmetry 38. For example, this may be done to direct a large fraction of interrogation light 24 substantially or completely towards one or the other of reflector 30's reflective surfaces 31a or 31b, potentially eliminating the need to create two optically smooth reflective surfaces 31a and 31b. An example of this design approach is also presented herein. However, this is a relatively minor modification that can be made by someone skilled in the art once the fundamental concepts of the present invention, as outlined below, are understood.

The refractive surface profile of proximal edge 36 may be cylindrical, and may be aspherical or non-aspherical. Proximal edge 36 may also incorporate a short circumferential barrier wall on one or both of its inner and outer edges, to help prevent finger contact or physical damage to its refractive surface during handling of the cup 10.

Alternatively, proximal edge 35 may be flat; and not comprise such a refractive surface, in which event any suitable optics external to proximal edge 36 may be utilized to perform part or all of the functions of the refractive surface profile of proximal edge 36.

Referring now to FIGS. 1-3 and 5, waveguide 28 and reflector 30 may be formed from any suitable material that is at least substantially transparent to interrogation light 24 that is emitted by light source 26, and waveguide 28 may be formed from any suitable material that is also substantially transparent to signal light 58. Suitable materials may be plastic, glass, or quartz, for example.

As will be explained in more detail below, waveguide interrogation light 24a, 24b (see FIG. 5) for waveguide 28 may comprise at least some of light source interrogation light 24 emitted from light source 26.

As used herein, the term "light", such as interrogation light 24, 24a and 24b, or signal light 58, for example, may comprise any form of electromagnetic radiation from about 200 nm to about 10,000 nm in wavelength.

Orientation of Cup 10

Cup 10 (and its associated light source 26 and detector 60) may be used in any of the ways and with any of the assays described herein with any suitable orientation of cup 10's A-axis.

For example, cup 10's A-axis may be oriented vertically, or at least substantially vertically, as seen in FIG. 1; its A-axis may be oriented horizontally, or at least substantially horizontally, which may be seen by rotating cup 10 of FIG. 1 to either the right or left by 90°; or its A-axis may be oriented at any desired angle between vertical and horizontal. As used herein with respect to the orientation of cup 10's A-axis, the terms vertical and horizontal may also include the meaning of at least substantially vertical, and at least substantially horizontal, respectively Cup 10 may be mounted with its base 12 oriented partially down, which may be seen by rotating cup 10 of FIG. 1 to either the right or left by less than 90°, or oriented wholly down as seen in FIG. 1. Alternatively, cup 10 may be mounted with its base 12 oriented partially up, which may be seen by rotating cup 10 of FIG. 1 to either the right or left by more than 90°, but less than 180°, or with its base 12 oriented wholly up, which may be seen by rotating cup 10 of FIG. 1 to either the right or left by 180°.

It is understood that if cup 10's A-axis is placed in some non-vertical orientation, then light source 26 and detector 60 will also have to be moved and re-oriented by the same amount, so that their respective positions and orientations with respect to cup 10 remain unchanged. For example, let it be assumed that cup 10 is oriented so that its A-axis is horizontal (e.g., cup 10 of FIG. 1 is rotated to the right by 90°). In such a case, then light source 26 will also have to moved and rotated to the right by 90° so that it is in a proper position to inject interrogation light 24 into proximal edge 36 of cup 10; and detector 60 will also have to be moved and rotated to the right by 90° so that it is in a proper position to receive signal light 58 that is emitted from waveguide 28's outer surface 34. This may be seen by rotating FIG. 1 in its entirety to the right by 90°.

Regardless of what orientation cup 10's A-axis may have during use of cup 10, seal 17 between its sidewall 14 and its cover 16 will prevent any leakage of fluid (e.g., a sample fluid 55 or a reagent fluid) from cup 10, while septums 21 in its cover 16 will permit fluids to be added to and removed from cup 10 without leakage from cup 10.

Any non-vertical orientation of cup 10's A-axis may offer several advantages. For example, let it be assumed that the A-axis is oriented horizontally. Then gravity will tend to cause any fluid within cup 10's interior volume 68 to form a fluid pool in the lowest section of cup 10's curved sidewall 14. Then, if cup 10 is spun slowly, the fluid pool will tend to remain fixed in that lowest section, and drain away from sidewall 14 as any particular point on sidewall 14 rotates up and away from that lowest section. As a result, such spinning of cup 10 may desirably help to provide any needed mixing of any fluids that have been added to cup 10, and any needed distribution of such fluids as a thin coating on the waveguide 28's entire inner surface 32 (if cup 10 has no detection coating 50); on the entire inner surface 53 of any detection coating 50 on waveguide 28's inner surface 32; or on the entire inner surface 61, 73 of the innermost non-fluid detection layer 51a or 51b, respectively, that may be present on waveguide 28's inner surface 32 (see FIG. 5). The detection coating 50 (i.e., detection layers 51a, 51b, 51c) may comprise part of the cup 10's interior volume 68.

Turning now to FIGS. 2-3 and 5, any suitable detection coating 50 for a particular kind of analyte 52 in sample fluid 55 may be provided in any suitable way on part or all of waveguide 28's inner surface 32. Alternatively, there may be no detection coating 50 on part, or all of inner surface 32.

By way of non-limiting example, detection coating 50 is illustrated in FIG. 5 as comprising three detection layers 51a, 51b and 51c. However, detection coating 50 may comprise a single detection layer 51a, 51b, or 51c; two detection layers (such as 51a and 51b or 51b and 51c); or more than three detection layers. Each detection layer 51a, 51b and 51c may have the same or different compositions; and may be of uniform or non-uniform size, shape and thickness with respect to any of the other detection layers 51a, 51b and 51c.

In addition to mixing any fluids within cup 10, each complete rotation of cup 10 may provide contact of the fluid pool with, for example, waveguide 28's entire inner surface 32 (if cup 10 has no detection coating 50); with the entire inner surface 53 of any detection coating 50 on waveguide 28's inner surface 32; or with the entire inner surface 61, 74 of the innermost non-fluid detection layer 51a or 51b, respectively, that may be present on waveguide 28's inner surface 32 (see FIG. 5).

Such contact may be very useful in performing any suitable assay for any particular kind of analyte 52, or for any particular targeted distinguishing characteristic of a particular kind of analyte 52. For example, if a sandwich format immunoassay is used, such contact may help ensure that the capture molecules on inner surface 74 of a capture layer 51b of detection coating 50 are effectively exposed to all analytes 52 in sample fluid 55, to enable the capture molecules to capture as many of the analytes 52 as possible. Sandwich format immunoassays will be discussed below in more detail.

Further, a fluid layer 51c (e.g., comprising sample fluid 55 or a reagent) will be formed on waveguide 28's entire inner surface 32 (if cup 10 has no detection coating 50); on the entire inner surface 53 of any detection coating 50 on waveguide 28; or on the entire inner surface 74 of the innermost non-fluid detection layer 51a or 51b, respectively, that may be present on waveguide 28. In a cup 10 that is not rotating or rotating slowly, such a fluid layer 51c will be thickest adjacent to any fluid pool in the lowest part of cup 10, and will gradually diminish in thickness from that point up. In the limit of a very thin residual layer of fluid 51c, it may be present in part or in total as microscopic fillets 76 that surround the analytes 52, such as bacteria, that have been captured by detection coating 50 (see FIG. 5).

Accordingly, by suitably adjusting the locations of light source 26 and detector 60 with respect to the circumference of waveguide 28 when the cup 10 is in a horizontal orientation, and by suitably adjusting the rotational speed of cup 10, it is possible to create a wide range of thicknesses for the fluid layer 51c at the observation area. In addition, fluid layer 51c in the observation area is being continually refreshed as cup 10 spins, so that its desired thickness remains constant because of the rotation.

It is understood that the observation area is the area of waveguide 28 (and any associated detection coating 50) that is being subjected to evanescent or darkfield interrogation, and that may be emitting signal light 58 in response to such interrogation.

In order to reduce the effect of random noise in signal light 58, and to determine the presence of very small quantities of a particular kind of analyte 52 that may be present in sample fluid 55, any suitable internal self-referencing technique may be employed. This may be done in any suitable way such as, for example, by temporarily storing the signal patterns of the electrical output signals produced by detector 60 as a function of signal light 58 that is emitted from waveguide 28's outer surface 34 as cup 10 is spun, and by then either adding or comparing the signal patterns from successive rotations so as to obtain a more statistically accurate time-dependent picture of signal light 58 that is produced for each observation area around the perimeter of cup 10. Such a strategy may allow any suitable technique, such as least squares fitting, to be used to reduce the effect of random noise in signal light 58, or to detect the presence of very small quantities of a particular kind of analyte 52 that may be present in sample fluid 55.

By way of further example, internal self-referencing may be created by observing and comparing signal light 58 at any two suitable observation areas on waveguide 28. For example, one observation area may be located at a section of waveguide 28 that is below the surface of the fluid pool in cup 10, while the other observation area may be located at any other suitable place on waveguide 28 that is above the surface of the fluid pool, such as at the highest section of waveguide 28.

In addition, since (as in a sandwich format immunoassay, for example) most chemical reactions that attach fluorescent indicators 77 in a reagent fluid to the analytes 52 that have been captured by capture layer 51b will be first-order with respect to the presence, quantity, number, or at least one targeted distinguishing characteristic of the analytes 52, this may allow the user to adjust for variations in the concentration of the reagent fluid where a particular assay is being performed by using an automated protocol over a fixed contact time between the reagent fluid and captured analytes 52.

As an alternative to slowly rotating cup 10 when its A-axis is oriented in a non-vertical orientation, such as when its A-axis is oriented horizontally, cup 10 may be spun at high speeds when its A-axis is in a non-vertical orientation. If this is done, it is expected that cup 10 may provide at least some, and perhaps all, of the benefits that will be discussed in detail below regarding spinning cup 10 at high speeds when its A-axis is oriented vertically.

Circulating Fluids in Cup 10

During use, it may be desirable to circulate any needed fluids in cup 10 because such fluid circulation may, for example, assist in providing an opportunity for the fluid and any of its constituents to interact with any fluids or other materials already in cup 10, to interact with waveguide 28's inner surface 32, or to interact with any detection coating 50 (e.g., the detection layers 51a, 51b or 51c) on waveguide 28's inner surface 32 (see FIG. 5). For example, if the fluid is sample fluid 55, then fluid circulation may assist in providing a better opportunity for all analytes 52 in sample fluid 55 to interact with capture layer 51b in detection coating 50, as compared to if there was no fluid circulation.

Fluid circulation in cup 10 may be provided in any suitable way, such as by periodically reversing the direction in which cup 10 is spun, by periodically changing the speed at which cup 10 is spun, by agitating cup 10 in any suitable way, by use of any suitable kind of stirring device within cup 10, or by providing vaned structures or radial fins within cup 10, for example.

However, it may be preferred that such circulation of the fluid not be so robust that it interferes with the proper operation of cup 10. For example, if the fluid is sample fluid 55, then the circulation of sample fluid 55 should not be so robust that it interferes with the proper operation of capture layer 51b, such as by causing significant quantities or numbers of previously bound analytes 52 to be stripped away from capture layer 51b.

Fluid Inventory Control

In many of the assays described herein, one goal may be to minimize the amount of fluid used in cup 10, since some reagents used in the assays may be costly. The thin fluid layer 51c in cup 10 may be advantageously used to help accomplish this goal, since it effectively minimizes the amount of any costly reagent that may be required while performing the assay.

However, as fluid volumes are reduced it becomes increasingly important to consider the effects of surface tension. Surface tension forces tend to create undesirable fluid-trapping fillets at sharp corners and it may be possible, if precautions are not taken, for the majority of an introduced reagent to be trapped in these parasitic fluid fillets. This reduces reagent availability for reactions used during the assay, and requires the use of more reagents than would at first appear necessary. In addition, these sharp corners may be difficult to flush.

A particularly desirable cup 10 design strategy may be to minimize all unnecessary fluid traps by designing cup 10 so that its interior surfaces or features, such as its demarcations 86 and the intersections of its sidewall 14 with its cover 16 and bottom 12, do not form sharp, fluid trapping corners.

Figure 21:
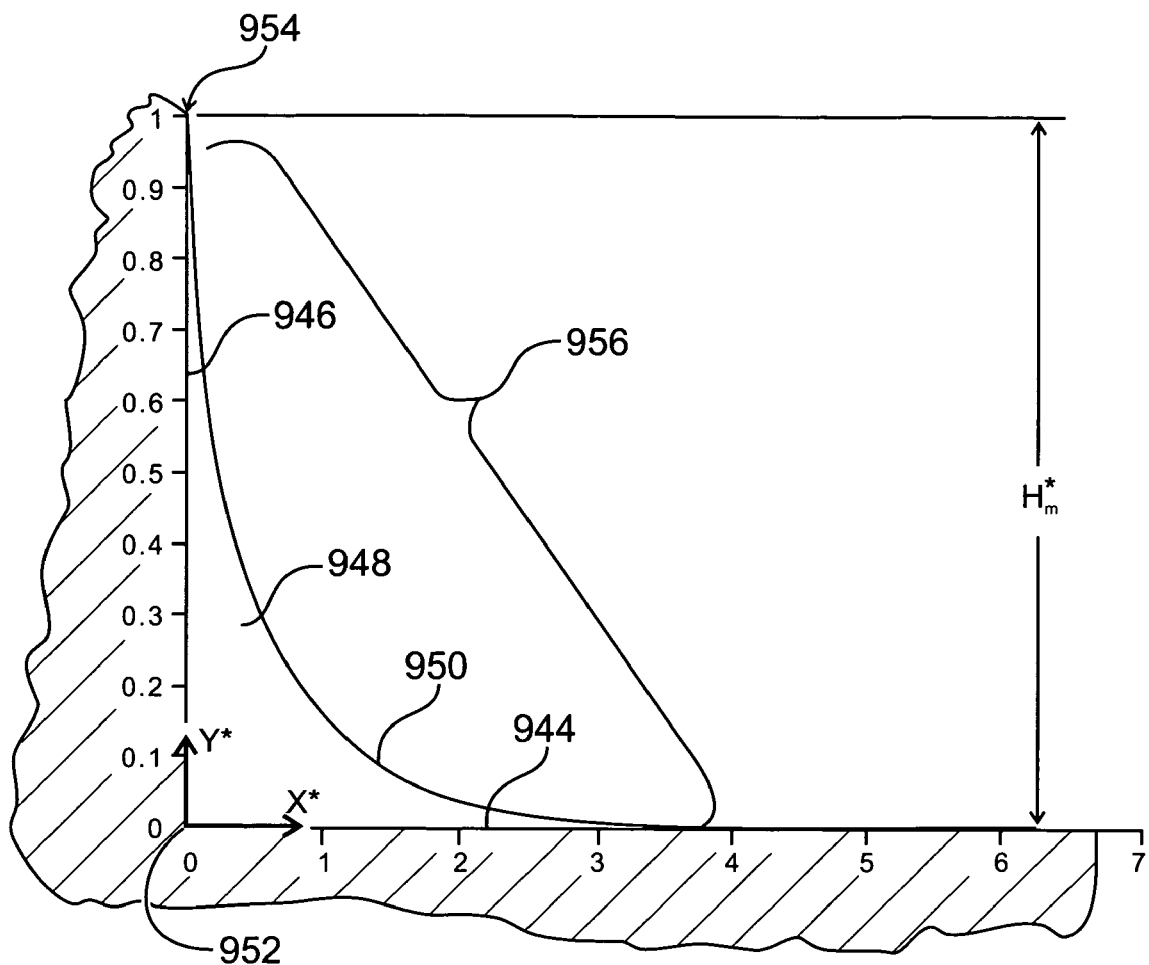
FIG. 21 is a diagrammatic, cross sectional view showing a fluid fillet formed by the intersection of horizontal and vertical surfaces, shown in cross section.

Referring now to FIG. 21, many fluid trapping problems are geometrically equivalent to a corner 952 that has been formed by the right angle intersection of horizontal and vertical planes 944, 946. FIG. 21 was produced by assuming that a fluid pool (not illustrated, for clarity), lay on horizontal plane 944. From this pool arose a fluid corner fillet 948 having a top end 954 and a surface 950. The contact angle between surface 950 and plane 946 at top end 954 is assumed close to zero.

The vertical climb height, $H_m$, of the fluid making up fillet 948 against the force of gravity can be readily shown to be given by:

$$H_m = \left(\frac{2\gamma}{\rho g}\right)^{1/2} \qquad \text{Equation 1}$$

Where $\gamma$ is the fluid's surface tension, $\rho$ is the fluid's density, and g is gravitational acceleration. Surface tension is intrinsically a surface phenomena and surface tension-dominated fluid structures are unaffected by the shape of non-fluid objects under the fluid surface that do not protrude through or contact the fluid surface. By replacing fluid fillet 948 in corner region 956 with a non-fluid fillet 948 that approximates fluid surface 950's profile, fluid entrapment in corner region 956 may be reduced by a factor of 10 times or more.

For intersecting planes 944, 946 the shape of surface 950 at intermediate points between surface 944 and its maximum climb height at its top end 954 is not amenable to a closed-form analytical solution. However, the shape of surface 950 is governed by a well-known second-order differential equation and solutions for various boundary conditions in two or three dimensions may be determined by numerical methods. In the following Equation 2, $X^*$ is the dimensionless horizontal position of a point X on fluid surface 950's profile, measured from the vertical plane 946, which has been normalized by dividing X by the climb height, $H_m$, of Equation 1. Similarly, in the following Equation 3, $Y^*$ is the dimensionless vertical position of a point Y on fluid surface 950's profile, measured from the horizontal plane 944, which has been normalized by dividing Y by the climb height, $H_m$, of Equation 1. Then X* is closely approximated by the following polynomial curve-fit function of Y:

$$X^* = 9.171942 - 31.072549T + 51.764319T^2 - 46.863531T^3 + 17.000634T^4 \quad \text{Equation 2}$$

where:

$$T = Y^{*0.234} \quad \text{Equation 3}$$

If planes 944, 946 are modified in the corner region 956 to create a non-fluid cross-sectional profile as given by equation 2, a non-fluid corner fillet 948 will be produced that closely matches the surface 950 of the fluid corner fillet 948; thereby minimizing the surface tension-dominated volume of any fluid fillet 948 that may overlie such a non-fluid fillet 948. This is an illustrative example of a generic strategy for minimizing fluid fillet volume.

The specific surface shape selected for the non-fluid corner fillet 948 may depend on many factors, such as the contact angles of the fluid with planes 944, 946; the total fluid volume introduced, the presence of surfactants in the fluid; and the presence of more complex underlying three dimensional surfaces, such as the intersection of a vertical plane 946 with the interior of a horizontal cylinder.

In each case, the interplay of the particular fluid's surface tension, gravity, and the shape and properties of the particular structure must be modeled in a relevant manner. In all cases the two- or three-dimensional shape of fluid fillet 948 must be replaced with a non-fluid fillet 948 having a surface profile selected to match, or at least approximate, fluid fillet 948's surface profile.

If cup 10 is made using injection molding methods, then the surface profile of the non-fluid fillet 948 located at the intersection of cup 10's base 12 and sidewall 14 may be created in any suitable way, such as by using a CNC machine tool to fabricate a mold, which may then be used to injection mold cup 10 from plastic, for example. Alternatively, non-fluid fillet 948's surface profile may be created by placing in cup 10 a suitable volume of UV-curable fluid pre-polymer compound having surface tension and wetting properties similar to those of the fluids to be used during a particular assay, spinning cup 10 to urge the pre-polymer compound into cup 10's corner region 956, and then polymerizing the pre-polymer to a solid polymer by the application of ultraviolet light while cup 10 is still spinning. Cup 10 may then be used to perform the desired assay; or the resulting surface profile of the non-fluid fillet 948 may be used as an empirical model from which the two- or three-dimensional surface profile of the solid polymer fillet 948 may be determined by any suitable mechanical or optical profiling method.

Light Source 26

Turning now to FIGS. 1-3, light source 26 may be used with any of the cups 10, 210, 210a, 310, 410 disclosed herein, and may comprise any suitable light emitter 27 for interrogation light 24, such as a laser, a light emitting diode (LED), a fluorescent light, or an incandescent filament, for example. Interrogation light 24 emitted by light source 26 may comprise one or more wavelengths, and may or may not be coherent.

Interrogation light 24 may be varied in wavelength in any suitable way. Light source 26 may comprise any suitable multiplexing equipment for multiplexing interrogation light 24 in any suitable way. Providing a light source 26 that emits interrogation light 24 of various wavelengths, or that is multiplexed, may be desirable since it may permit the simultaneous detection of more than one kind of analyte 52, or the simultaneous detection of more than one targeted distinguishing characteristic of the same kind of analyte 52 during the use of cup 10.

Light source 26 may further comprise any suitable lens 40 for focusing the interrogation light 24 as desired. Alternatively, lens 40 may comprise any suitable numerical aperture-adjusting lens 40 that may be used to produce a collimated beam 44 from interrogation light 24 that is emitted by light emitter 27. Lens 40 may, for example, comprise a plano-convex lens having an aspherical refractive surface 42, or a graded refractive index (GRIN) lens. In any event, lens 40 may comprise more than one individual lens.

In theory, interrogation light 24 from light source 26 may be obliquely injected in any suitable way directly into cup 10's interior volume 68 (e.g., into its detection coating 50) through waveguide 28's outer surface 34. However, higher interrogation light intensities may be created in waveguide 28 and detection coating 50 if interrogation light 24a, 24b is injected into the proximal edge 36 of cup 10's sidewall 14, or into the sidewall 14's outer surface in the vicinity of the proximal edge 36, thereby allowing interrogation light 24a, 24b to propagate as a narrow intense beam along the entire length of waveguide 28. This may be accomplished by injecting interrogation light 24a, 24b into sidewall 14's outer surface in any suitable way, such as by using a circumferential prismatic shape molded into sidewall 14's outer surface in the vicinity of its proximal edge 36, for example. The proximal edge 36 (which may be an edge lens 36), and such a circumferential prismatic shape may comprise part of the light source 26. Alternatively, this may be accomplished by using the axial light injection method described in detail herein, which injects the interrogation light 24a, 24b directly into the proximal edge 36. Both are within the scope of the present invention.

It may be noted that in practice, oblique injection of interrogation light 24a, 24b directly into waveguide 28's outer surface 34 may be topologically more difficult to accomplish since it may be difficult to mount both light source 26 and detector 60 adjacent to waveguide 28's outer surface 34 due to the relatively large size that detector 60 may have and its close proximity to surface 34. In addition, there may be more sensitivity to small misalignments of cup 10 relative to light source 26; optical structures located on waveguide 28's outer surface may be more exposed to fouling or damage; it may be more difficult to prevent surface reflections from waveguide 28's outer surface 34 from injecting flare light into detector 60; and the outside diameter of cup 10 may have to be enlarged proportionately more than would be the case if the axial light injection method described herein were used.

For example, if single-particle visualization of the analytes 52 is performed, a high-magnification, high numerical aperture objective lens may be a part of detector 60. This lens may need to be mounted in close proximity to waveguide 28's outer surface 34 for proper collecting and focusing of signal light 58 emitted from waveguide 28's outer surface 34. As a result, there may be insufficient room left for properly mounting light source 26 if it were desired to obliquely inject interrogation light 24a, 24b directly into waveguide 28's outer surface 34.

In addition, Fresnel secondary reflections arising from interrogation light 24 obliquely entering waveguide 28's outer surface 34 may result in some of interrogation light 24 being injected directly into detector 60, where it may create a large background output electrical signal that is difficult to effectively eliminate without compromising the efficiency of detector 60 in detecting signal light 58 emitted from waveguide 28's outer surface 34.

In view of the above, light source 26 and cup 10 may be designed, and located with respect to each other, in such a way, so as to permit the collimated beam 44 from lens 40 to enter cup 10's sidewall 14 through its proximal edge 36 which, as described above, may comprise an edge lens 36. By so locating light source 26, it advantageously does not interfere with any other hardware, such as detector 60, which may be mounted closely adjacent to waveguide 28's outer surface 34; and it advantageously does not create any undesirable Fresnel surface reflections from waveguide 28's outer surface 34 that might otherwise inject interrogation light 24 into detector 60.

The edge lens 36 may act as a focusing lens and focus the collimated beam 44 of interrogation light 24 (in a radial context only) onto the reflector 30's optical surface of symmetry 38, leaving the extent of beam 44 unaffected in a circumferential context. The required radial surface profile for such a line-focusing lens 36 is easily developed by one skilled in geometric optics. The light source 26 may further comprise the reflector 30.

Since the collimated beam 44 is typically circular or elliptical in cross-section, and lens 36 and reflector 30 are concentric features of the cup 10, the net effect of lens 36 may be to focus beam 44 of interrogation light 24 into a bright, curved line segment (focal line 46 of lens 36 and reflector 30) on the optical surface of symmetry 38, the focal line 46 being at a constant radius from the cup 10's axis A. Part or all of interrogation light 24 may then diverge from the focal line 46 to reflect from part or all of reflector 30's inner and outer surfaces 31a, 31b, and into waveguide 28. A portion of interrogation light 24 from focal line 46 may enter waveguide 28 without being first reflected from reflector 30's inner and outer surfaces 31a, 31b.

The focusing of beam 44 of interrogation light 24 by lens 36 into the bright, curved focal line 46 that was described above may be desirable because the circumferential arc over which interrogation light 24 may be distributed may be more easily controlled and the uniformity in angular orientation of interrogation light 24a, 24b that enters waveguide 28 may be greater, as compared to the case where interrogation light 24 is obliquely injected directly into cup 10's interior volume 68 (e.g., into its detection coating 50) through waveguide 28's outer surface 34, in the manner described above.

Although only one light source 26 is illustrated in FIGS. 1-3, as an alternative there may be more than one light source 26, in which case each light source 26 may be arranged about the circumference of proximal edge 36 of cup 10's sidewall 14 in a manner similar to that illustrated in FIGS. 1-3.

If there is more than one light source 26, then each light source 26 may emit interrogation light 24 of the same wavelength or multiplexed wavelengths. Providing at least two light sources 26 may be desirable, particularly if they emit interrogation light 24 of different wavelengths or multiplexed wavelengths, since they may permit the simultaneous detection of more than one kind of analyte 52, or the simultaneous detection of more than one targeted distinguishing characteristic of the same kind of analyte 52 during the use of cup 10.

As a further alternative, any particular light source 26 (and any particular accompanying numerical aperture-adjusting lens 40) may be used to produce more than one collimated beam 44 of interrogation light 24 for cup 10 by the use of any suitable optical device which divides an input collimated beam 44 into more than one output collimated beam 44; and which then directs at least some of the collimated output beams 44 into proximal edge 36 of cup 10's sidewall 14 at various locations around the circumference of proximal edge 36. Each such collimated output beam 44 may be of the same frequency or of multiplexed frequencies. Evanescent or darkfield interrogation light 24a, 24b may be of a single wavelength.

In any event, if ratiometric signal processing of the output electrical signals from detector 60 that are produced as a function of signal light 58 is desired, then the evanescent or darkfield interrogation light 24a, 24b may be of at least two wavelengths (which may come from different light sources 26), and one or more suitable detectors 60 (along with any needed suitable optical filters), may be used so that small changes in signal light 58, such as in its spectrum or amount, may be ratiometrically detected. Such ratiometric detection may also help to null errors that might otherwise occur in the electrical output signals from detector(s) 60 that are produced as a function of signal light 58.

Design of Reflector 30 of Cup 10's Sidewall 14

Either, or both, of inner and outer surfaces 31a, 31b of reflector 30 of cup 10's sidewall 14 may have a respective profile selected such that at least some rays of interrogation light 24 from light source 26 that are reflected from them may enter waveguide 28 within a narrow predetermined range of angles with respect to reflector 30's optical surface of symmetry 38. The respective profiles of surfaces 31a, 31b may be aspherical or non-aspherical, and may or may not be the same.

For cup 10 illustrated in FIGS. 1-3 the respective optical surfaces of symmetry 37, 38 of waveguide 28 and reflector 30, coincide with each other to form a common optical surface of symmetry 39.

Figure 4:
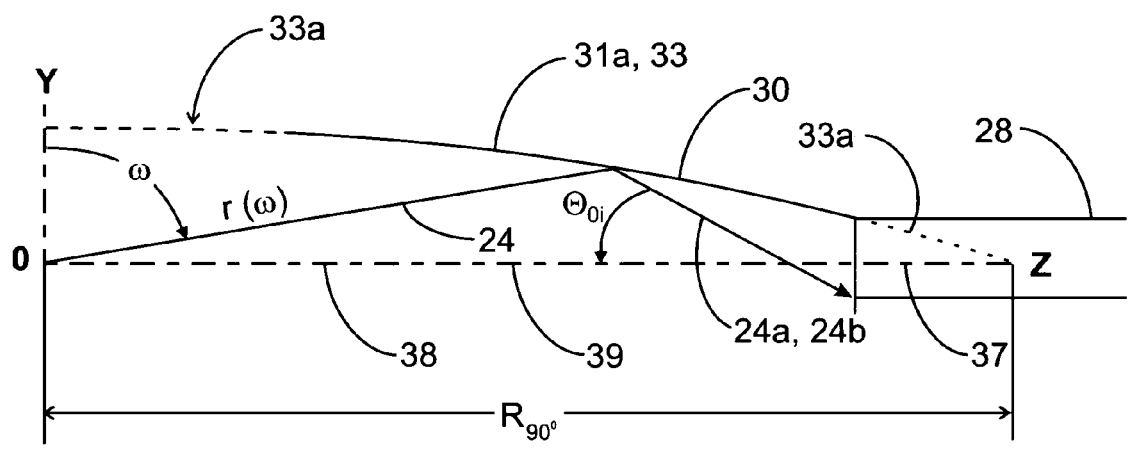
FIG. 4 is a depiction of the geometry of the reflector of the FIG. 1 optical assay cup's sidewall.

Turning now to FIG. 4, a local Z-axis may be defined (with no loss of generality), as being coincident with the common optical surface of symmetry 39, and as being oriented parallel to cup 10's A-axis. Alternatively, the optical surfaces of symmetry 37, 38 may not coincide with each other, so that the Z-axis lies only in reflector 30's optical surface of symmetry 38.

In FIG. 4, the origin "O" is at one point on the focal line 46 of lens 36 and reflector 30; and the positive Y-axis extends radially inwardly towards, and intersects with, cup 10's A-axis.

For simplicity, the following discussion will be made with respect to the shape of reflector 30's inner surface 31a, it being understood that similar comments may apply equally well to the shape of reflector 30's outer surface 31b.

For a reflector 30 having a rotationally symmetrical inner surface 31a, the shape of its inner surface 31a is defined by a partial or full rotation of curve 33 seen in FIG. 4 about cup 10's A-axis, which is parallel to the Z-axis seen in FIG. 4.

With a point light source for rays of interrogation light 24 assumed at origin "O", the shape of reflector 30's inner surface 31a may be described in accordance with the depicted polar coordinates as:

$$r(\omega) = R_{90°}\left[\frac{1-\cos(\theta_{90°})}{1-\sin(\omega-\theta_{0i})}\right]^P \qquad \text{Equation 4}$$

In above Equation 4, and as seen in FIG. 4, $r(\omega)$ is the distance from origin O to reflector 30's inner surface 31a; input interrogation ray 24 angle $\omega$ is the angle that a ray of input interrogation light 24 makes with respect to the Y-axis; the reflected angle $\theta_{0i}$ is the angle that a reflected ray of interrogation light 24 from reflector 30's inner surface 31a makes with respect to reflector 30's optical surface of symmetry 38 (which may be coincident with the common optical surface of symmetry 39); $R_{90°}$ is the distance from origin O to dotted extension 33a of curve 33 when input interrogation ray 24 angle ω is equal to 90°; $θ_{90}°$ is reflected angle $θ_{Oi}$ when input interrogation ray 24 angle ω is equal to 90°; and:

$$P = \frac{1}{1-B} \qquad \text{Equation 5}$$

where B is the rate of change in reflected angle $θ_{Oi}$ as a function of input interrogation ray 24 angle ω.

Above Equation 4 for r(ω) assumes reflected angle $ω_{Oi}$ changes in a linear fashion as a function of input interrogation ray 24 angle ω over the extent of curve 33, so that reflected angle $θ_{Oi}$ for any point on curve 33 is given by $$θ_{Oi} = A + Bω \qquad \text{Equation 6}$$

where A is reflected angle $θ_{Oi}$ when input interrogation ray 24 angle ω is zero.

It is believed that varying reflected angle $θ_{Oi}$ in a linear fashion as described above is the most complicated relation that still gives a closed-form equation. However, although no closed-form solutions for other dependencies of reflected angle $θ_{Oi}$ as a function of the input interrogation ray 24 angle ω are known, r(ω) can be derived for other monotonic relationships between reflected angle $θ_{Oi}$ and input interrogation ray 24 angle ω such as a power-law dependency.

For the special case that the parameter B is equal to zero, all rays of interrogation light 24 reflected from reflector 30's reflective surface 31a (curve 33) exit at the same angle $θ_{Oi}$ from reflective surface 31a and therefore all enter waveguide 28 at the same entry angle with respect to reflector 30's optical surface of symmetry 38 (see FIG. 4). This entry angle is $θ_{Oi}$ in value if the optical surfaces of symmetry 37, 38 coincide, or is a different angle if they are not coincident. This flexibility may be of significant value if, for example, a specific entry angle maximizes the strength of the output signal light 58. A range of exit angles $θ_{Oi}$ from reflector 30's reflective surface 31a is created by selecting a non-zero value for the parameter B. This provides a further tool to maximize strength of the output signal light 58, to manipulate the group characteristics of interrogation light 24, and to possibly compensate for variations in optical performance of the optical assay apparatus 11 due to manufacturing tolerances and user misalignment.

Detection Coating 50 (in General)

Turning now to FIGS. 2-3 and 5, any suitable detection coating 50 for any particular kind of analyte 52 in sample fluid 55 may be provided in any suitable way on part or all of waveguide 28's inner surface 32. Alternatively, there may be no detection coating 50 on part or all of waveguide 28's inner surface 32.

Detection coating 50, and any of the detection layers (e.g., layers 51a, 51b, 51c) that may form detection coating 50, may be a "fluid" (such as sample fluid 55, water or any suitable reagent, for example); or may be a "non-fluid".

The word "fluid" as used herein with respect to sample fluid 55, detection coating 50, or any of the detection layers (e.g., layers 51a, 51b, 51c), is used its broadest sense to include any fluid, such as a liquid or gas, or mixtures thereof; and further includes liquids or gasses carrying or mixed with any soluble or insoluble, organic or inorganic materials, and carrying or mixed with any dissolved or un-dissolved organic or inorganic materials.

Similarly, the word "non-fluid" as used herein with respect to detection coating 50 or any of the detection layers (e.g., layers 51a, 51b, 51c) is used its broadest sense to include anything that is not a "fluid" as defined above.

By way of non-limiting example, detection coating 50 is illustrated in FIG. 5 as comprising three detection layers 51a, 51b and 51c. However detection coating 50 may comprise a single detection layer 51a, 51b, or 51c; any two of detection layers 51a, 51b, or 51c (i.e., 51a and 51b, 51a and 51c, or 51b and 51c); or more than three detection layers 51a, 51b, 51c. Each detection layer 51a, 51b and 51c may have the same or different compositions; and may be of uniform or non-uniform size, shape and thickness with respect to any of the other detection layers 51a, 51b and 51c.

There may be an interface 64 at any area of contact between waveguide 28's inner surface 32 and the respective outer surfaces 63, 62 of detection coating 50 and detection layer 51a.

There may be an interface 70 at any area of contact between whatever is inside cup 10's internal volume 68 (such as air, for example), and the respective inner surfaces 53, 72, 74, 61 of detection coating 50 and detection layers 51c, 51b, 51a.

There may be an interface 66 at any area of contact between detection layers 51a and 51b, and an interface 67 at any area of contact between detection layers 51b and 51c.

For simplicity of description herein, and by way of non-limiting example, it will be assumed that layers 51a and 51b are non-fluid detection layers, while layer 51c is a fluid detection layer.

One of the important functions of detection coating 50 may be to directly or indirectly assist in detecting a particular kind of analyte 52 in sample fluid 55 in cup 10 by producing, or helping to produce, rays of signal light 58 that are emitted from waveguide 28's outer surface 34 as a function of any analytes 52 that may be present in cup 10's interior volume 68. Such signal light 58 may be emitted as a function of, for example, the presence, quantity, number, or at least one targeted distinguishing characteristic of the analytes 52. Such rays of signal light 58 may be produced, for example, either directly or indirectly by the analytes 52 or by detection coating 50 (e.g., by detection layers 51a, 51b, or 51c).

It is understood that rays of signal light 58 emitted from waveguide 28's outer surface 34 may comprise, for example, rays generated in detection coating 50 that may have wavelength(s) that are not the same as the wavelength(s) of evanescent or darkfield interrogation light 24a, 24b. The wavelength-shifted rays of signal light 58 may be produced in any suitable way such as, for example, through mechanisms such as fluorescence, phosphorescence, photonic up-conversion, Ramann scattering, or light-activated chemical reactions. Hereinafter, for simplicity, all mechanisms for producing wavelength-shifted rays of signal light 58, including all of the forgoing mechanisms, may be referred to as "fluorescent signal generating methods", since all wavelength-shifted rays of signal light 58 have similar properties and signal conditioning requirements. Accordingly, the wavelength-shifted rays of signal light 58 which they produce may be referred to as "fluorescent signal light 58".

Rays of fluorescent signal light 58 may be detected by reason of their intensity; spectral content relative to that of interrogation light 24a or 24b; phase-shift in emission relative to the applied interrogation light 24a or 24b; or by signal decay rate after application of interrogation light 24a or 24b.

Alternatively, rays of signal light 58 emitted from waveguide 28's outer surface 34 may be rays of interrogation light 24a or 24b. If signal light 58 comprises scattered rays of darkfield interrogation light 24b, such signal light 58 may emitted in any suitable way from waveguide 28's outer surface 34 as a function of, for example, the presence, quantity, number, or at least one targeted distinguishing characteristic of the analytes 52 that may be present in cup 10's interior volume 68.

For example, if the analytes 52 or detection coating 50 directly or indirectly absorb, reflect, refract or scatter darkfield interrogation light 24b, then the amount of signal light 58 may change as a function of the analytes 52; the respective spectrum shapes of signal light 58 and darkfield interrogation light 24b may be different; or the spectrum of signal light 58 may exhibit a time-varying quality that is related to presence, quantity, number, or at least one targeted distinguishing characteristic of the analytes 52 that may be present in cup 10's interior volume 68.

It may be desirable to intentionally incorporate within detection coating 50a homogeneously distributed scattering media that provides a regulated amount of scattered signal light 58 to detector 60 so that the opacity or color of the coating 50 can be monitored over its spatial extent. To achieve satisfactory and uniform optical response it may be necessary to adjust the amount of scattering media used, so that the available optical power is not materially affected over the observation area. If the scattering media is an extremely finely divided insoluble particulate material that has a substantively different refractive index from that of coating 50, then the amount of scattered signal light 58 is easily adjusted by changing the percentage of the scattering media in coating 50. Suitable scattering media include titanium dioxide pigments, fluoropolymer particles, and various insoluble organic pigments. If the interrogation light 24 lies in the visible light spectrum, acceptable particle sizes for the scattering media may range from about 100 Angstroms to about 1 micron, and acceptable particle loadings of the scattering media may range from about 0.01% to about 5% of the volume of the detection layer 50.

Alternatively signal light 58 may be emitted from waveguide 28's outer surface 34 directly or indirectly as a function of the analytes 52, even if there is no detection coating 50 on part, or all, of waveguide 28's inner surface 32.

Spinning Cup 10 to Centrifugally-Concentrate

High-Density Analytes 52

Referring again to FIGS. 1-3 and 5, to use the present invention a fluid (e.g., sample fluid 55, a reagent, or any other fluid) that may contain a particular kind of analyte 52 is added to cup 10. Cover 16 may be assumed to be secured in place on cup 10.

For simplicity, and by way of non-limiting example, it may also be assumed that the fluid containing analytes 52 is sample fluid 55, that there are three detection layers 51a, 51b and 51c; that layers 51a and 51b are non-fluid detection layers; and that layer 51c is a fluid detection layer.

One of the important advantages of the present invention is that it may be used to quickly, easily and effectively centrifugally-concentrate any high-density analytes 52 towards, and eventually onto, waveguide 28's inner surface 32 (if there are no non-fluid detection layers 51a, 51b), or towards and eventually onto inner surface 74 of the innermost non-fluid detection layer 51b that may be present on waveguide 28's inner surface 32. As has been mentioned, "high-density" analytes 52 are those that are denser than the fluid that contains them, such as sample fluid 55, for example.

When it is said that cup 10 centrifugally-concentrates high-density analytes 52 onto inner surfaces 32 or 74 it is understood that at the end of this process some, or all, of them may be near to, partially or wholly on, or partially or wholly embedded in, inner surfaces 32 or 74.

Such centrifugal-concentration of high-density analytes 52 may be done by rapidly spinning cup 10 on its A-axis, which subjects sample fluid 55 and any analytes 52 that it may contain to substantial centrifugal forces. As a result, any high-density analytes 52 will to be driven towards waveguide 28, and eventually onto inner surfaces 32 or 74.

In other words, the radially-outwardly directed centrifugal force imparted by the spinning cup 10 on any high-density analytes 52 will give them a radially-outwardly directed sedimentation velocity that will imprint onto their random Brownian motion, thereby significantly enhancing the flux of high-density analytes 52 being driven towards, and eventually onto, inner surfaces 32 or 74.

For example, let it be assumed that sample fluid 55 comprises water (which has a density of 1.00 g/cc) and that the analytes 52 are a particular kind of bacteria, virus or protein. Since bacteria on average have a density of 1.05 g/cc to 1.10 g/cc, while viruses and proteins have densities in the range of 1.30 g/cc to 1.40 g/cc, it is apparent that bacteria, viruses and proteins would be high-density analytes 52. As a result, a radially-outwardly directed sedimentation velocity will be imparted to these high-density analytes 52 by the centrifugal forces generated by the spinning cup 10, thereby significantly enhancing the flux of high-density analytes 52 that are driven towards, and eventually onto, inner surfaces 32 or 74. It is fortunate that virtually all proteins, viruses and bacteria of interest are denser than water.

In general, when sample fluid 55 is inside the interior volume 68 of a hollow cylinder such as cup 10, the radially-outwardly directed sedimentation velocity for high-density analytes 52 may be readily developed by equating viscous drag to the applied centrifugal force. The time t required to transfer the analytes 52 from cup 10's interior volume 68, and onto inner surfaces 32 or 74, can be shown to be:

$$t = \frac{\frac{9}{2} u \ln(\eta)}{(\rho_p - \rho_f)(r_p \omega)^2} \quad \text{Equation 7}$$

In the above Equation 7, u is the viscosity of sample fluid 55; q is the ratio of the length of a radius measured from cup 10's A-axis to inner surface 72 of sample fluid 55 in spinning cup 10, to the length of a second radius measured from cup 10's A-axis to inner surfaces 32 or 74; $\rho_p$ is the density of the analytes 52 in sample fluid 55; $\rho_f$ is the density of sample fluid 55; $r_p$ is the radius of the analytes 52; and ω is the angular spin rate of cup 10 in radians/sec.

Since centrifugal force at cup 10's A-axis is zero, above Equation 7 correctly shows it would take an infinite time to collect all analytes 52 from sample fluid 55 if cup 10 was completely full of sample fluid 55. However, since sample fluid 55 may preferably form an annular cylinder in cup 10 while it is spinning, this is not an issue since none of sample fluid 55 need be located on its A-axis while cup 10 is spinning if cup 10 is not initially completely filled with sample fluid 55.

The average impingement rate of the analytes 52 at inner surfaces 32 or 74 can be estimated by dividing the number of individual analytes 52 initially within sample fluid 55 by the surface area of inner surfaces 32 or 74 and the time t required to transfer the analytes 52 from cup 10's interior volume 68 onto inner surfaces 32 or 74.

Figure 11:
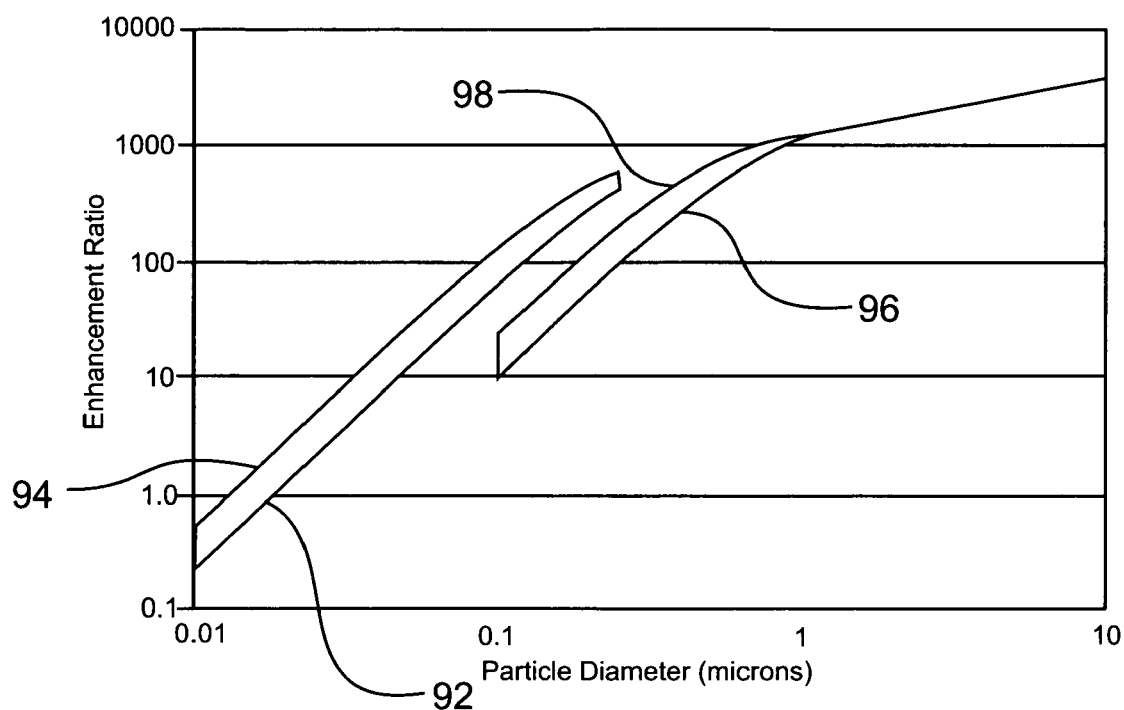
FIG. 11 shows a graph depicting various theoretical average impingement enhancement ratios versus the diameter of various analytes, for various analytes impinging onto the inner surface of the optical assay cup's waveguide due to centrifugal-concentration of the analytes caused by rapidly spinning the cup.
Figure 12:
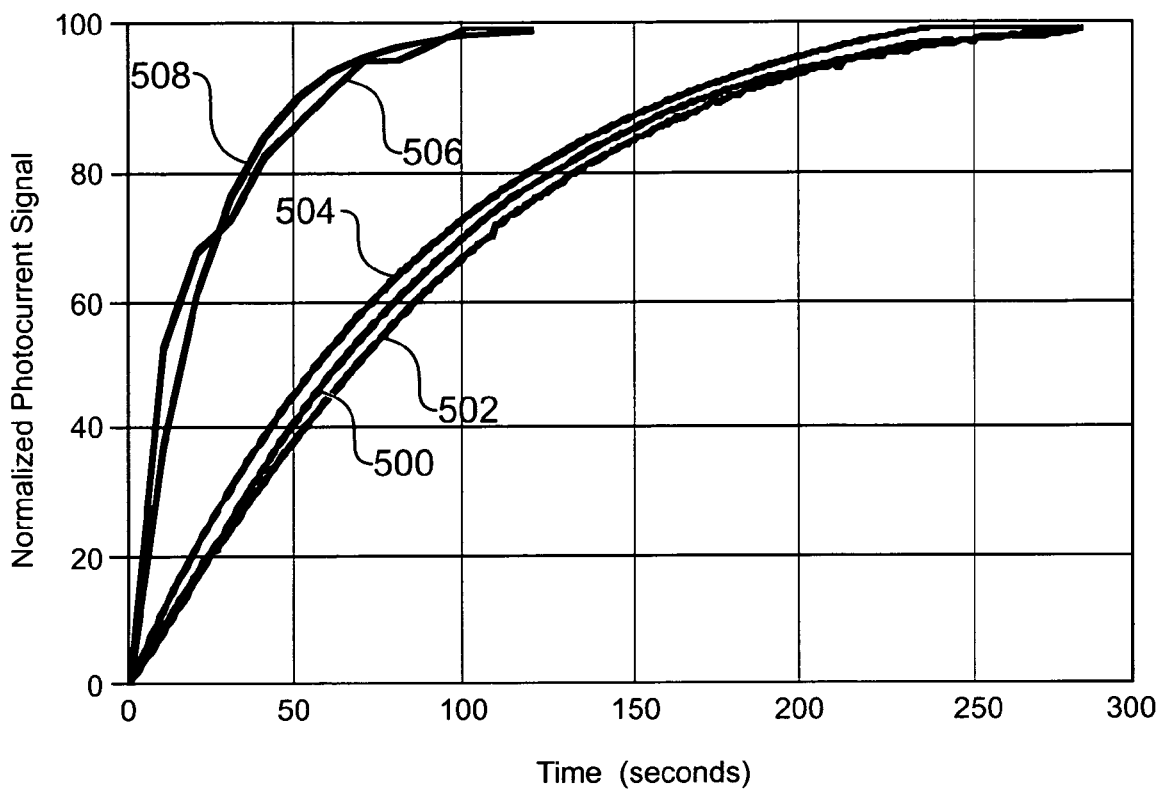
FIG. 12 shows a graph depicting various normalized photocurrent electrical output signals generated by a detector for different kinds of analytes versus spin time for the optical assay cup.
Figure 13:
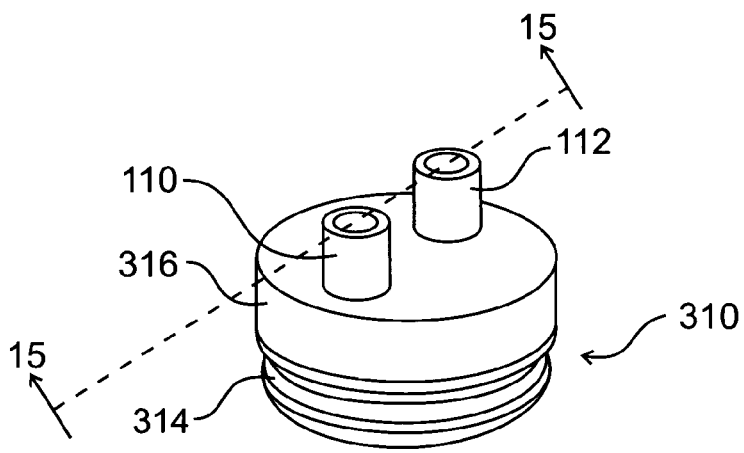
FIG. 13 is a diagrammatic perspective view of another embodiment of the optical assay cup of the present invention, and of another embodiment of its cover.

The ratio of the average impingement rate of the analytes 52 on inner surfaces 32 or 74 with cup 10 spinning, to the average impingement rate due solely to Brownian motion when it is not spinning (i.e., the impingement enhancement ratio), is illustrated in FIG. 11 for both viral and bacterial analytes 52.

In FIG. 11, the curves 92, 96 are the impingement enhancement ratios for viral and bacterial analytes 52, respectively, when cup 10 is spun at 12,000 rpm for 5 minutes; while the curves 94, 98 are the impingement enhancement ratios for viral and bacterial analytes 52, respectively, when cup 10 is spun at 18,000 rpm for 5 minutes. To make the calculations for FIG. 11 it was also assumed that cup 10 had an inner radius of 1.5 cm, that sample fluid 55 was water with a density of 1.00 g/cc, that the bacterial analytes 52 had a density of 1.05 g/cc, and that the viral analytes 52 had a density of 1.33 g/cc.

The curves 96, 98 in FIG. 11 show that the average impingement rates for bacterial analytes 52 with spinning may be as much as 1,000 times higher than possible with Brownian motion diffusion alone. This is an extremely large improvement because a Brownian motion diffusion-limited assay for bacterial analytes 52 in sample fluid 55 that had, for example, a detection limit of 1000 CFU (colony forming units)/ml when cup 10 was not being spun, may exhibit a detection limit in the range of as low as 1 CFU/ml when cup 10 was being rapidly spun—a most dramatic improvement indeed.

Similarly, the curves 92, 94 in FIG. 11 show that the average impingement rates for viral analytes 52 may be as much as about 500 times higher than possible with Brownian motion diffusion of viral analytes 52. This improvement is less than the corresponding improvement for bacterial analytes 52 because Brownian motion diffusive transport becomes increasingly effective as particle size decreases, and viral analytes 52 are generally much smaller than bacterial analytes 52.

However, even a two- or three-fold increase in an average impingement rate for any analyte 52 is significant, since it may be advantageously used to shorten overall assay time or to increase assay sensitivity if assay time is not shortened. In addition, whereas Brownian motion is random, the sedimentation forces created through spinning the cup 10 cause high density analytes 52 to spend an increased amount of time in contact with the inner surfaces 32 or 74, which may increase the probability of an attachment reaction occurring between the analytes 52 and the detection layer 51*b*.

Turning now to FIG. 12, the curves 500, 502, 504, 506 and 508 are plots of various normalized photocurrent electrical output signals generated by detector 60 as a function of signal light 58 emitted from waveguide 28's outer surface 34 as a function of various analytes 52 in sample fluid 55, versus spin time for cup 10. For this experiment, interrogation light 24 was produced by a Sanyo (Norwood, N.J.) solid-state 5 mW laser emitting at a wavelength of 635 nm, while detector 60 comprised an optoelectronic receiver incorporating a rejection filter for the interrogation light 24, and an uncooled type S1223 PIN-type photodetector, manufactured by Hamamatsu Corporation of Bridgewater, N.J. Cup 10 had an inner radius of 1.5 cm and was spun at 12,000 rpm.

Fluorescent compound-labeled simulant beads having a diameter of 1.1 microns and a density of 1.05 g/cc were used as simulants for bacterial analytes 52. Curves and 500 and 502 are for such fluorescent compound-labeled simulant beads having concentrations of 10,000 beads and 1,000,000 beads per cc of sample fluid 55 in cup 10, respectively.

Curve 506 is for the case that the analytes 52 were fluorescent compound-labeled *E. Coli* O157:H7 bacteria, having a concentration of about 100,000 bacteria per cc of sample fluid 55.

As seen in FIG. 12, the collection rate of the fluorescent compound-labeled labeled *E. Coli* O157:H7 bacteria at inner surfaces 32 or 74 is much faster than for the simulant beads for the bacterial analytes 52, probably due to the bacteria having a higher density and/or a larger effective size than the simulant beads. If it is assumed that the bacteria had a density that was the same 1.05 g/cc as the simulant beads, then the implied effective diameter of the bacteria was about 2.1 microns.

Curves 504 and 508 are theoretical curves that were generated by substituting physical property data for the fluorescent compound-labeled simulant beads and *E. Coli* O157:H7 bacteria, respectively, into the following equation:

$$\text{Surface density}=0.5C_0R_{id}(1-e^{-\alpha t}) \quad \text{Equation 8}$$

where $C_0$ is the initial volumetric particulate density of the analytes 52 in sample fluid 55 in cup 10; $R_{id}$ is the internal radius of cup 10; and t is the spin time for cup 10.

In above Equation 8 $\alpha$ is a constant that is determined by the following Equation 9:

$$\alpha=\left(\frac{4}{9}\right)\left[\frac{\rho_p-\rho_f}{u}\right](r_p\omega)^2 \quad \text{Equation 9}$$

In the above Equation 9 $\rho_p$ is the density of the analytes 52 in sample fluid 55; $\rho_f$ is the density of sample fluid 55; u is the viscosity of sample fluid 55; $r_p$ is the effective radius of the individual analytes 52; and $\omega$ is the angular spin rate of cup 10 measured in radians/sec. As seen in FIG. 12, theoretical curves 504 and 508 predict sedimentation of the simulant beads and the *E. Coli* bacteria from sample fluid 55 onto inner surfaces 32 or 74 very well.

The curves 502, 504, 506 and 508 of FIG. 12 also show that essentially all of the analytes 52 in sample fluid 55 are moved onto or adjacent to inner surfaces 32 or 74 after cup 10 has been spun at 12,000 rpm for four to five minutes. Effective concentrations of the analytes 52 near to, or on, inner surfaces 32 or 74 are extremely high at this point even though a dynamic equilibrium condition occurs in which the flux of analytes 52 moving towards the inner surfaces 32 or 74 by centrifugal sedimentation is equal to the flux of analytes 52 moving away from the inner surfaces 32 or 74 through diffusion. For one-micron diameter analytes 52 subjected to this dynamic equilibrium condition, it can be shown that their effective concentration immediately adjacent to inner surfaces 32 or 74 is about $10^6$ times higher than their initial concentration in sample fluid 55. This augurs well for desirable, large reaction rates between the analytes 52 and any capture media on the inner surface 74 of detection layer 51*b*.

Accordingly, spin concentration of high-density analytes 52 onto inner surfaces 32 or 74 may desirably result in much higher levels of signal light 58 being emitted from waveguide 28's outer surface 34 as a function of the analytes 52 that may be present in cup 10's interior volume 68 than would otherwise be the case. This is because, in general, the higher the concentration of the analytes 52 on inner surfaces 32 or 74, the higher the corresponding level of signal light 58. This higher level of signal light 58 may desirably result in quicker, more sensitive, and more accurate measurements of the analytes 52.

Rapidly spinning cup 10 may also have the desirable effect of causing low-density debris (i.e., debris that is less dense than the fluid in cup 10, such as sample fluid 55), to move away from inner surfaces 32 or 74, and towards inner surface 72 of fluid layer 51*c*. This may be desirable because it may tend to reduce measurement inaccuracies that might otherwise be caused by any low-density debris that was near to, or on, inner surfaces 32 or 74. Lipids may be an example of low-density debris.

Rapidly spinning cup 10 may also have the desirable effect of causing debris that is more dense than sample fluid 55 in cup 10, but less dense than the analytes 52, to move towards inner surfaces 32 or 74 less quickly than the analytes 52, which will tend to result in the analytes 52 being centrifugally-concentrated towards, and eventually onto, inner surfaces 32 or 74 more quickly than such debris.

As indicated above, improvements on the order of up to 1,000 times, or more, in the levels of signal light 58 are easily attained by centrifugal-concentration of the analytes 52 towards, and eventually onto, inner surfaces 32 or 74, as compared to if no such centrifugal-concentration was performed.

In any event, cup 10 may be spun at any desired rpm, for any desired length of time, depending on such factors as, for example, the needs of the user, the particular sample fluid 55, the particular kind of analytes 52 in sample fluid 55, the nature of any particular impurities or debris in sample fluid 55, and the quickness, sensitivity or accuracy of the desired measurements. For example, cup 10 may be spun up to 20,000 rpm, or more, for times ranging from a few seconds, or less, to a few hours, or more. In addition, cup 10 may be spun at various rpm's, for various lengths of time, according to the needs of the user.

For very small analytes 52, such as most toxins or proteins, the sedimentation time from Equation 7 is very long even if such analytes 52 are much denser than sample fluid 55. Accordingly, spinning cup 10 will tend to centrifugally-concentrate them onto inner surfaces 32 or 74 more slowly than would be the case with larger analytes 52 of the same density. In any event, spinning cup 10 will not negatively impact any assays directed towards such very small analytes 52, so that cup 10 may still be a high performance sensor for detecting even very small analytes 52, due to the Brownian motion diffusion of these very small analytes 52 and the relatively large detection surface area of inner surfaces 32 or 74.

For analytes 52 of any size, any suitable apparatus or methods may be used to help ensure that most, if not all, of the analytes 52 in sample fluid 55 come into contact with inner surfaces 32 or 74. For example, sample fluid 55 may be stirred or circulated within cup 10 in any suitable way such as, for example, by spinning cup 10 at various rotational velocities for various periods of time, by periodically reversing the direction in which cup 10 is spun, by providing internal stirring vanes within cup 10, or by agitating cup 10. This increases the statistical probability that suspended analytes 52 in sample fluid 55 will contact inner surfaces 32 or 74, and reduces the thickness of mass-transfer boundary layers at inner surfaces 32 or 74 that might otherwise tend to shield surfaces 32 or 74 from intimate contact with suspended analytes 52.

If desired by the user, any suitable way may be used for increasing the effective size of any particular analytes 52, so that they effectively become larger analytes 52, such as by employing any suitable microbeads to capture the analytes 52, for example. Suitable microbeads may be, for example, latex microbeads that have capture antibodies for the analytes 52 immobilized on their surfaces. Various inorganic microparticles or nano-particles such as CdS quantum dots may also serve this purpose while simultaneously providing a strong fluorescent indicator 77 for the analytes 52.

Detectors 60, 60a, 60b, 60c, 460

It is understood that detectors 60 (FIGS. 1-3), 60a (FIG. 17), 60b (FIG. 18), 60c (FIG. 18a), and 460 (FIG. 6) described herein are the same as each other, or are at least similar to each other, in any particular respect such as with respect to their respective mountings, locations, quantities (how many), sizes, shapes, designs, materials, compositions, constructions, manufactures, physical properties, dimensions, specifications, variations, operations, methods, and uses, except for those differences which will be made apparent by all of the disclosures herein. Any of detectors 60, 60a, 60b, 60c and 460 may be used with any of the cups 10, 210, 210a, 310, 410 disclosed herein.

Regardless of the size or density of the analytes 52, cup 10 may be spun while taking measurements of the analytes 52, so that part, or all, of cup 10's interior volume 68 (e.g., inner surfaces 32 or 74, or the analytes 52) will be interrogated by evanescent or darkfield interrogation light 24a, 24b; and so that detector 60 may take measurements of signal light 58 being emitted by part, or all, of waveguide 28's outer surface 34 as a function of, for example, the presence, quantity, number, or at least one targeted distinguishing characteristic of any analytes 52 that may be present in the interior volume 68.

Detector 60 seen in FIGS. 1-3 may produce electrical output signals as a function of signal light 58 it receives; and may comprise any suitable light collecting optical lens assembly, any suitable optical filters to select the wavebands of signal light 58 to be detected and the wavebands of non-signal light to be attenuated, and any suitable solid-state photodetector such as a PIN photodiode or a linear CCD (Charge Coupled Device) array detector, or a photomultiplier device.

Figure 17:
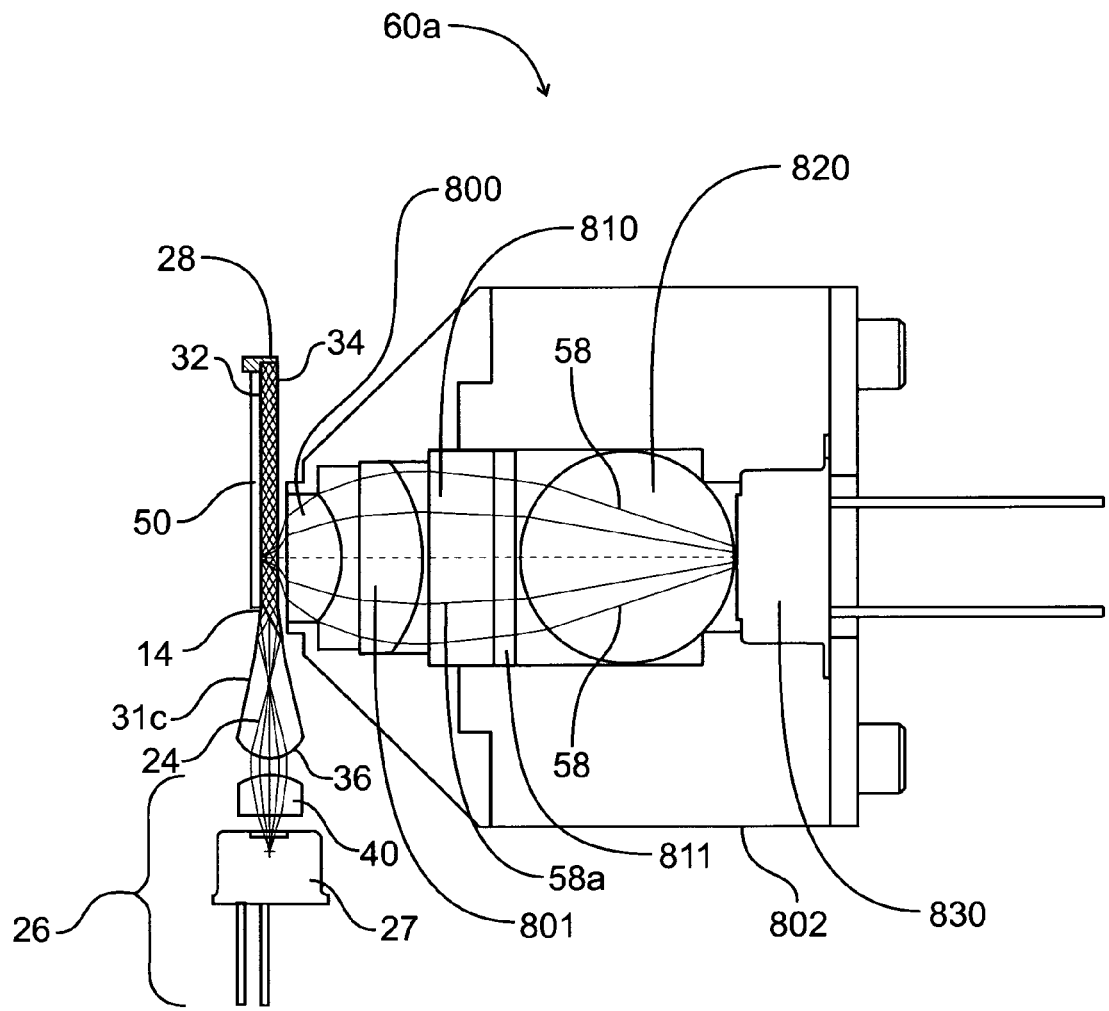
FIG. 17 is a diagrammatic, side elevational view, partly in cross section, of one type of signal light detector being used with the optical assay cup of FIG. 1.

The detector 60a embodiment shown in FIG. 17 is representative of a high numerical aperture compound lens design that may be used when signal light 58 comprises fluorescent emissions. Detector 60a includes light collecting lenses 800 and 801, optical filters 810 and 811, a focusing lens 820, and a photodetector 830.

The light received by the detector 60a may comprise signal light 58, and may also comprise non-signal light, such as scattered interrogation light 24, 24a, 24b or ambient light from the environment. Such non-signal light may interfere with the accurate detection of signal light 58 by detector 60a.

Accordingly, in many cases it is desirable for the detector 60a to include suitable filter(s), such as thin-film interference band-pass or long-pass filters, for example, to attenuate any non-signal light that it receives. Interference filters usually require that the non-signal light pass through the filter at a particular angle, usually perpendicular to the filter face, and that deviations from the design angle be kept to within perhaps plus or minus 10 to 20 degrees.

Thus, when interference filters are used, detector 60a may comprise any suitable optical means for collimating any non-signal signal light, such as plano-convex lenses 800 and 801, for example. Of course, the lenses 800, 801 will also collimate the signal light 58.

The beam of non-signal light and signal light 58a from the lenses 800, 801 may be then passed through any suitable filter means for attenuating the non-signal light, such as any suitable sharp-cut absorbing filter 810 and any suitable long-pass interference filter 811. As a non-limiting example, let it be assumed that the non-signal light is some of the interrogation light 24, 24a, 24b, which is 635 nm light from a laser diode, while the signal light 58 is fluorescent signal light 58 having a peak emission wavelength in the 650 nm to 700 nm waveband.

In this case, since the non-signal light has a wavelength of 635 nm, the interference filter 811 may be a custom long pass design with its 50% transmission preferably occurring within the range of 640 nm to 660 nm. The absorbing filter 810 may be selected to strongly absorb at the wavelengths of the non-signal light, while having little, or no, absorption at the wavelengths of the signal light 58. An absorbing filter 810 is included in the 60a optical design to attenuate any non-signal light that enters at large skew angles relative to detector 60's optical axis, while the interference filter 811 is very effective at rejecting collimated non-signal light that is outside of its pass band. However, both filters 810, 811 pass most, if not all, of signal light 58, which may then be focused onto any suitable photodetector 830 in any suitable way, such as by using a high index of refraction glass or sapphire lens 820. The photodetector may be, for example, a type S1223 PIN photodetector manufactured by Hamamatsu Corporation of Bridgewater, N.J. All of the forgoing components of detector 60a may be mounted in any suitable housing 802 in any suitable way.

Figures 18, 18A:
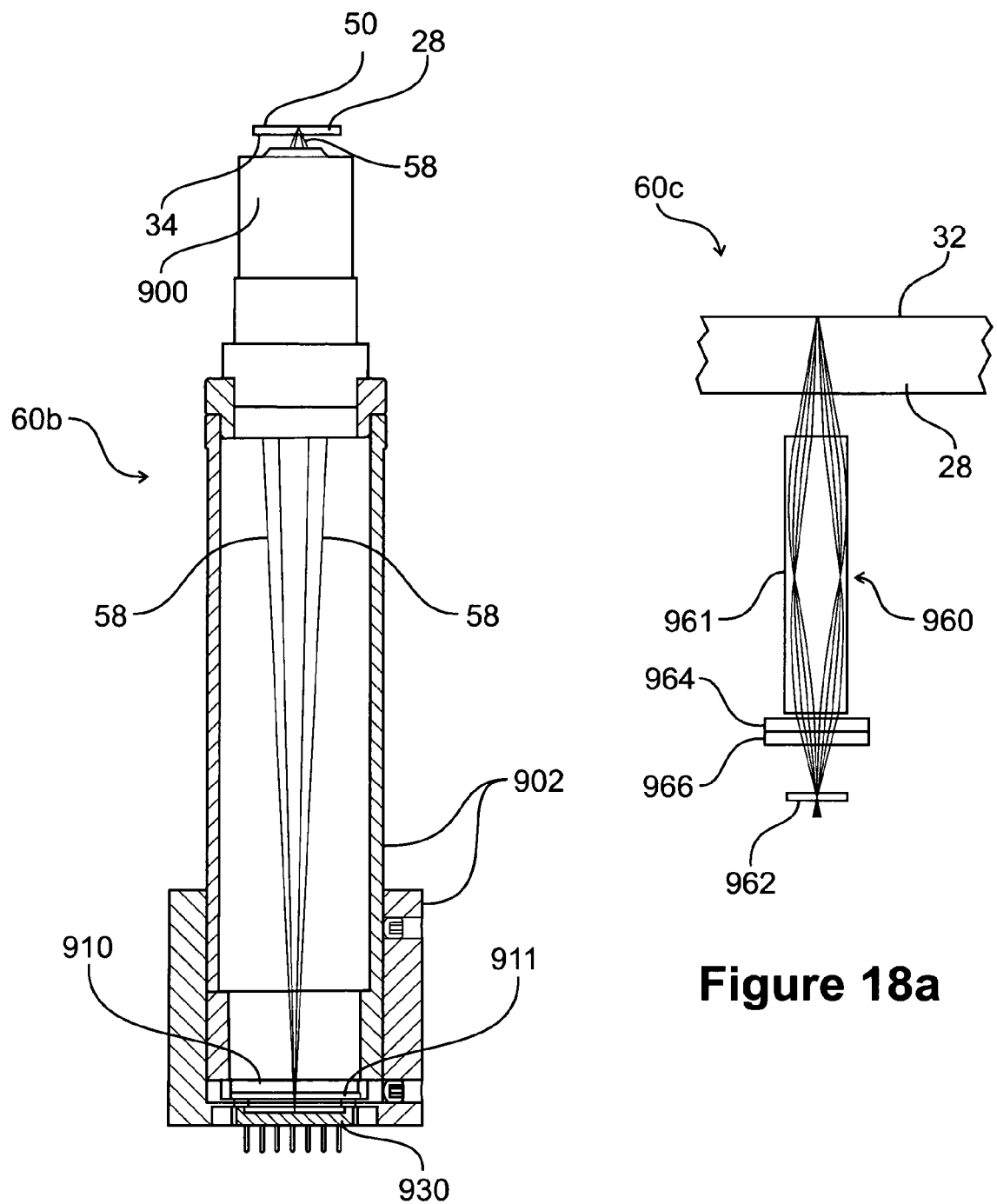
FIG. 18 is a diagrammatic, side elevational view, partly in cross section, of an array-style signal light detector being used with the optical assay cup of FIG. 1.
FIG. 18a is a diagrammatic, perspective view of a second array-style signal light detector being used with the optical assay cup of FIG. 1.

Turning now to FIG. 18, detector 60b may, for example, enable the user to detect individual analytes 52, such as individual bacteria or spores; or to monitor highly detailed patterns of capture agents bound to non-fluid detection layers 51a, 51b, or to waveguide 28's inner surface 32.

Detector 60b may comprise any suitable high magnification device, such as a microscope objective lens 900, and any suitable photodetector, such as a photodiode array 930. If the assay method involves visualization of fluorescent compound-labeled analytes 52, filters 910 and 911 (equivalent in function to filters 810 and 811, respectively) may be placed in signal light 58's path to attenuate any accompanying non-signal light, such as scattered interrogation light 24, 24a, 24b. Since the objective lens 900 is a high magnification device, it may also serve the functions of focusing signal light 58 and any non-signal light from waveguide 28's outer surface 34 onto the filters 910, 911 (which attenuate the non-signal light), and of focusing the signal light 58 onto the photodiode array 930. All of the forgoing components of detector 60b may be mounted in any suitable housing 902 in any suitable way.

By way of example, the lens 900 may be a 20× objective sold by Edmund Scientific of Barrington, N.J., while the photodiode array 930 may be a 256×1 sensor array manufactured by Taos Inc. of Plano, Tex. The diode-to-diode spacing of this array 930 is 63.5 microns and its array width is 55.5 microns. Such a lens 900 and array 930 together create a physical resolution of about 3.2 microns over a 0.81 mm wide observation area on non-fluid detection layers 51a, 51b, or on waveguide 28's inner surface 32.

A possible disadvantage of detectors 60a, 60b is the comparatively small observation area provided on non-fluid detection layers 51a, 51b, or on waveguide 28's inner surface 32. To solve this problem, the detector 60c shown in FIG. 18a may provide a comparatively large observation area on non-fluid detection layers 51a, 51b, or on waveguide 28's inner surface 32.

Detector 60c may include any suitable light collecting and imaging means such as a linear lens array 960; and may further comprise any suitable photodetector 962, such as a linear photodiode array 962. The linear lens array 960 may be selected to provide a high-resolution image of a narrow circumferential section of non-fluid detection layers 51a, 51b, or of waveguide 28's inner surface 32; wherein the circumferential section may be of any selected axial length, up to the full axial length of non-fluid detection layers 51a, 51b, or of waveguide 28's inner surface 32.

The lens array 960 may comprise any suitable lenses, such as the rod-like lenses 961 illustrated in FIG. 18a. The lenses 961 may be of any suitable type, such as GRIN lenses having a radial refractive index profile. GRIN lens arrays are attractive because of their compact size and low cost. By using larger arrays of GRIN lenses, light gathering power may be improved at some reduction in image quality. The GRIN lenses 961 may have any suitable lens length, such as from about 0.5 to about 1.0 pitch, a term familiar to those in the art, in order to provide a continuous non-inverted 1:1 image on the linear photodiode array 962 of a narrow circumferential section of non-fluid detection layers 51a, 51b, or of waveguide 28's inner surface 32, wherein the circumferential section may be of any selected axial length, up to the full axial length of non-fluid detection layers 51a, 51b, or of waveguide 28's inner surface 32.

Detector 60c may further comprise any suitable filter(s) for attenuating any non-signal light (such as scattered interrogation light 24, 24a, 24b), and for passing signal light 58. The filters may comprise, for example, a long-pass absorbing filter 964 and an interference filter 966, which may be like the filters 810 and 811, respectively, of detector 60a. In general, absorbing filters may be more effective in attenuating non-signal light than interference filters, due to the wide range of angles the rays comprising the non-signal light may have with respect to the detector 60c's optical axis when they reach the filters 964, 966.

Additional light gathering power may be provided for detector 60c by selecting a design for its optical array 960 that creates an inverted image. This is because in such designs, which may use either conventional or GRIN lenses, the lenses will typically be much closer to the non-fluid detection layers 51a, 51b, or to waveguide 28's inner surface 32, so that more light will be gathered by its optical array 960.

While the images from adjacent lenses in such an optical array 960 will not constructively combine, this may not be an issue when either evanescent or darkfield interrogation is used. This is because one basic goal of the present invention may be to simply detect the presence (or absence) of signal light 58 emitted by the analytes 52, such as when they have been labeled with fluorescent indicators 77.

Since background, non-signal light levels will be low, signal light 58 emitted by analytes 52 will appear as small bright spots on a black background. Each analyte 52 will be detected, but its image position will be inverted. Since most simple lenses show a significant drop-off in resolution when imaged objects are spaced more than about ½ to ¾ of a lens radius from the lens axis, it may be desirable to use two adjacent lens arrays 960 and photodiode arrays 962 to provide an interlaced line scan of up to the full length of non-fluid detection layers 51a, 51b, or of waveguide 28's inner surface 32. In such a design, each lens is tasked with only imaging objects appearing within ½ of a lens radius from the lens axis, and individual lenses in the two adjacent lens arrays 960 are offset by one lens radius from each other. By merging the two line scans, a detailed image of up to the entire length of non-fluid detection layers 51a, 51b, or of waveguide 28's inner surface 32 may thereby be provided.

For any detector 60, 60a, 60b, 60c, the spatial resolving of a source of signal light 58 on non-fluid detection layers 51a, 51b, or on waveguide 28's inner surface 32 will be determined by the resolution of its lenses (e.g., lens array 960 in detector 60c), by the characteristics of spinning apparatus 25 used to spin cup 10, and by the physical size and sensitivity of its photodetector elements (e.g., photodiode array 962 in detector 60c). By combining other light sources 26; detectors 60, 60a, 60b, 60c; and spinning apparatus 25, a wide range of resolution capabilities can be obtained for the optical assay apparatus 11.

For any detector 60, 60a, 60b, 60c, 460 it may not be necessary for the detector to have an optical resolution comparable to that of the size of the analytes 52, as long as signal light 58 associated with an individual analyte 52, or with a colony or other cluster of analytes 52, is detectable, such as by being an anomaly relative to the background level of signal light 58 in the vicinity of the analytes 52 being detected.

In addition, if the number of individual analytes 52 clustered within the detection area of a particular pixel of the detector's photodetector (e.g., photodiode array 962 of detector 60c) is not too large, and if the amount of signal light 58 emitted as a function of an individual analyte 52 is known, it may even be possible to estimate the number of individual analytes 52 residing within the particular optical region observed by that particular pixel. This may be done by dividing the total signal light 58 received by that particular pixel by the known amount of signal light 58 emitted as a function of an individual analyte 52.

Figure 19:
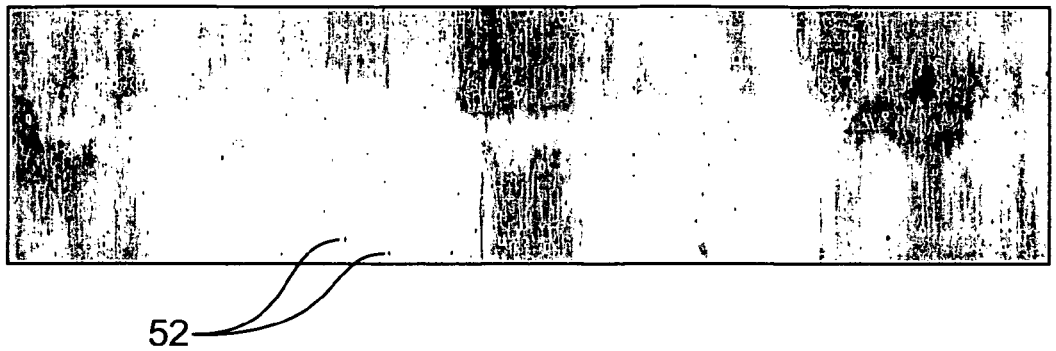
FIGS. 19 and 20 show the detection of individual micron-size analytes.
Figure 20:
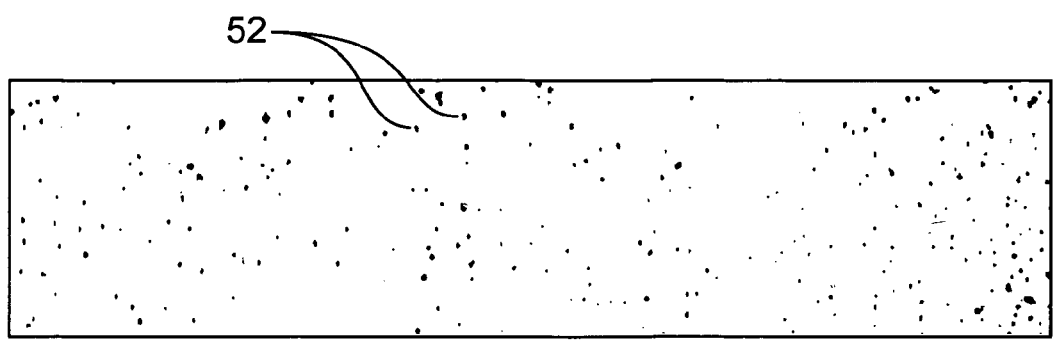

Examples of the results of tests for the detection of individual analytes 52 are shown in FIGS. 19-20. For these tests, fluorescent analytes 52 of 1.1 micron diameter (FIG. 19) and 10 microns diameter (FIG. 20) were bound to inner surface 32 of a 1.5 mm thick waveguide 28 of a cup 10 having a 3.6 cm internal diameter.

While cup 10 was rotated, its interior volume 68 was subjected to both evanescent and darkfield interrogation from a 2.5 mW laser diode light emitter 27 operating at 635 nm. Simultaneously, signal light 58 emitted from waveguide 28's outer surface 34 was imaged by a detector 60b having a 256×1 photodiode array 930 using a 20× objective lens 900 as shown in FIG. 18. The calculated resolution for detector 60b per pixel of the photodiode array 930 for this test sequence was 3.2×4 microns, yet individual 1-micron fluorescent analytes 52 were easily detected.

This is particularly remarkable since cup 10 was operated with its interior volume 68 filled with dry air. As a result, darkfield interrogation rays 24a could only pass through waveguide 28's inner surface 32 and into the analytes 52 through near-field coupling processes, which are expected to be much less efficient at exciting fluorescence related to the analytes 52 than if the analytes 52 had been coupled to the inner surface 32 through a fillet or thin film of water 76.

Turning again to detector 60, although only one detector 60 is illustrated in FIGS. 1-3, more than one detector 60 may be provided. Providing more than one detector 60 may be desirable since multiple detectors 60 may permit the simultaneous detection of more than one kind of analyte 52, the simultaneous detection of more than one targeted distinguishing characteristic of the same kind of analyte 52 during the use of cup 10, or a higher resolution image of non-fluid detection layers 51a, 51b, or of waveguide 28's inner surface 32.

For both high-density and low-density analytes 52, as cup 10 is rotating detector 60 may perform drum-style imaging of signal light 58 emitted from waveguide 28's outer surface 34 as a function of any analytes 52 that may be present in cup 10's interior volume 68. The electrical output signals from detector 60 may be used to effectively produce a high-resolution, two-dimensional optical image of those analytes 52 attached or adjacent to non-fluid detection layers 51a, 51b, or waveguide 28's inner surface 32, particularly if detector 60's photodetector is of a linear array type.

Orienting detector 60 perpendicular to outer surface 34, as seen in FIGS. 1-3, may also have the desirable advantage of reducing any adverse effects that might otherwise be caused by any scattering of interrogation light 24, 24a, 24b due to any defects or imperfections in waveguide 28 or detection coating 50. This is because such defects will typically have their lowest emission rates of scattered interrogation light 24, 24a, 24b perpendicular to waveguide 28's outer surface 34, and thus such scattered light 24, 24a, 24b will be less likely to enter a perpendicularly oriented detector 60.

It may be desirable for detector 60 to receive signal light 58 emitted from waveguide 28's entire outer surface 34 in one rotation of cup 10. Recorded images produced from detector 60's electrical output signals may be further refined by additional rotations of cup 10 to average background noise and detector 60's electrical output signals. In addition, by comparing detector 60's electrical output signals over a number of rotations of cup 10, metabolic activity or growth of the analytes 52 may be detected.

For certain types of assay methods in which the amount of signal light 58 increases over time during the course of the assay, monitoring of waveguide's 28's outer surface 34 by detector 60 over a number of rotations of cup 10 may also allow detection of low concentrations of the analytes 52. This is because as time passes during the course of the assay, an increasing number of the analytes 52 will become associated with whatever indicator 77 is being used in that particular assay, resulting in corresponding changes in signal light 58 over time. Indicators 77 are discussed below in more detail.

For example, in an ELISA (discussed below in more detail), the enzymatic production of an indicator 77 as a function of the analytes 52 in cup 10 produces an increasing amount of signal light 58 over time. Similarly, in an assay that involves the use of nucleic acid amplification, such as a nucleic acid assay incorporating a polymerase chain reaction (discussed below in more detail), there may also be an increasing amount of signal light 58 produced over time, due to increasing numbers of an indicator 77 produced as a function of the analytes 52 in cup 10. Accordingly either of the above assays allows the analytes 52 to be accurately detected above background noise by using detector 60 to monitor signal light 58 for a number of rotations of cup 10.

Digital image processing requirements for a detector 60 having an array type photodetector do not push the current state-of-the-art. For example, in order for a 3.2 cm inside diameter cup 10 to be monochrome scanned with a 4-micron circumferential resolution using a 256-element array type photodetector, a data file equivalent to a 6.4 mega pixel digital image would be created. High-end digital cameras now feature a capability of images having a data file of more than 16 megapixels. From this it can be concluded that manipulation of the data files produced by detector 60 to identify what quantity or number of the analytes 52 are present in cup 10 should be easily possible with state-of-the-art digital electronics.

As an alternative to using detector 60 to take measurements of signal light 58 being emitted from waveguide 28's outer surface 34 while cup 10 is spinning, such measurements may also be taken while cup 10 is not spinning.

As a further alternative, such measurements may be taken while relative motion between light source 26 and waveguide 28 is provided in any suitable way other than by spinning cup 10. For example, cup 10 may be allowed to be stationary and light source 26 and detector 60 rotated with respect to cup 10. This may be possible if light source 26 and detector 60 are mounted, for example, in a fixed relationship relative to each other on a rotating stage that has the same axis of rotation as cup 10. In this manner light source 26 can focus interrogation light 24 into proximal edge 36 of cup 10's sidewall 14 as light source 26 moves along its respective circular path while detector 60 is also in a proper position to receive signal light 58 being emitted from waveguide 28's outer surface 34 as detector 60 moves along its respective circular path.

Indicator 77

As used herein, the term "indicator" (e.g., indicator 77), means any suitable substance that may be detected by virtue of any property of signal light 58 that it emits, or doesn't emit, as a function of the presence, quantity, number, or at least one targeted distinguishing characteristic of the analytes 52 when it is interrogated by evanescent or darkfield interrogation light 24a, 24b. Indicator 77 may comprise, for example, any suitable element, molecular moiety, nanoparticle, nanosphere, nanorod, liquid crystal molecule, colored micro sphere, or a color-changing microorganism (such as a virus or bacterium).

By way of nonlimiting example, indicator 77 may cause: (a) an increase or decrease in the amount of fluorescent or luminescent signal light 58 (i.e., a fluorescent indicator 77 or a luminescent indicator 77, respectively), (b) an increase or decrease in the amount of signal light 58 comprising evanescent or darkfield interrogation light 24a, 24b, due to indicator 77's absorption, reflection, refraction or scattering of the interrogation light 24a or 24b over a portion or the entirety of the spectrum of interrogation light 24a or 24b; (c) an increase or decrease in the amount of signal light 58 due to a change in indicator 77's index of refraction; (d) a change in the intensity or direction of scattered light 24a or 24b that comprises signal light 58; (e) a change in the polarization of light 24a or 24b that comprises signal light 58; (f) a change in the Raman spectrum of signal light 58; (g) a phase shift between light 24a or 24b and signal light 58; or (h) any other change in any property of signal light 58 that is optically detectable in any suitable way.

Interrogation of Detection Coating 50 and Analytes 52

Referring now to FIGS. 1-3 and 5, the optical assay cup 10 may comprise a detection coating 50. Detection coating 50 may be omitted, for example, in a situation where at least some of the analytes 52 (or any particular indicator 77 for the analytes 52, see FIG. 5) are located near to or on waveguide 28's inner surface 32. In the event that the analytes 52 (or any particular indicator 77 for them) are located near to or on inner surface 32, they may be surrounded or covered, in whole or in part, by a fluid within cup 10, such as sample fluid 55, air, water, or any suitable reagent, for example. For simplicity, a cup 10 that does comprise a detection coating 50 will be discussed in some detail, because in view of all of the disclosures herein, a person of ordinary skill in the art to which the present invention is addressed would be able to easily apply those same or similar comments, as appropriate, to a cup 10 that does not comprise a detection coating 50, and to make and use such a cup 10 to detect any suitable analytes 52 within cup 10's interior volume 68.

It is recalled that, as set forth above, for simplicity of description herein, and by way of non-limiting example, it has been assumed that detection coating 50 comprises three detection layers 51a, 51b and 51c; that layers 51a and 51b are non-fluid detection layers; and that layer 51c is a fluid detection layer.

To use cup 10, the range of reflected angles $\theta_{0i}$ for interrogation light 24 from light source 26 (see FIG. 4) may be easily set so that detection coating 50 (e.g., layers 51a, 51b and 51c), and the analytes 52 may be interrogated by rays of interrogation light 24 for optimal contrast and visualization, by using either evanescent interrogation (by rays of evanescent interrogation light 24a) or by using darkfield interrogation (by rays of darkfield interrogation light 24b).

The range of reflected angles $\theta_{0i}$ may be set in any suitable way such as, for example, by suitably selecting the shape of one or both of the reflector 30's inner and outer reflective surfaces 31a, 31b; or by suitably selecting the positioning and orientation of the light source 26, reflector 30 or waveguide 28 with respect to each other.

A composite sensing waveguide 29 for evanescent and darkfield interrogation light 24a, 24b may be formed in any suitable way. For example, it may be formed by part or all of waveguide 28, detection coating 50, and one or more of detection coating 50's detection layers (e.g., layers 51a, 51b, 51c); either alone or in any suitable combination with each other.

In other words, such a sensing waveguide 29 may have an inner interface or a reflective inner surface that may be located at: (a) interface 70 between coating 50 or detection layer 51c and whatever is inside of cup 10's interior, such as air; (b) interface 67 between layer 51c and layer 51b; (c) interface 66 between layer 51b and layer 51a; or (d) interface 64 between layer 51a and waveguide 28.

In addition, such a sensing waveguide 29 may have an outer interface or a reflective outer surface that may be: (a) interface 34a between waveguide 28 and whatever is outside waveguide 28, such as air; (b) interface 64 between layer 51a and waveguide 28; (c) interface 66 between layer 51b and layer 51a; or (d) interface 67 between layer 51c and layer 51b.

Regardless of how the sensing waveguide 29 is formed, and regardless of which of the above interfaces and reflective surfaces it may have, the rays of evanescent and darkfield interrogation light 24a, 24b may propagate axially down the sensing waveguide 29 (i.e., in a direction parallel to cup 10'a A-Axis).

Evanescent Interrogation

Referring now to FIG. 5, evanescent interrogation light 24a for evanescent interrogation may be produced by selecting, in any suitable way, the reflected angle $\theta_{0i}$ for interrogation light 24 to be at, or near, but not exceed, the critical angle of the sensing waveguide 29's selected inner interface 64, 66, 67, or 70 that will be used to generate the desired evanescent electric field 56.

If an appropriate reflected angle $\theta_{0i}$ is chosen, total internal reflection of rays of evanescent interrogation light 24a will occur at sensing waveguide 29's selected inner interface 64, 66, 67, or 70.

By way of example, let it be assumed that interface 64 at waveguide 28's inner surface 32 is the selected inner interface and that an appropriate reflected angle $\theta_{0i}$ is chosen, so that total internal reflection of rays of evanescent interrogation light 24a within waveguide 28 at interface 64 will occur, as exemplified by the path of evanescent interrogation light ray 24a seen in FIG. 5 which may propagate axially down the sensing waveguide 29 (i.e., in a direction parallel to cup 10'a A-Axis). By way of further example, let it be assumed that waveguide 28 is made of polystyrene, that detection coating 50 (e.g., layers 51a, 51b and 51c) has a refractive index similar to that of water, and that evanescent interrogation light 24a has a wavelength of 635 nm. Under these conditions, an evanescent electric field 56 produced by evanescent interrogation light 24a penetrates into detection coating 50 about 0.10-0.20 microns, i.e., evanescent electric field 56 has a "skin depth" of about 0.10-0.20 microns, and an average "skin depth" of about 0.15 microns. Note that evanescent electric field 56 illustrated in FIG. 5 is not drawn to scale.

Let it be further assumed, by way of example, that the analytes 52 have been labeled in any suitable way with any suitable indicator 77, such as a light-absorbing compound or a fluorescent compound, which may reside near, on, or in, the analytes 52, in whole or in part. Then any such indicator 77-labeled analytes 52 which are located within the "skin depth" will interact with evanescent electric field 56.

If indicator 77 is a light-absorbing compound, a small loss in the transported optical power of the evanescent interrogation light 24a in waveguide 28 will occur due to the interaction of its evanescent electric field 56 with the light-absorbing compound, but there will be little change in signal light 58 seen by detector 60 if the layers 51a, 51b are optically transparent because there is no scattering or re-emission of evanescent interrogation light 24a. This means that evanescent interrogation is relatively ineffective in detecting analytes 52 that have been tagged with a light-absorbing indicator 77.

On the other hand, if indicator 77 is a fluorescent compound then fluorescent signal light 58 will be emitted from the portions of indicator 77-labeled analytes 52 which are within the "skin depth" of evanescent electric field 56 that is generated by evanescent interrogation light 24a. This fluorescent signal light 58 may then be detected by detector 60 in the manner disclosed herein. In such a situation, the amount of signal light 58 will be proportional to the number of indicator 77-labeled analytes 52 that are located wholly, or in part, within the "skin depth".

One of the important features of the present invention may be to select the thickness of detection coating 50 (e.g., the thickness of layers 51a, 51b and 51c) and the average "skin depth" of the evanescent electric field 56 so that the evanescent electric field 56 does not substantially penetrate beyond the selected inner interface 64, 66, 67, or 70, in order to avoid measurement errors that may be induced by foreign matter, such as debris, that may be present on, in, or above, the selected inner interface 64, 66, 67, or 70.

Alternatively, some penetration beyond the selected inner interface 64, 66, 67, or 70 may not be objectionable, as long as evanescent electric field 56 does not induce significant measurement errors, since the strength of evanescent electric field 56 decays rapidly as a function of distance from the selected inner interface 64, 66, 67, or 70.

Since the average "skin depth" of evanescent electric field 56 depends on such variables as the wavelength of evanescent interrogation light 24a and the respective refractive indices of waveguide 28 and detection coating 50 (e.g., layers 51a, 51b and 51c), the average "skin depth" may be varied at will, within reason, depending on the needs of the user of the present invention by suitably adjusting one or more of the applicable variables.

One possible limitation on the use of evanescent interrogation is where the analytes 52 have a thickness or diameter that is substantially greater than the average "skin depth" of evanescent electric field 56, which may result in only a small portion of the surface or volume of the analytes 52 being excited by evanescent electric field 56, even if the analytes 52 are in direct contact with the selected inner interface.

For example, let it be assumed that indicator 77 is a fluorescent compound, that indicator 77-labeled analytes 52 are bacteria having a diameter of 1 micron that are resting on the selected inner interface 64, 66, 67, or 70, and that the average "skin depth" of evanescent electric field 56 is 0.15 microns. In such a situation, then the fluorescent compounds on only about 15% of the surface, or in only about 6% of the volume of the 1 micron diameter analytes 52 will be excited by evanescent electric field 56 and emit fluorescent signal light 58. As a result, the total amount of signal light 58 emitted by indicator 77-labeled analytes 52 when subjected to evanescent interrogation may be too small for useful measurement purposes, depending on such factors as the sensitivity of detector 60, for example. Signal light 58 levels may also be too low if intervening layers in detection coating 50 (e.g., layers 51a, 51b or 51c) attenuate the evanescent electric field 56 to such an extent that the layer 51a, 51b, 51c where indicator 77's concentration is highest is not adequately excited by the evanescent electric field 56.

Darkfield Interrogation

Many of the problems associated with evanescent interrogation are reduced or eliminated when darkfield interrogation according to the present invention is used with sensing waveguide 29.

Darkfield interrogation according to the present invention may be performed by selecting, in any suitable way, the range of reflected angles $\theta_{0i}$ for interrogation light 24 from light source 26 to be such that rays of darkfield interrogation light 24b are not subject to total internal reflection within waveguide 28 at its interface 64; but instead penetrate interface 64 and obliquely enter sensing waveguide 29's detection coating 50 (e.g., enter one or more of layers 51a, 51b and 51c). See FIGS. 4 and 5. Thus, under the present invention at least part of the darkfield interrogation light 24b may be trapped within sensing waveguide 29.

This is because during darkfield interrogation, rays of darkfield interrogation light 24b may be prevented from entering the interior of cup 10 by being internally reflected at a selected inner interface 66, 67, or 70 of sensing waveguide 29. The rays of darkfield interrogation light 24b may also be reflected at a selected outer interface 34a, 64, 66, or 67 of sensing waveguide 29. As a result, an extended area of detection coating 50 may be interrogated by the darkfield interrogation light 24b that is trapped between the selected inner and outer interfaces 34a, 64, 66, 67, or 70 of sensing waveguide 29. As has been mentioned, the rays of darkfield interrogation light 24b may propagate axially down the sensing waveguide 29 (i.e., in a direction parallel to cup 10'a A-Axis). See FIGS. 4 and 5.

In contrast to evanescent interrogation, when darkfield interrogation is used the selected inner interface may be between two non-fluids (e.g., interface 66); between a fluid and a non-fluid (e.g., interface 67); or between a fluid and contacting gas (e.g. interface 70).

During darkfield interrogation, rays of darkfield interrogation light 24b are capable of propagating within waveguide 28 and of penetrating and propagating axially within part or all of one or more of detection coating 50's fluid and non-fluid layers 51a, 51b, 51c.

Thus, under the present invention, the darkfield interrogation light 24b may be trapped within a sensing waveguide 29 that may be formed, for example, from part or all of waveguide 28 and one or more selected detection layer 51a, 51b, 51c. Alternatively the darkfield interrogation light 24b may be trapped within a sensing waveguide 29 that may be formed by part or all of one or more selected detection layers 51a, 51b, 51c, in which case waveguide 28 even though not part of such a sensing waveguide 29, may still provide an optically smooth physical support for detection layer 51a in addition to supplying darkfield interrogation light 24b for such a sensing waveguide 29.

Total internal reflection of darkfield interrogation light 24b at sensing waveguide 29's selected inner interface 66, 67 or 70, and at sensing waveguide 29's selected outer interface 34a, 64, 66, or 67 may be obtained in any suitable way, such as by selecting materials with suitable refractive indexes for detection layers 51a, 51b, 51c, and waveguide 28; by selecting a compatible range of propagation angles for darkfield interrogation light 24b as it travels down sensing waveguide 29; and by using the equations provided herein to design reflector 30's inner and outer reflective surfaces 31a, 31b so that they produce reflected darkfield interrogation light 24b from light source 26 that has an appropriate range of reflected angles $\theta_{0i}$ for the darkfield interrogation of waveguide 28 and sensing waveguide 29.

By way of example, if detection coating 50 comprises two non-fluid layers 51a and 51b, and a fluid layer 51c, then under evanescent interrogation the maximum radial inward penetration of rays of evanescent interrogation light 24a may be to the non-fluid/fluid interface 67 between non-fluid layer 51b and fluid layer 51c. At interface 67, the rays of evanescent interrogation light 24a may be reflected back towards waveguide 28. In contrast, under darkfield interrogation the rays of darkfield interrogation light 24b may penetrate radially inward to, and be reflected back towards, waveguide 28 at the fluid/air interface 70 between fluid layer 51c and the air within the cup 10.

A first way that darkfield interrogation may be used is where the output signal light 58 is produced as a function of the direct excitation by the darkfield interrogation light 24b of optically active indicators 77, such as dyes, within the sensing waveguide 29. For example, dark field interrogation may be used to produce signal light 58 comprising rays of fluorescent light such as, for example, if any of detection coating 50 (e.g., any of layers 51a, 51b and 51c) or any of the analytes 52 have been labeled with any suitable fluorescent indicators 77 that fluoresce when interrogated by rays of darkfield interrogation light 24b.

A second way that darkfield interrogation may be used is where the signal light 58 is produced as a function of rays of darkfield interrogation light 24b that have been reflected, refracted, absorbed or scattered by detection coating 50 (e.g., layers 51a, 51b and 51c), by the analytes 52, or by indicators 77. As previously discussed, small amounts of a homogeneously distributed, finely divided scattering media may be incorporated within detection coating 50 so that the opacity or color of coating 50 can be monitored over its extent.

Debris on inner surface 53 of detection coating 50 (e.g., on inner surface 72 of layer 51c) may be a potential problem when using darkfield interrogation of detection coating 50, since such surface debris may give rise to measurement inaccuracies while trying to detect any analytes 52 in cup 10. However, this potential problem may be minimized or eliminated in any suitable way. For example, the inner surfaces 53, 72 may be at least partially cleansed of surface debris, such as by washing or treating them with water or with any suitable reagent, prior to trying to detect the analytes 52.

In addition, if the refractive indices of detection layers 51a and 51b are suitably selected so that darkfield interrogation light 24b is totally internally reflected at their interface 66, and if signal light 58 is emitted from the analytes 52 near, on, or in layer 51a, little or no scattering of darkfield interrogation light 24b by surface debris on or near layer 51c's inner surface 72 will occur since little, if any, of darkfield interrogation light 24b will reach the surface debris.

In any event, surface debris is of less importance if fluorescent indicators 77 are used to label detection coating 50 or the analytes 52 in cup 10, so that fluorescent signal light 58 will be produced when detecting the analytes 52 during darkfield interrogation of cup 10. This is because any darkfield interrogation light 24b that is scattered from the surface debris may easily be minimized or eliminated by any suitable optical filters in detector 60 that do not permit any scattered darkfield interrogation light 24b to pass, but do permit most, if not all, of the fluorescent signal light 58 to pass.

A prototype cup 10 was tested to compare the efficacy of evanescent interrogation versus darkfield interrogation. The prototype cup 10 had an internal diameter of about 3.2 cm and a sidewall 14 with an internal height of about 1.5 cm. For these tests a section of the sidewall 14 that was only about 0.2 mm wide was monitored proximal to the reflector 30 with a detector 60 that had had high collection efficiency but only a comparatively narrow field of view.

In a first test set, no non-fluid detection layers 51a, 51b were used in prototype cup 10. The analytes 52 were bacterial simulants in the form of fluorescent compound-labeled polystyrene microspheres about 1.1 microns in diameter purchased from Molecular Probes, Inc. of Eugene, Oreg. Sample fluid 55 was about 1.5 cc of a water suspension of the simulant analytes 52. Sample fluid 55 was placed in cup 10, which was then spun at 12,000 rpm for 5 minutes. At the end of this time, substantially all of the simulant analytes 52 had moved so that they formed a layer on waveguide 28's inner surface 32.

This first test set demonstrated that strong levels of signal light 58 could be obtained despite cup 10 not having any non-fluid detection layers 51a and 51b, so that the simulant analytes 52 rested directly on waveguide 28's inner surface 32, and were covered by layer 51c (the water from sample fluid 55). Such an approach may be acceptable, for example, where the material to be tested has been pre-purified, so that the analytes 52 are effectively the only high-density material in sample fluid 55, and where it is the quantity or number of the analytes 52 that is to be determined.

In a second test set, there was only one non-fluid layer 51a, and the analytes 52 were spores of *Bacillus globigii*, which had been labeled with a fluorescent indicator 77 (Nile Blue A) by the process of physical adsorption. Prior to conducting these tests, waveguide 28's inner surface 32 was first prepared by coating it, using physical adsorption methods, with a layer 51*a* averaging 100 Angstroms (0.01 microns) in thickness, that comprised rabbit antibodies raised against *Bacillus globigii* spores. The function of layer 51*a* was to bind the spore analytes 52 to waveguide 28's inner surface 32 when they were forced against it by centrifugal force while cup 10 was spun during the tests. After layer 51*a* was created, 0.25 cc of sample fluid 55 comprising water and the spore analytes 52 was added to cup 10. This amount of sample fluid 55 was selected in order to produce a water layer 51*c* that was about 150 microns thick when cup 10 was spun, but its thickness may be easily varied at will by suitably selecting the amount of sample fluid 55 that is added to cup 10. The layer 51*c* rested on layer 51*a* since there was no layer 51*b* in this second test set.

Cup 10 was then spun at speeds ranging from 500 rpm to about 8000 rpm for various periods of time and with varying speed-up and speed-down ramp rates. This served to help circulate sample fluid 55 within cup 10, for the purpose of helping to expose layer 51*a* to as many of the spore analytes 52 as possible. Such spinning of cup 10 also served to centrifugally concentrate the spore analytes 52 onto layer 51*a*, and formed the water layer 51*c* on top of the spore analytes 52 and layer 51*a*.

In this second test set, cup 10 was oriented so that its A-axis was vertical while it was being spun. Ramping the cup 10 down to a very slow or zero rotation rate condition drained the water layer 51*c* away from the circumferential observation area of cup 10, leaving (at most) only water fillets 76 around the spore analytes 52 (see FIG. 5) trapped on the layer 51*a*. Detector 60 monitored signal light 58 emitted from the fluorescent indicator 77-labeled spore analytes 52 while water layer 51*c* thinned as it drained away.

This second test set demonstrated that while water layer 51*c* was formed by spinning cup 10, the level of signal light 58 from the fluorescent indicator 77-labelled spore analytes 52 was about 5 times greater when darkfield interrogation was used as compared to when evanescent interrogation was used.

It is theorized that there are at least two reasons for this five-fold increase in signal light 58.

First, as has been discussed, evanescent interrogation light 24a is not able to efficiently excite the fluorescent indicator 77-labeled spore analytes 52 that were attached to surface layer 51a because of the limited penetration of the evanescent electric field 56 beyond interface 64, thereby limiting the amount of signal light 58 that can be generated by using evanescent interrogation.

On the other hand, during darkfield interrogation of the cup 10 while it was being spun, the presence of air in cup 10's interior volume 68 adjacent to a thin water layer 51c's inner surface 72 effectively created a sensing waveguide 29 comprising waveguide 28, layer 51a, and water layer 51c. Since the fluorescent indicator 77-labelled analytes 52 attached to layer 51a were located within the interior of that sensing waveguide 29, they were entirely exposed to the rays of darkfield interrogation light 24b that were trapped between that sensing waveguide 29's totally internally reflecting interfaces (i.e., outer interface 34a at waveguide 28's outer surface 34 and inner interface 70 at layer 51c's inner surface 72). As a result, effectively the entire surfaces of spore analytes 52 located within that sensing waveguide 29 could be interrogated by the darkfield interrogation light 24b carried by that sensing waveguide 29. This is highly desirable since it should produce more signal light 58 for a given quantity of fluorescent indicator 77-labeled spore analytes 52, as compared to the relatively smaller amount of signal light 58 that will be produced by waveguide 28 when it and the fluorescent indicator 77-labeled analytes 52 are subjected to evanescent interrogation.

The second reason for the observed five-fold increase in signal light 58 during the second test is that the above sensing waveguide 29 (comprising waveguide 28 and layers 51a, 51c) may carry darkfield interrogation light 24b having a higher maximum amount of optical power, as compared to the lower maximum amount of optical power that it is possible for a sensing waveguide 29 comprising waveguide 28 to carry when subjected to evanescent interrogation.

Darkfield interrogation light 24b of higher optical power may be injected into a sensing waveguide 29 comprising waveguide 28 and layers 51a, 51c because the air within cup 10's interior volume 68 has a low refractive index relative to that of waveguide 28. This allows such a sensing waveguide 29 to carry rays of light 24b that reflect internally at larger reflected angles $\theta_{Oi}$ relative to waveguide 28's optical surface of symmetry 37, than would be possible for a sensing waveguide 29 comprising a waveguide 28 when it and the fluorescent indicator 77-labeled analytes 52 are subjected to evanescent interrogation while in contact internally with a layer 51c of water.

In general, the optical power transport capability of any optical system (e.g., a sensing waveguide 29 comprising waveguide 28 and layers 51a, 51c) is commonly assumed to be proportional to the square of the system's numerical aperture (NA). The NA is equal to the sine of the largest reflected angle $\theta_{Oi}$ for the transported light rays (e.g., darkfield interrogation light 24b) relative to their direction of propagation (e.g., parallel to waveguide 28's optical surface of symmetry 37), multiplied by the refractive index of the highest index layer in the system that the transported light rays are traveling in (e.g., waveguide 28).

By way of example, if cup 10 is designed for evanescent interrogation, has a water layer 51a, and has a sensing waveguide 29 comprising a polystyrene waveguide 28, then the NA of the polystyrene waveguide 28 will be about 0.856 if the rays of evanescent interrogation light 24a are reflected at the interface 64 between the polystyrene waveguide 28's inner surface 32 and the outer surface 62 of water layer 51a.

On the other hand, if cup 10 is designed for darkfield interrogation, and has a sensing waveguide 29 comprising a polystyrene waveguide 28 and water layer 51a, then the rays of darkfield interrogation light 24b may be reflected at the interface 66 between the inner surface 61 of water layer 51c and the air in cup 10's interior volume 68. In this case the NA of the sensing waveguide 29 will be 1.23. As a result, the maximum optical power transport capability of, and the corresponding amount of signal light 58 from, the above sensing waveguide 29 regarding darkfield interrogation light 24b may then be estimated as being about 2.06 times greater than the maximum optical power transport capability of, and the corresponding amount of signal light 58 from, the above sensing waveguide 29 regarding evanescent interrogation light 24a.

In any event, one remarkable result of the second test set was the discovery that, when darkfield interrogation of cup 10 was used, the amount of fluorescent signal light 58 increased by about two-fold as the water layer 51c was drained away, as compared to the amount of signal light 58 produced by darkfield interrogation prior to the draining process. The amount of signal light 58 stabilized at this higher level once water layer 51c had ostensibly completely drained from the fluorescent indicator 77-labelled spore analytes 52 and from layer 51a's inner surface 74.

It is to be noted that this two-fold increase in the amount of fluorescent signal light 58 that occurred when water layer 51c was drained is in addition to the five-fold increased amount of fluorescent signal light 58 described above when a transition was made from evanescent to darkfield excitation.

It is theorized that there may be multiple mechanisms contributing to the observed two-fold increase in the amount of fluorescent signal light 58 that occurred when water layer 51c was drained. One such mechanism may be optical phenomena associated with the behavior of very thin fluid films on solid surfaces. In particular, thin water films are unstable and as water layer 51c was drained from cup 10 as described above, water fillets 76 created by surface tension forces remained present around (and possibly over), the fluorescent indicator 77-labelled spore analytes 52.

In other words, it is theorized that, even after water layer 51c drained away, local, very high optical power levels of darkfield interrogation light 24b could still interact with the spore analytes 52 via the water fillets 76, which acted as optical couplings to transport light 24b from waveguide 28 to the spore analytes 52. Once light 24b was transported to the spore analytes 52, it would tend to pass through the entire volume of each of the spore analytes 52, thereby efficiently exciting any fluorescent indicators 77 located within, or attached to the surface of, the spore analytes 52.

The optical power levels of light 24b within the spore analytes 52 may also be very high due to the mechanism of optical resonance, particularly since bacterial analytes 52 may have an average diameter that is comparable to the interrogation light 24b's wavelength.

In addition, another mechanism may be enhanced back-reflection of signal light 58 created within or on the surface of particulate-type analytes, such as the spore analytes 52. Each such particulate-type analyte 52 may be surrounded by air on its inward-facing side, and may be coupled optically to waveguide 28 by a microscopic water fillet 76 as previously mentioned. This imbalance in optical impedances may also enhance the amount of signal light 58 emerging from waveguide 28's outer surface 34.

This second test set demonstrated several other favorable attributes and discoveries of the present invention. First, it was discovered that while cup 10 is spinning, it may automatically produce, in a virtually instantaneous fashion, a water layer 51c that may be of uniform thickness, that has an optically smooth inner surface 72 in contact with the air in cup 10's internal volume 68, and that covers at least part of the inner surface of the non-fluid detection layer (e.g., inner surface 61 of layer 51a). Water layer 51c's inner surface 72 may be advantageously utilized as one of the reflective surfaces in an optical waveguide, thereby providing an exceedingly smooth and defect-free surface due to the individual and complementary effects of centripetal force and surface tension.

The same results may be obtained for a layer 51c comprising any other fluid, such as a buffer or reagent solution that may be added to cup 10; or for a gel layer 51c, such as a nutrient media that has some residual fluidity or plasticity. In addition, similar results may be obtained for non-fluid layers 51a, 51b, such as by forming one or both of them from respective fluids that gel or harden after being fashioned into a respective layer of uniform thickness that have respective optically smooth inner surfaces 61, 74 formed by spinning cup 10.

Such spinning of cup 10 may also be advantageously utilized to distribute on waveguide 28's inner surface 32, or on the inner surface of the outer layer of any non-fluid detection layer that is already in cup 10 (e.g., on inner surface 61 of layer 51a), any detection material that is added to cup 10 that is soft enough to flow under the g-forces created by the spinning cup 10. Depending on the nature and characteristics of such added detection material, after being spun in cup 10 it may form a detection layer (e.g., layer 51b) that has a uniform thickness, that has an optically smooth inner surface 74, and that may cover at least part of the inner surface of any non-fluid detection layer (e.g., inner surface 61 of layer 51a) that is already in cup 10.

In general, it may be desirable for detection coating 50 and for the innermost detection layer 51a, 51b, 51c (or any layer of added detection material), to have an optically smooth inner surface (e.g., inner surfaces 53, 61, 74, 72). Such optically smooth inner surfaces may be desirable because, for example, if any signal light 58 is being generated at or near any of those optically smooth surfaces, then any undesirable scattering of interrogation light 24, 24b will be minimized by those optically smooth surfaces, thereby desirably leading to lower amounts of scattered interrogation light 24, 24b entering detector 60. For example, the creation of an optically smooth inner surface 72 for fluid layer 51c will minimize any undesirable scattering of interrogation light 24, 24b from surface 72, as compared to if surface 72 was not optically smooth.

In addition, since such optically smooth surfaces (e.g., inner surfaces 53, 61, 74, 72), may be automatically formed when cup 10 is spun, the optical properties of detection coating 50 (e.g., layers 51a, 51b, 51c) will, in general, be more reproducible from cup 10 to cup 10. Also, fluid interactions with such optically smooth surfaces will be closer to theoretical expectations and more reproducible from cup 10 to cup 10.

However, having optically smooth inner surfaces (e.g., inner surfaces 53, 61, 74, 72) or optically smooth interfaces (e.g., interfaces 64, 66, 67, 70) may not always be critical. For example, let it be assumed that layer 51c comprises water and that the fouling objects which might scatter interrogation light 24, 24b are bacteria or a bacterial film. Then, since most bacteria and bacterial films have refractive indices close to water, water layer 51c would, in effect, "index match" such objects. Such index matching may help to prevent the fouling objects from scattering interrogation light 24, 24b at inner surface 72, and may thereby allow signal light 58 from the analytes 52 to produce a higher contrast image in which the analytes 52 may stand out more strongly from the background. It may also be possible to engineer the detection coating 50 (e.g., layers 51a, 51b, 51c), so that they are similar in refractive index to potential fouling objects.

By way of nonlimiting example, the cytoplasm of many bacteria has an effective refractive index slightly higher than water. If waveguide 28's inner surface 32 is coated with a hydrogel layer 51a having a typical water content of over about 50%, then such bacteria and layer 51a may have similar refractive indexes and scattering of interrogation light 24, 24b at the interface between such bacteria and layer 51a will be minimized.

Detection Coating 50 (in Detail)

In general, and referring again to FIGS. 1-3 and 5, the particular method employed by the user of cup 10 for detecting a particular kind of analyte 52 that may be present in sample fluid 55 may define the desired attributes of detection coating 50 such as, for example, the number, thickness, composition, and construction of each of layers 51a, 51b, and 51c that may comprise detection coating 50.

It is recalled that, as set forth above, for simplicity of description herein, and by way of non-limiting example, it has been assumed that detection coating 50 comprises three detection layers 51a, 51b and 51c; that layers 51a and 51b are non-fluid detection layers; and that layer 51c is a fluid detection layer, which may be formed from sample fluid 55, for example.

However, any of the detection layers in detection coating 50 (e.g., layers 51a, 51b and 51c) may comprise either a non-fluid detection layer or a fluid detection layer; there may be any number of detection layers 51a, 51b, 51c in detection coating 50; and there may be no detection coating 50 at all. In addition, none, one, or more than one of the functions described herein with respect to any particular layer 51a, 51b, 51c may be partially or wholly performed by any of the other layers 51a, 51b, 51c, either separately, or in combination. For example, one or more of the functions described herein with respect to layer 51a may be performed by layers 51b or 51c, in which case a separately discernable layer 51a may not exist.

Further, when more than one function is described herein with respect to any particular layer 51a, 51b, 51c, it is understood that that particular layer 51a, 51b, 51c may perform only one of those functions, may perform any combination of two or more of those functions, or may perform none of the described functions, and instead perform some function other than those described herein.

The respective thicknesses of the layer of sample fluid 55, detection coating 50, and each of the detection layers in detection coating 50 (e.g., layers 51a, 51b and 51c) will vary according to any applicable parameters such as, for example, their respective compositions, the particular kind of analyte 52, and the needs of the user.

By way of example, the layer of sample fluid 55 (e.g., layer 51c) may have a thickness in the range of about 5 microns to about 1,000 microns if layer 51c is part of a sensing waveguide 29 comprising waveguide 28 and layer 51c; or it may have a thickness of up to about 90% of cup 10's internal radius otherwise. Detection coating 50 may have a thickness in the range of about 100 Angstroms (0.01 microns) to about 1,000 microns; and each of the detection layers (e.g., layers 51a, 51b and 51c) may represent a fraction of detection coating 50's total thickness, commensurate with its particular role in the particular assay process being used.

In many cases, one of the important roles of the innermost non-fluid detection layer (e.g., layer 51b) that may be in contact with an innermost fluid detection layer (e.g., layer 51c, which may be a layer of sample fluid 55, for example), may be to selectively capture a particular kind of analyte 52 from sample fluid 55, and to discriminate against other materials that may be in sample fluid 55. This may be true for any or all of the different assays that are discussed herein.

Accordingly, a non-fluid layer 51b serving such a role may be referred to as a "capture layer" 51b, with respect to a particular kind of analyte 52; and may comprise, for example, one or more layers of any suitable capture molecules or materials such as antibodies, crown ethers, aptamers, DNA or RNA (Ribonucleic Acid) fragments, or any other capture moiety or element. Capture layer 51b may be covered with a fluid layer 51c.

Capture layer 51b may also serve the important role of assisting in the production of signal light 58 as a function of any analytes 52 that may be present in cup 10. Such signal light 58 may be emitted as a function of, for example, the presence, quantity, number, or at least one targeted distinguishing characteristic of the analytes 52.

It is to be noted that capture layer 51b may have the desirable attribute of affinity purification. That is, the affinity of capture layer 51b for a particular kind of analyte 52 may serve to purify analyte 52 since the analytes 52 are effectively removed from sample fluid 55 when they are attached to capture layer 51b. Such affinity purification is a desirable effect that is independent of the centrifugal-concentration of the analytes 52 towards, and eventually onto, capture layer 51b.

Capture layer 51b may be the only non-fluid detection layer in detection coating 50, in which case it may be directly supported by waveguide 28's inner surface 32. Alternatively, capture layer 51b may be indirectly carried by, or attached to, waveguide 28's inner surface 32, such as by use of one or more intermediary non-fluid detection layers (e.g., layer 51a), which may then in turn be carried by, or attached to, inner surface 32. Thus, detection coating 50 may comprise two or more non-fluid detection layers (e.g., layers 51a, 51b). Here again, capture layer 51b may be covered with a fluid detection layer 51c.

Whether capture layer 51b is directly attached to inner surface 32, or is indirectly attached to inner surface 32 by use of an intermediary detection layer (e.g., layer 51a), it may be attached to inner surface 32 or to the intermediary detection layer in any suitable way, such as by physical adsorption or by any suitable molecular bond, for example.

If a molecular bond is used, capture layer 51b's capture molecules may bond with a particular kind of analyte 52 preferentially over active regions of the capture molecules' surfaces. Accordingly, in such an event it may be desirable to attach inactive regions of the capture molecules' surfaces to inner surface 32 or to an inner surface of an intermediary detection layer (e.g., inner surface 74 of layer 51a), so that the particular kind of analytes 52 in sample fluid 55 are maximally exposed to the capture molecules' active regions.

In addition, if the capture molecules are internally rigid so that their direct connection to inner surface 32, or to an intermediary detection layer (e.g., layer 51a) may tend to hinder their desirable movement, it may be appropriate to use flexible linkage elements or molecules between the rigid capture molecules and inner surface 32 or the intermediary detection layer (e.g., layer 51a). Any suitable flexible linkage elements may be used to reduce steric hindrance and to provide a wider range of topological reactions between the capture molecules and the particular kind of analyte 52, such as polyethylene glycol segments, for example.

Although providing only one detection layer under capture layer 51b (e.g., layer 51a) is discussed in detail herein, it is understood that more than one detection layer 51a may be provided under capture layer 51b.

A further reason for providing a detection layer (e.g., layer 51a) under capture layer 51b may be that if layer 51a includes an indicator 77 (see FIG. 5), then at some point during use of cup 10, indicator 77 may provide optical amplification regarding the analytes 52, i.e., a larger change in signal light 58 may be produced by cup 10 as a function of the analytes 52 when layer 51a is interrogated by evanescent or darkfield interrogation light 24a, 24b than would be the case if there were no indicator 77 in layer 51a. It is understood that detection coating 50, and any one or more of its layers 51a, 51b, 51c, may include an indicator 77 at some point during use of cup 10.

For example, some assays for detecting a particular kind of analyte 52, such as ELISA reactions, release at least one kind of indicator 77 that may attach to, or diffuse into, detection coating 50 (e.g., attach to, or diffuse into, one or more nearby or adjacent detection layer 51a, 51b, or 51c), to form at least one two dimensional or three dimensional indicator site 78 of indicator 77 for each detected analyte 52.

This is illustrated in FIG. 5, for example by the generally spherical concentration profiles of indicator 77 within indicator site 78, that show the diffusion of indicator 77 into fluid detection layer 51c from the detected analyte 52. Similar diffusive profiles may occur in non-fluid detection layers 51a or 51b. Such indicator sites 78 may be used advantageously for providing optical amplification regarding the analytes 52 because they increase the effective optical size of the analytes 52, which may, in turn, be used to increase the changes in signal light 58 produced as a function of the analytes 52, than might otherwise be the case.

Alternatively, indicator site 78 of indicator 77 may be a two-dimensional or three-dimensional site in detection coating 50 (e.g., in layers 51a, 51b, 51c) in which indicator 77 has been depleted to some degree. This may occur, for example in a situation where one or more of layers 51a, 51b, 51c comprise a dye indicator 77 that partitions strongly onto or into the analytes 52. As a result, each detected analyte 52 may be associated with an indicator site 78 in which indicator 77 has been depleted to some degree; while the analyte 52 itself is intensely colored by the dye indicators 77 that have been partitioned onto or into it.

Calculations indicate that when small indicators 77, such as dyes with molecular weights in the range of several hundred to several thousand are released at the analyte 52 attachment sites on capture layer 51b by some reactions (e.g., by an ELISA), the indicators 77 will typically propagate in non-fluid layers 51a, 51b to waveguide 28's inner surface 32, or to the inner surface 53 of fluid layer 51c, in a comparatively short time and will laterally diffuse enough through layers 51a, 51b, 51c to create optically recognizable indicator sites 78 that are many times larger in area or volume than the analytes 52 themselves (e.g., up to 100 times larger, or more).

Figure 5A:
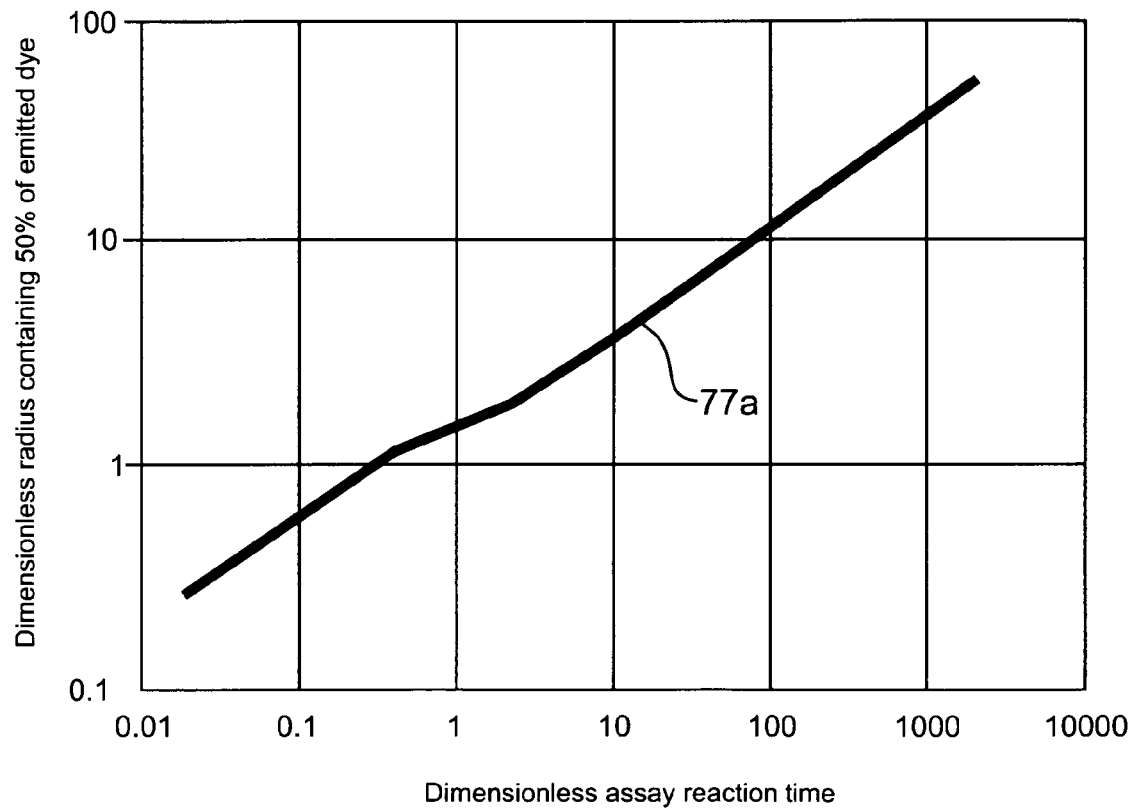
FIG. 5A shows a graph depicting diffusion in a film of an indicator emitted by a point source.

This is illustrated in FIG. 5a, wherein 77a is a graph of the dimensionless radius of an indicator site 78 plotted as a function of the dimensionless assay reaction time. The dimensionless radius may be obtained by dividing the indicator site 78's radius by the thickness of the film containing the indicator site 78 (e.g., the layer 51c seen in FIG. 5). In addition, the dimensionless radius corresponds to that radius which contains 50% of the total amount of indicator 77 emitted by a point source at the center of the indicator site 78 (e.g. emitted by an individual analyte 52).

For diffusion-dominated expansion in a film containing the indicator site 78 (e.g., fluid layer 51c), the dimensionless assay reaction time is the product of the assay reaction time and the diffusion coefficient of indicator 77 in layer 51c, divided by the square of layer 51c's thickness. It can be seen from FIG. 5a that the indicator site 78 expands approximately as the square root of the dimensionless assay reaction time, and that the expansion undergoes a change when the dimensionless assay reaction time is about equal to 1.0. At that point the diffusion process of the indicator 77 shifts from three-dimensional spherical expansion to two-dimensional lateral expansion. In either case, it is apparent that even a point source of the indicator 77 will create a spherical or disc-shaped indicator site 78 of concentrated indicator 77 that is comparable in size to the thickness of layer 51c when sufficient time is allowed for incubation, such incubation time being on the order of seconds or minutes, depending on the thickness of layer 51c and indicator 77's diffusion coefficient in layer 51c. By way of example, an elapsed time of only 14.4 seconds is needed to reach a dimensionless time of 1.0 when the thickness of layer 51c is 12 microns and the indicator 77 has a diffusion coefficient of $1 \times 10^{-7}$ cm$^2$/sec in layer 51c. This diffusion coefficient is typical of small-molecule diffusion coefficients for water or water-based gels.

Accordingly, even if the analytes 52 themselves are not directly detectable when interrogated by evanescent or dark-field interrogation light 24a, 24b, the enlarged indicator sites 78 of indicator 77 may be readily detected when so interrogated. In this manner it may be possible to readily detect and identify the presence of small pathogenic particles that are beyond the conventional resolution capabilities of optical microscopy, such as single virus particles.

Another reason for providing a detection layer (e.g., layer 51a) under capture layer 51b may be to assist in the growth (e.g., in size, quantity, or number) of any particular kind of live analytes 52 (e.g., bacteria, spores, or viruses), in order to help discriminate live from dead analytes 52, and to increase the amount of signal light 58 produced when the analytes 52 are interrogated by evanescent or darkfield interrogation light 24a, 24b. In general, such an increase in the amount of signal light 58 may be very desirable, since it may translate into greater sensitivity or greater accuracy in measuring the presence, quantity, number, or at least one targeted distinguishing characteristic of the analytes 52.

If layer 51a is a growth-assisting layer, then it may comprise any suitable nutrient rich, growth-assisting material, such as a gel comprising a high clarity polyacrylamide gel combined with MBI Purified Agar (Marine BioProducts International, Delta B.C., Canada); or nutrient gels such as EasyGel (Micrology Laboratories LLC, located in Goshen Ind.). The growth-assisting gel can be prepared, added to cup 10, and allowed to solidify while cup 10 is spun, so that a thin layer 51a of the growth-assisting gel is formed on waveguide 28's inner surface 32. The degree of cross linking in the growth-assisting gel may be altered in any suitable way to optimize for the desired molecular size range that can diffuse into and out of the growth-assisting gel. The desired molecular size range may be, for example, the molecular size range of any particular indicator 77 that is produced in response to a chemical or physical reaction that occurs as a function of the analytes 52.

After growth-assisting layer 51a has been prepared, any suitable capture layer 51b for a particular kind of live analyte 52 may then be formed on growth-assisting layer 51a's inner surface 61 in any suitable way. For example, if the analytes 52 are a particular kind of bacteria, then capture layer 51b may comprise antibodies that have been immobilized on growth-assisting layer 51a's inner surface 61, wherein the antibodies have been chosen to be useable in any suitable assay for detecting that particular kind of bacteria.

The antibodies may be immobilized on growth-assisting layer 51a's inner surface 61 in any suitable way, such as by taking advantage of the fact that most gels and agar that may comprise growth-assisting layer 51a have free amino groups incorporated into their structures to which the antibodies may be bonded.

For example, such a capture layer 51b may be formed by first incubating growth-assisting layer 51a with a biotinylation reagent such as EZ-Link Sulfo-NHS-LC-biotin (made by Pierce Bio-Technology, located in Rockford, Ill. Next, the biotinylation reagent may be incubated with avidin or streptavidin. Finally, capture layer 51b on growth-assisting layer 51a's inner surface 61 may be completed by incubating growth-assisting layer 51a with biotinylated capture antibody. In other words, the capture layer 51b may comprise the layer of biotinylated capture antibodies on the layer 51a's inner surface 61.

Alternatively, if growth-assisting layer 51a does not incorporate free amino groups, any suitable way of adding free amino groups to growth-assisting layer 51a may be used, such as by adding a polyamine such as poly(lysine) or poly (ethylene amine) to growth-assisting layer 51a while it is being made, for example.

During use of the present invention, capture of any live analytes 52 in sample fluid 55 may be assisted by using cup 10 to centrifugally-concentrate the live analytes 52 towards, and eventually onto, capture layer 51b's inner surface 74 in the manner described herein, so that they can better interact with capture layer 51b. After the live analytes 52 have been captured by capture layer 51b, they may then be incubated and grown in any suitable way.

As an alternative to layer 51a being a growth-assisting layer, the captured live analytes 52 may be directly incubated in any suitable growth medium that may be introduced into cup 10 after they have been captured by capture layer 51b. Thus, one of the functions of sample fluid 55 may be to act as a growth medium. If sample fluid 55 does not comprise a growth medium, then sample fluid 55 may be removed from cup 10 before any suitable growth medium is added to cup 10.

In any event, if cup 10 is then spun the captured live analytes 52, and their progeny, may be immersed in a layer 51c of growth medium that may be distributed smoothly over capture layer 51b's inner surface 74 by the centrifugal forces generated by the spinning cup 10.

The fluid growth medium in cup 10 may be converted to a non-fluid detection layer 51c (e.g., may be converted to a gel). This may be done in any suitable way such as by adding a light-polymerizeable media or a gelling agent to the fluid growth medium, or by simply reducing the temperature of the fluid growth medium below its gelation temperature.

Such a non-fluid detection layer 51c may be desirable because the live analytes 52 may be trapped within or on it; and because it may form part of detection coating 50, and thus may assist in optically detecting the trapped live analytes 52 in the manner discussed herein for the other detection layers (e.g., fluid layer 51c and non-fluid layers 51a and 51b).

As a further alternative, a small pool of fluid growth medium may be introduced into a cup 10 that has been oriented so that its A-axis is disposed at an angle from the vertical, such as if it is disposed horizontally, for example. Slowly rotating cup 10 will then cause periodic immersion of at least part of capture layer 51b's inner surface 74 in the fluid growth medium, thereby renewing nutrient levels for the captured live analytes 52, while utilizing only a small amount of fluid growth medium in the process.

In any event, ingredients that select for specific growth of a particular kind of live analyte 52 may be added to growth-assisting layer 51a, or to the fluid growth medium that is introduced into cup 10, in order to maximize the growth of those live analytes 52. For example, if the live analytes 52 are E. Coli O157:H7 it is known that their growth and reproduction may be improved by adding ingredients such as Modified Trypticase Soy Broth (mTSB).

Similarly, ingredients that kill or inhibit the growth of any undesired live organisms that may be present in sample fluid 55 may be added to growth-assisting layer 51a, or to the fluid growth medium that is introduced into cup 10, in order to help maximize the growth of the desired kind of analyte 52 that may be present in sample fluid 55, and to help minimize the number or growth of any undesired live organisms that may be present in sample fluid 55.

For example, if the live analytes 52 are E. Coli O157:H7 it is known that adding cefexime, cefsuldin, and vancomycin will kill or inhibit the growth of many undesired live organisms other than E. Coli O157:H7 that may be present in sample fluid 55.

Alternatively, the same results may be at least partially achieved in any other suitable way, such as by incubating sample fluid 55 at a temperature that inhibits the growth of any undesired live organisms that may be present in sample fluid 55, while comparatively encouraging the growth of the desired kind of live analyte 52. For example, if sample fluid 55 in cup 10 is incubated at 45° C., that will inhibit the growth of many organisms other than E. Coli O157:H7.

Detection Assays

As has been discussed herein, high-density analytes 52 may be centrifugally-concentrated towards, and eventually onto, capture layer 51b by the centrifugal force that is provided by spinning cup 10. In addition, as has also been discussed herein, the analytes 52 may be concentrated near to, on, or within capture layer 51b by affinity purification of analyte 52 by capture layer 51b.

Such centrifugally-concentrated or affinity purified analytes 52 may then be subjected to any suitable detection assay for detecting the analytes 52. If the analytes 52 are living, it is noted they may not be harmed by such centrifugal-concentration or affinity purification, so that they may incubated and grown in any suitable way, such as in any of the ways discussed herein, prior to being subjected to any suitable detection assay.

Suitable detection assays may include, by way of example, one or more of any of the assays discussed herein, either singly or in combination. Regardless of the particular kind of detection assay being used, cup 10 may be subjected to evanescent or darkfield interrogation; and either kind of interrogation may be performed while cup 10 is spinning, or while it is not spinning.

Competitive Assays

Any suitable competitive assay may be used as a detection assay in connection with the present invention. A competitive assay may be, for example, one in which sample fluid 55 in cup 10 contains a particular kind of unlabeled analytes 52 that are to be detected. A solution containing labeled analytes 52 that have been previously labeled in any suitable way (e.g., during a first reagent incubation step) with any suitable indicator 77, such as a fluorescent compound, for example, may then be added to the sample fluid 55 in cup 10. During a second reagent incubation step indicator 77-labeled analytes 52 are then allowed to compete with the unlabeled analytes 52 for antibody bonding sites on a previously prepared capture layer 51b.

Cup 10 may then be subjected to evanescent or darkfield interrogation. If a fluorescent indicator 77 was used to label the analytes 52, then, in general, the amount of fluorescent signal light 58 emitted from waveguide 28's outer surface 34 will be inversely proportional to the presence, quantity, number, or at least one targeted distinguishing characteristic of the unlabeled analytes 52 in sample fluid 55.

Sandwich Format Immunoassays

Any suitable sandwich format immunoassay may be used as a detection assay in connection with the present invention. A sandwich format immunoassay may be, for example, one in which an initial incubation of sample fluid 55 in cup 10 allows the particular kind of analyte 52 to be captured by (e.g., bound to) any suitable surface capture sites provided on a previously prepared capture layer 51b. After a wash step, the captured analytes 52 may then be rendered optically detectable in any suitable way, such as by labeling them in any suitable way (e.g., during a reagent incubation step), with any suitable indicator 77. Cup 10 may then be subjected to evanescent or darkfield interrogation, and signal light 58 will be emitted from waveguide 28's outer surface 34 as a function of the presence, quantity, number, or at least one targeted distinguishing characteristic of captured analytes 52.

If such labeling of the analytes 52 is done with a fluorescent compound indicator 77, then this type of sandwich format immunoassay may be termed a sandwich format fluoroimmunoassay, and the amount of fluorescent signal light 58 emitted from waveguide 28's outer surface 34 will be directly proportional to the presence, quantity, number, or at least one targeted distinguishing characteristic of the captured analytes 52. Sandwich format fluoroimmunoassays may be used to detect many different kinds of analytes 52, such as viruses, cells, or spores.

For example, if the analytes 52 are E. Coli O157:H7, then cup 10 may be provided in any suitable way with a capture layer 51b that comprises any suitable capture molecules, such as capture antibodies that are specific for E. Coli O157:H7. Such capture antibodies may be purchased from Kirkegaard & Perry Laboratories of Gaithersburg, Md. Sample fluid 55 may also contain any suitable buffer salts, wetting agents or other additives for promoting flow of sample fluid 55, and for maximizing the performance or longevity of the capture antibodies.

Sample fluid 55 may then be removed, and cup 10 rinsed with PBST (phosphate buffered saline with Triton X-100). A solution of fluorescent compound-labeled detection antibodies may then be added to cup 10. The detection antibodies may be labeled in any suitable way with any suitable fluorescent compound, such as Cy5 (Amersham Biosciences of Piscataway, N.J.).

The capture and detection antibodies may or may not be the same. Sometimes selecting the capture and detection antibodies to be different may be useful, such as where the analyte 52 is small, and has only a few sites that are suitable for antibody attachment. In such a case selecting the capture and detection antibodies to be different will have the advantage of them not both competing for the same limited number of attachment sites on the analytes 52. In any event, cup 10 may then be spun for any suitable amount of incubation time, such as about five minutes, during which it may be subjected to evanescent or darkfield interrogation. During the incubation time an increasing number of the Cy5-labeled detection antibodies will react with, and attach to, the analytes 52 that have been captured by capture layer 51*b*'s capture antibodies, thereby giving rise to a corresponding increasing amount of fluorescent signal light 58 emitted from waveguide 28's outer surface 34 while cup 10 is being interrogated. Naturally, the wavelengths of evanescent or darkfield interrogation light 24*a*, 24*b* may be selected to enable them to cause the Cy5 to fluoresce. As an option, the solution of Cy5-labeled detection antibodies may then be removed from cup 10, which may be rinsed again with PBST, and then subjected again to evanescent or darkfield interrogation. In either case, the presence, quantity, number, or at least one targeted distinguishing characteristic of the analytes 52 in the original sample fluid 55 may be detected by any amount of fluorescent signal light 58 emitted from waveguide 28's outer surface 34 that is statistically above the background level.

ELISA (Enzyme Linked Immunosorbent Assay)

Any suitable ELISA may be used as a detection assay in connection with the present invention. An ELISA may involve, for example, an initial capture incubation step in which a particular kind of analyte 52 present in sample fluid 55 is bound to surface capture sites in cup 10 using a previously prepared capture layer 51*b*. The captured analytes 52 may then be rendered chemically active in any suitable way, such as by the attachment of an active enzyme to them in a first reagent incubation step. In a second reagent incubation step, any suitable indicator 77, such as a fluorescent compound, may then be formed in any suitable way, such as by action of the analyte 52's active enzymes on a particular kind of molecule that is initially present in the second reagent.

A horizontally oriented cup 10 with detector 60 located near the top of waveguide 28's outer surface 34 (as if FIG. 1 was rotated 90° to the left), may be preferred for ELISA-type assays. In performing this assay, sample and reagent fluids introduced into cup 10 during respective sample and reagent incubation steps will form a small pool at the bottom of cup 10's sidewall 14. Subsequent rotation of cup 10 during the sample and reagent incubation steps will periodically reapply fresh fluid from this pool to capture layer 51*b*'s inner surface 74, thereby permitting efficient capture of analytes 52 and higher activities of the reagents, increasing overall assay sensitivity and/or shortening assay time.

A conventional ELISA for cup 10 will now be described in greater detail. Sample fluid 55 containing a particular kind of bacterium, virus, cell, spore or any other analyte 52 is added to cup 10, which has a capture layer 51*b* comprising any suitable capture molecules for the analytes 52. During the capture incubation step, cup 10 is spun at high rpm for a specific length of time to help enable the capture molecules to capture the analytes 52. Sample fluid 55 may also contain buffer salts, wetting agents and other additives that promote flow of sample fluid 55 or maximize the performance or longevity of whatever capture molecules may be used in capture layer 51*b*.

Sample fluid 55 is then removed, and cup 10 rinsed with PBST. During the first reagent incubation step, a first reagent solution is added to cup 10. The first reagent solution contains any suitable agent for rendering the analytes 52 chemically active, such as active enzyme-labeled antibodies that are specific to the analytes 52. Cup 10 is spun again so that the active enzyme-labeled antibodies may attach to the captured analytes 52. The first reagent solution is then removed and cup 10 is rinsed again with PBST.

During a second reagent incubation step, a second reagent solution comprising a precursor for an indicator 77 is added to cup 10, which is then spun to distribute the precursor solution as a thin layer 51*c* over capture layer 51*b*. The enzyme-labeled antibodies attached to the captured analytes 52 react with the precursor to create indicators 77.

Cup 10 may then be subjected to evanescent or darkfield interrogation before, during or after the second reagent incubation step. In general, the amount of fluorescent signal light 58 emitted from waveguide 28's outer surface 34 may be directly proportional to the presence, quantity, number, or at least one targeted distinguishing characteristic of the captured analytes 52. Up to a point, increasing the incubation time for the second reagent incubation step may result in a corresponding increase in the amount of signal light 58 emitted from waveguide 28's outer surface 34, because there has been more time for the active enzyme molecules of the active enzyme-labeled antibodies that are attached to the captured analytes 52 to convert precursor into indicator 77.

If indicator 77 is a fluorescent indicator 77, it may be desirable to rotate cup 10 more slowly for the second reagent incubation step so that only a thin reagent layer 51*c* remains on capture layer 51*b*'s inner surface 74 at the observation area, thereby minimizing the amount of background fluorescence from fluorescent indicators 77 randomly distributed in the reagent solution. A thinner layer 51*c* may also be advantageous from the standpoint that the fluorescent indicator 77 may have a higher concentration and occupy a larger effective face area when visualized, making these optical anomalies easier to detect and allowing the detection of smaller analytes 52.

By way of a second example of an ELISA, a particularly intriguing variant is a thin-film ELISA. A thin film ELISA is the same as the conventional ELISA described above as a first example, with respect to its capture incubation step and first reagent incubation step.

However, during a second reagent incubation step the enzyme-labeled antibodies that are attached to the captured analytes 52 will react with a constituent of a second reagent added to cup 10, or with one or more constituents of one or more previously prepared detection layers 51*a*, 51*b*, to produce a concentration of either a fluorescent or colorimetric indicator 77 within layers 51*a*, 51*b*; in contrast to the conventional ELISA described above as a first example, where the precursor for indicator 77 is in a second reagent solution that forms a liquid layer 51*c* covering capture layer 51*b*, and indicator 77 remains in that solution.

In this second example, due to diffusion of the fluorescent or calorimetric indicator 77 or an activated precursor of such an indicator 77 into detection layers 51*a*, 51*b*, each analyte 52 becomes immersed in a dot of intense color (e.g., indicator sites 78 seen in FIG. 5) that is detectable when subjected to evanescent or darkfield interrogation. Such an Indicator 77 is preferably immobilized in one or more of layers 51*a*, 51*b*, or is concentrated therein due to a favorable partition coefficient relative to liquid layer 51*c* so as to be available for interrogation by evanescent or darkfield interrogation light 24*a*, 24*b*.

In this second example, if one or more of detection layers 51*a*, 51*b* contains a precursor for such a fluorescent indicator 77, any suitable precursor may be used, such as 9H-(1,3-dichloro-9,9-dimethylacridin-2-one-7-yl)phosphate (e.g., DDAO-phosphate sold by Molecular Probes of Eugene, Oreg.). For such a precursor, any suitable active enzyme, such as alkaline phosphatase, may be attached to captured analytes 52 in any suitable way, such as by being conjugated to an antibody specific for analytes 52. The active enzymes that are attached to captured analytes 52 will react with the DDAO-phosphate to produce the fluorescent indicator 77.

Metabolic Activity Assays

Any suitable way of detecting any ongoing metabolic activity of the analytes 52 in sample fluid 55 in cup 10 may be used as a detection assay in connection with the present invention. For example, a particular kind of analyte 52 may first be bound to any suitable surface capture sites on a previously prepared capture layer 51b during a capture incubation step. The captured analytes 52 may then be detected by using in any suitable way any suitable metabolic indicator 77, such as by staining the captured analytes 52, or any of their metabolic products, with any suitable metabolic indicator 77, such as a dye, for example. The dye may, for example, render one or more of the metabolic products of captured analytes 52 fluorescent or colored, and may detect, for example, whether the captured analytes 52 are cells, what kind of cells they may be, and whether they are alive.

Alternatively, the metabolic indicator 77 may signal a local change in oxygen concentration in the vicinity of captured analytes 52, such as a reduced oxygen concentration caused by the metabolic activity of the captured analytes 52.

Cup 10 may then be subjected to evanescent or darkfield interrogation. If the dye metabolic indicator 77 is fluorescent, for example, little or no fluorescent signal light 58 may indicate that there are few, or no, analytes 52 in sample fluid 55, or that most, if not all, of them are dead. On the other hand, if the analytes 52 are alive, then in general the amount of fluorescent signal light 58 emitted from waveguide 28's outer surface 34 may be directly proportional to the presence, quantity, number, or at least one targeted distinguishing characteristic of the live captured analytes 52.

By way of providing further examples regarding detecting any ongoing metabolic activity of the analytes 52 in sample fluid 55 in cup 10, many common culture and bioassay methods may be used as detection assays in connection with the present invention.

As one option where there are live analytes 52, such as a particular kind of microbe for example, at least one of detection layers 51a, 51b may be doped with any suitable precursor for any suitable metabolic indicator 77. A suitable precursor may be one that produces, or helps to produce, the metabolic indicator 77 when affected by one or more aspects of the metabolism of the captured analytes 52, such by their pH, or by their redox reactions.

In addition, a suitable precursor may be one that absorbs little, if any, of the evanescent or darkfield interrogation light 24a, 24b, and that emits little, if any, fluorescent light when subjected to evanescent or darkfield interrogation. A suitable metabolic indicator 77 may be one that produces output signal light 58 as a function of any aspect of the metabolic activity of the analytes 52 when subjected to evanescent or darkfield interrogation.

For any particular chosen pH metabolic indicator 77 it may be preferable to use at least two wavelengths of evanescent or darkfield interrogation light 24a, 24b to interrogate detection layers 51a or 51b. One of those wavelengths may be selected to be the isobestic wavelength of the chosen pH metabolic indicator 77, because a change in pH has essentially no effect on signal light 58 produced by the chosen pH metabolic indicator 77 at its isobestic wavelength. A second wavelength of interrogation light 24a or 24b may be selected to fall at an absorbance or emission peak wavelength of the chosen pH metabolic indicator 77 that is associated with low or high pH. The electrical output signals that detector 60 produces as a function of the signal light 58 that is emitted at the isobestic wavelength and at the absorbance or emission peak wavelength may then be used in any suitable way, such as in ratiometric signal processing, to correct for optical fluctuations or changes in layers 51a or 51b that are not pH related.

Staining Assays

Any suitable way of staining the analytes 52 in sample fluid 55 in cup 10 may be used as a detection assay in connection with the present invention. For example, the analytes 52 may be bound to any suitable surface capture sites on a previously prepared capture layer 51b during a capture incubation step. The captured analytes 52 may then be stained in any suitable way with any suitable stain indicator 77, such as any suitable fluorescent or colored dye.

Cup 10 may then be subjected to evanescent or darkfield interrogation. If stain indicator 77 is a fluorescent dye, for example, the amount of fluorescent signal light 58 emitted from waveguide 28's outer surface 34 may be, in general, directly proportional to the presence, quantity, number, or at least one targeted distinguishing characteristic of the stained analytes 52.

If the analytes 52 are living, such as bacteria, viruses or spores, for example, stain indicator 77 may be used in any suitable way to stain any suitable interior or exterior part of the analytes 52, or stain indicator 77 may be covalently bonded to any suitable antibody or DNA fragment relating to the analytes 52 that conveys high biospecificity.

For example, if the living analytes 52 are bacteria, they may be stained with any suitable fluorescent dye stain indicator 77 in any suitable way, such as by means of in situ hybridization using DNA or RNA probes, a method that has been used successfully for detection of bacteria by conventional fluorescence microscopy. The fluorescent dye stain indicator 77 may then be interrogated by evanescent or darkfield interrogation light 24a, 24b of any suitable wavelength, such a wavelength of 635 nm, for example, and will produce fluorescent signal light 58 that will distinguish the stained bacterial analytes 52 from debris that may be present in sample fluid 55. The stained bacterial analytes 52 may also be distinguished from debris and detected non-specifically by selecting stain indicator 77 to be any suitable cell stain, such as SYTO 60 or SYTO 62 (Molecular Probes, Eugene, Oreg.), for example.

In general, metabolic activity assays and staining assays may create a local indicator site 78 of indicator 77 as a function of, for example, the presence, quantity, number, or at least one targeted distinguishing characteristic of each detected analyte 52 that may be present in cup 10's interior volume 68.

Alternatively, as has been discussed for a dye indicator 77 that partitions strongly onto or into the analytes 52, each detected analyte 52 may be surrounded by a corresponding indicator site 78 in detection layers 51a, 51b that has been depleted to some degree of the dye indicator 77, while the detected analyte 52 itself is intensely colored by dye indicators 77 that have partitioned onto or into it.

On the other hand, if a metabolic indicator 77 is used, each live analyte 52 may be located at the center of a generally circular or spherical indicator site 78 of the metabolic indicator 77 that is produced in detection layers 51a or 51b by the diffusion of the metabolic indicator 77 from the live analytes 52. For example, detection of E. coli bacteria may be accomplished by adding the specific metabolic indicator 77, 4-methylumbelliferone-β-D-galactoside to cup 10, which gives rise to the fluorescent compound 4-methylumbelliferone in the presence of coliform bacteria such as E. Coli. The diffusion of that fluorescent compound away from the E. Coli bacteria into layers 51a or 51b will then generate fluorescent signal light 58 when interrogated with rays of evanescent or darkfield interrogation light 24a, 24b.

Nucleic Acid Assays

Any suitable DNA or RNA assay for the analytes 52 in sample fluid 55 in cup 10 may be used as a detection assay in connection with the present invention. For example, the analytes 52 may first be ruptured in any suitable way to release their nucleic material, e.g., to release particular segments of their DNA or RNA. Such released DNA or RNA segments may then be detected by using any suitable detection assay in any suitable way. For example, any suitable competitive assay or sandwich format immunoassay may be used in which, for example, the capture molecules bound to capture layer 51b in cup 10 may be DNA or RNA segments that are complementary to the released RNA or DNA segments. After the analytes 52 have been ruptured, their released DNA or RNA segments may then be labeled in any suitable way (e.g., during a reagent incubation step), with a reagent containing any suitable nucleic acid indicator 77, such as a fluorescent compound.

Cup 10 may then be subjected to evanescent or darkfield interrogation. If the nucleic acid indicator 77 is a fluorescent compound, then the presence and amount of the fluorescent signal light 58 emitted from waveguide 28's outer surface 34 may indicate the presence of the released DNA or RNA segments, and quantify their numbers. This, in turn, may indicate the presence of the analytes 52, and quantify their numbers.

Nucleic Acid Assays Incorporating PCR

If the number of released RNA or DNA segments produced by rupturing the analytes 52 in sample fluid 55 in cup 10 is not adequate for the performance of a particular desired detection assay, then there are several techniques that can be used to amplify, in situ, the number of such released RNA or DNA segments.

For example, one such technique that may be used is a Polymerase Chain Reaction (PCR). One of the requirements for performing a PCR is that sample fluid 55 must be heated and cooled rapidly, so that the released RNA or DNA segments can be replicated exponentially. The cup 10 is in some respects an ideal platform for fulfilling this requirement.

Figure 6:
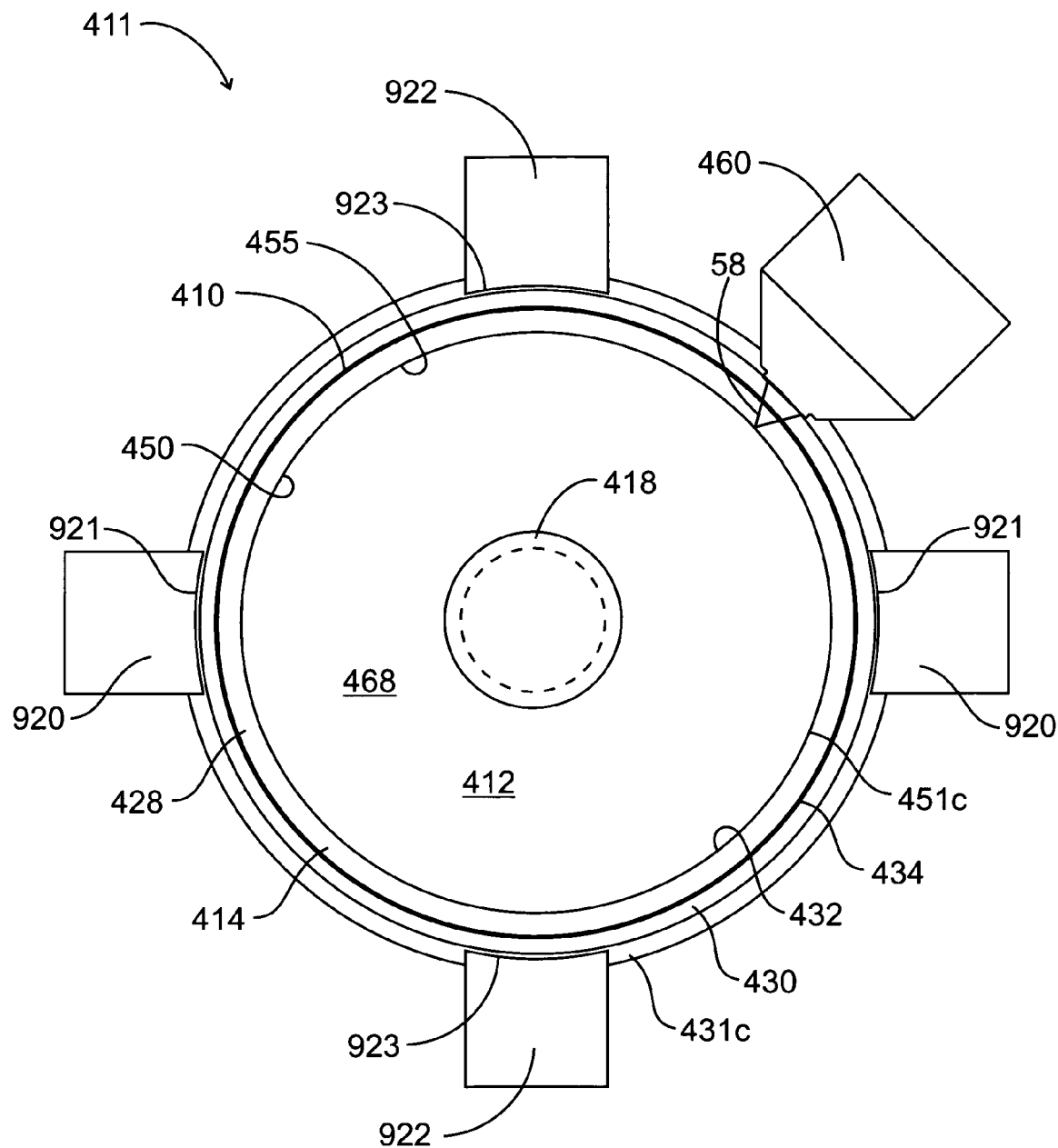
FIG. 6 is a diagrammatic top plan view of another embodiment of the optical assay apparatus of the present invention.

Turning now to FIG. 6, an optical assay apparatus 411 is illustrated that may be used to perform nucleic acid assays incorporating PCR. For clarity, certain parts of optical assay apparatus 411 have been given the same reference numerals as the corresponding parts of optical assay apparatus 11, but with a "4" prefix. It is understood that the apparatus 411 and 11 are the same as each other, or are at least similar to each other, in any particular respect such as with respect to their respective components, mountings, locations, quantities (how many), sizes, shapes, designs, materials, compositions, constructions, manufactures, physical properties, dimensions, specifications, variations, operations, methods, and uses, except for those differences which will be made apparent by all of the disclosures herein.

The apparatus 411 may comprise a light source 426 (not illustrated, for clarity), a detector 460, at least one heater 920, at least one cooler 922, and an assay cup 410. Cup 410 may comprise a base 412 having a driveshaft holder 418, and a sidewall 414 having an optical waveguide 428 and a reflector 430. Heater 920 and cooler 922 may be used with any of the cups 10, 210, 210a, 310, 410 disclosed herein A typical volume of sample fluid 455 that is needed to perform a PCR in cup 410 may be on the order of 25 to 250 microliters. When cup 410 is spun, sample fluid 455 will be distributed as a thin fluid detection layer 451c on waveguide 428's inner surface 432.

Rapid changes in temperature of sidewall 414 may be accomplished with modest heat input, or with modest cooling, because sidewall 414 is thin, and because it may be made from a material (such as any suitable polymer, for example) that has a relatively low heat capacity per unit volume as compared to such materials as metals, ceramics or glasses. Similarly, rapid changes in temperature of detection coating 450 and sample fluid 455 (e.g., detection layer 451c) may be accomplished because they are typically very thin, and low in mass.

Each heater 920 may be of any suitable kind, such as the bar-shaped electrical heaters 920 shown in FIG. 6, for example. Although two heaters 920 are illustrated, there may be fewer, or more, heaters 920. Each heater 920 may have a face 921 whose curvature matches that of waveguide 428's outer surface 434, and may be mounted so that its face 921 is very close to, or even lightly touching, outer surface 434. As a result, heat transfer between each heater 920 and outer surface 434 will be very efficient, and detection coating 450 (including detection layer 451c) on inner surface 432 will be rapidly heated to the desired temperature.

Each cooler 922 may be of any suitable kind, such as the bar-shaped electrical coolers 922 shown in FIG. 6, for example. Although two coolers 922 are illustrated, there may be fewer, or more, coolers 922. Each cooler 922 may have a face 923 whose curvature matches that of waveguide 428's outer surface 434, and may be mounted so that its face 923 is very close to, or even lightly touching, outer surface 434. As a result, heat transfer between each cooler 922 and outer surface 434 will be very efficient, and detection coating 450 (including detection layer 451c) on inner surface 432 will be rapidly cooled to the desired temperature.

Heaters 920 and coolers 922 may be used while cup 410 is being spun to provide the rapid alternate heating and cooling of the entire detection coating 450 (including detection layer 451c) needed by a PCR to amplify the number of released RNA or DNA segments. While cup 410 is being spun, detector 460 may be used to detect the amplified released RNA or DNA segments by means of signal light 58 emitted from waveguide 428's outer surface 434 as a function of the presence, quantity, number, or at least one targeted distinguishing characteristic of the amplified released RNA or DNA segments.

Alternatively, any other suitable methods or devices may be used for rapidly heating or cooling detection coating 450 (including detection layer 451c). For example, detection coating 450 (including detection layer 451c) may be heated directly by mounting an infrared (IR) source (such as an IR filament-style heater) or a microwave source (such as the output waveguide of a microwave oscillator) adjacent to waveguide 428's outer surface 434 and focusing or directing the source's energy output at outer surface 434 and detection coating 450 (including detection layer 451c). Microwave and infrared radiation are both strongly absorbed by any water in detection coating 450 (including detection layer 451c), and it may be possible to heat that water directly without heating waveguide 428 by forming waveguide 428 from any suitable material, such as a plastic that has a spectral window in the selected IR or microwave waveband. Such direct heating of detection coating 450 (including detection layer 451c), may provide higher production rates by the PCR of the released RNA or DNA segments, while providing good detection of them since cup 410 may be spun at a high rpm.

Figure 7:
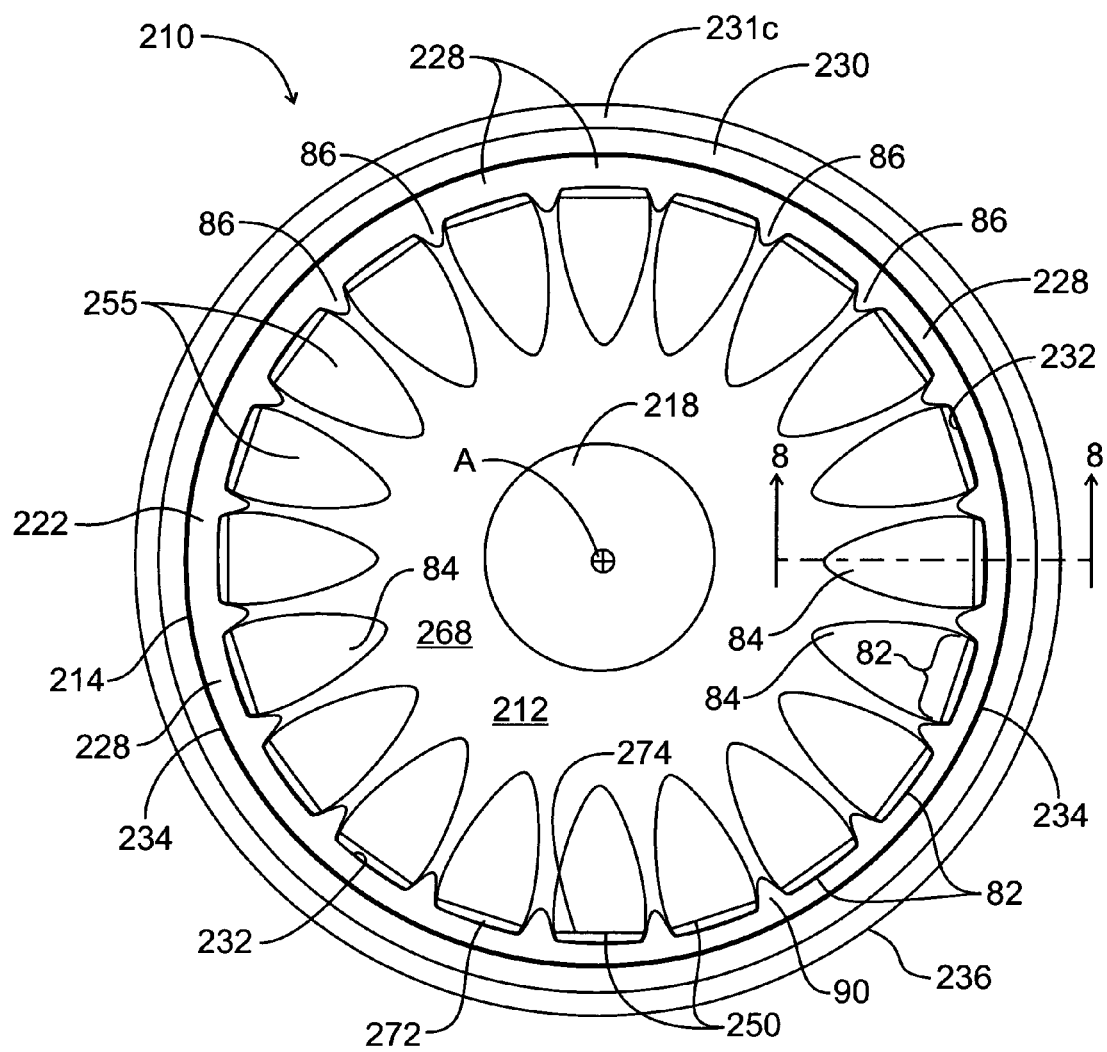
FIG. 7 is a diagrammatic top plan view of another embodiment of the optical assay cup of the present invention.

Circumferentially Segmented Cup 210 (FIGS. 7-9)

Turning now to FIGS. 7-9, the circumferentially segmented cup 210 may be used to test for at least one kind of analyte 52; or it may be used to test for at least one targeted distinguishing characteristic of at least one kind of analyte 52. Cup 210 may be used with any of the assays described herein; and may have a cover 16 or a cover 316.

Cup 210 is the same as, or at least similar to, cups 10, 210*a*, 310 and 410 in all respects, such as with respect to its respective mountings, locations, quantities (how many), sizes, shapes, designs, materials, compositions, constructions, manufactures, physical properties, dimensions, specifications, variations, operations, methods, and uses, except for those differences which will be made apparent by all of the disclosures herein. Accordingly, for clarity and simplicity, certain parts of cup 210 have been given the same reference numerals, with a "2" prefix, as the reference numerals used for the corresponding respective parts of cup 10.

As a conceptual starting point, cup 210 may be viewed as being made by circumferentially segmenting the waveguide 28 of cup 10's sidewall 14 into at least two circumferential waveguides 228, each having a respective circumferential arc width, a proximal edge 236, and a distal edge 222.

Each of the circumferential waveguides 228 so created may have respective inner and outer surfaces 232, 234; and may be of any suitable size, shape, circumferential arc width, volume, construction, materials, compositions and orientation; and may not be uniform in size, shape, circumferential arc width, volume, construction, materials, compositions and orientation between its proximal and distal edges 236, 222. Any particular circumferential waveguide 228 may be different in size, shape, circumferential arc width, volume, construction, materials, compositions and orientation from one or more of the other circumferential waveguides 228. One or more of the respective parts of one or more of circumferential waveguides 228 may be contiguous with each other (e.g., their respective outer surfaces 234).

Any particular circumferential waveguide 228's inner surface 232 may comprise a respective circumferential testing segment 82. Each testing segment 82 may be provided with a respective reservoir 84 located in cup 210's base 212. The reservoirs 84 may contain any suitable reservoir fluid 255, such as sample fluid 55, a reagent, or water for example. Any particular reservoir fluid 255 may be different, respectively, from one or more of the other reservoir fluids 255.

Any particular circumferential testing segment 82 of any particular circumferential waveguide 228 may comprise a respective detection coating 250 on at least part of inner surface 232 of that particular circumferential waveguide 228. Detection coating 250 may comprise respective detection layers (e.g., detection layers 251*a*, 251*b*, and 251*c*). Detection coating 250 of any particular testing segment 82 may be different from detection coating 250 of one or more of the other testing segments 82.

Any particular pair of adjacent circumferential waveguides 228 and their respective testing segments 82 or reservoirs 84 may be separated from each other by any suitable respective demarcation 86. Any particular demarcation 86 may be different from one or more of the other demarcations 86, e.g., the demarcation 86 between a pair of adjacent testing segments 82 may be different from the demarcation 86 between a pair of adjacent reservoirs 84. A single demarcation 86 may separate a pair of adjacent circumferential waveguides 228 and their respective testing segments 82 and respective reservoirs 84 from each other.

A particular demarcation 86 may comprise any suitable demarcating structure or substance. For example, as seen in FIGS. 7-8, a particular demarcation 86 may comprise a ridge 86 that extends into cup 210's interior volume 268 from cup 210's sidewall 214 or base 212, and that separates two adjacent testing segments 82 and their respective reservoirs 84 from each other. Alternatively, or in addition, a particular demarcation 86 may comprise a hydrophobic coating applied to a portion of the inner surface of the cup 210's sidewall 214 or base 212.

A particular demarcation 86 may serve one or more of the following functions: (a) providing a local null reference zone (such as, for example, by being selected to be inert with respect to a particular assay with which cup 210 may be used); (b) isolating a particular pair of adjacent testing segments 82 or reservoirs 84 from each other, such for helping to prevent cross-contamination of their respective fluids; (c) providing a marker for identifying a particular testing segment 82 or reservoir 84; and (d) helping to channel reservoir fluid 255 from a particular reservoir 84 to its respective testing segment 82 when cup 210 is spun.

The testing segments 82, reservoirs 84 and demarcations 86 may be of any suitable respective size, shape, circumferential arc width, volume, construction, materials, composition, and orientation; and may not be uniform in any particular direction with respect to their respective size, shape, circumferential arc width, volume, construction, materials, compositions and orientation. Any particular testing segment 82, reservoir 84 and demarcation 86 may be different in its respective size, shape, circumferential arc width, volume, construction, materials, compositions, and orientation from one or more of the other testing segments 82, reservoirs 84 and demarcations 86.

Although one reservoir 84 is illustrated as being provided for each testing segment 82, any particular testing segment 82 may be provided with two or more reservoirs 84. In addition, any two, or more, of the testing segments 82 may share a particular reservoir 84.

By way of example, for a cup 210 having a 3 cm diameter and a sidewall 214 that is 13 mm high; 20 circumferential waveguides 228 and testing segments 82 may be provided, each having a height of about 10 mm and a circumferential arc width of about 4.7 mm. In addition, if it were desired that each testing segment 82 would be covered by a 20 micron thick layer of reservoir fluid 255 from reservoirs 84 while cup 210 is spun, then the needed volume of reservoir fluid 255 for each reservoir 84 would only be about 0.94 microliters, for a total amount of 18.8 microliters of reservoir fluid 255 being needed.

Although twenty circumferential waveguides 228, (and their respective testing segments 82, reservoirs 84, and demarcations 86) are illustrated in FIG. 7, cup 210 may have any number of circumferential waveguides 228 (and their respective testing segments 82, reservoirs 84, and demarcations 86), or as few as two circumferential waveguides 228 (and their respective testing segments 82, reservoirs 84, and demarcations 86).

The cup 210's interior volume 268 may include a respective detection coating 250 on inner surface 232 of at least one of the circumferential waveguides 228. Detection coating 250 may comprise respective detection layers (e.g., detection layers 251*a*, 251*b*, and 251*c*). Detection coating 250 of any particular testing segment 82 may be different from detection coating 250 of one or more of the other testing segments 82.

Any particular testing segment 82 (with its respective detection coating 250, if any), may be used to help optically detect the presence, quantity, number, or at least one targeted distinguishing characteristic of any particular kind of analyte 52 in sample fluid 55 in any of the ways, and by using any of assays, that are discussed herein with respect to cup 10 and its detection coating 250.

Thus, by suitably selecting the testing segments 82 (along with their respective detection coatings 250, if any), it is apparent that cup 210 may desirably permit the simultaneous detection of the presence, quantity, number, or at least one targeted distinguishing characteristic of at least two different kinds of analytes 52; and it may desirably permit the simultaneous detection of two or more targeted distinguishing characteristics of the same kind of analyte 52.

Cup 210 may be used to detect the analytes 52 in sample fluid 55 in any suitable way. For example, if there is a single sample fluid 55 containing the analytes 52, then it may be added to all of the reservoirs 84 at the same time in any suitable way. On the other hand, if there are two, or more, different sample fluids 55, then each sample fluid 55 may be added to each of its one or more respective reservoirs 84 in any suitable way. For simplicity, in the following description of cup 210's use it will be assumed, by way of example, that there is only a single sample fluid 55.

After sample fluid 55 has been added to reservoirs 84, cup 210 may then be spun, to centrifugally-concentrate the analytes 52 towards and eventually onto inner surface 232 of a particular testing segment 82's respective circumferential waveguide 228 if that testing segment 82 does not have a detection coating 250, or towards and eventually onto inner surface 261 or 274 of the innermost detection layer 251a, 251b of a particular testing segment 82 if that testing segment 82 does have a detection coating 250. Sample fluid 55 may then be removed from the cup 210, after which any particular respective desired reservoir fluid 255 (e.g., a reagent), may be added to each respective reservoir 84, as may be needed to carry out any particular desired assay.

Cup 210 may then be spun again, to cause the respective reservoir fluid 255 in each reservoir 84 to flow onto its respective testing segment 82, and form a thin layer 251c on the respective circumferential waveguide 228's inner surface 232 (if the respective testing segment 82 has no detection coating 250), or on the respective inner surface 261 or 274 of the innermost detection layer 251a, 251b (if the testing segment 82 does have detection coating 250). Layer 251c may have an optically smooth inner surface 272. This part of the procedure for using cup 210 may be repeated at least once for each different reservoir fluid 255 that may be needed for any particular test or assay method being used.

Cup 210 may also be spun while any particular testing segment 82 is being subjected to evanescent or darkfield interrogation by interrogation light 24, 24a, 24b from at least one light source 26; and while at least one detector 60 is detecting signal light 58 that is emitted by outer surface 234 of that testing segment 82's circumferential waveguide 228 as a function of the presence, quantity, number, or at least one targeted distinguishing characteristic the analyte 52 that was detected by that testing segment 82.

Any suitable synchronizing or timing means may be provided (not illustrated for clarity), in order to synchronize the input of evanescent or darkfield interrogation light 24a, 24b from each light source 26 for any particular testing segment 82's waveguide 228; and the detection of signal light 58 that is emitted by outer surface 234 of that testing segment 82's waveguide 228.

It should be noted that at least one of the testing segments 82 may be inactive, in the sense that it is not used in detecting the presence, quantity, number, or any targeted distinguishing characteristic of any analytes 52 that may be present in sample fluid 55. This may be done in order to use any such inactive testing segment 82 for self-referencing ratiometric purposes with regard to the electrical output signals from detector 60, or for non-specific binding correction. Alternatively, one or more demarcations 86 may be used for such purposes.

By way of example, due to the high circumferential resolution of cup 210 that is provided by the drum style imaging approach described herein regarding detector 60, a cup 210 having a diameter of one to three cm should be able to accommodate twenty to forty testing segments 82.

By way of further example, cup 210's ability to simultaneously detect more than one kind of analyte 52, or more than one targeted distinguishing characteristic of any particular kind of analyte 52, makes cup 210 well suited for detecting the analytes 52 in dilute systems such as portable or recreational water, as well as in heterogeneous samples such as blood, milk, and pureed food products.

Figure 10:
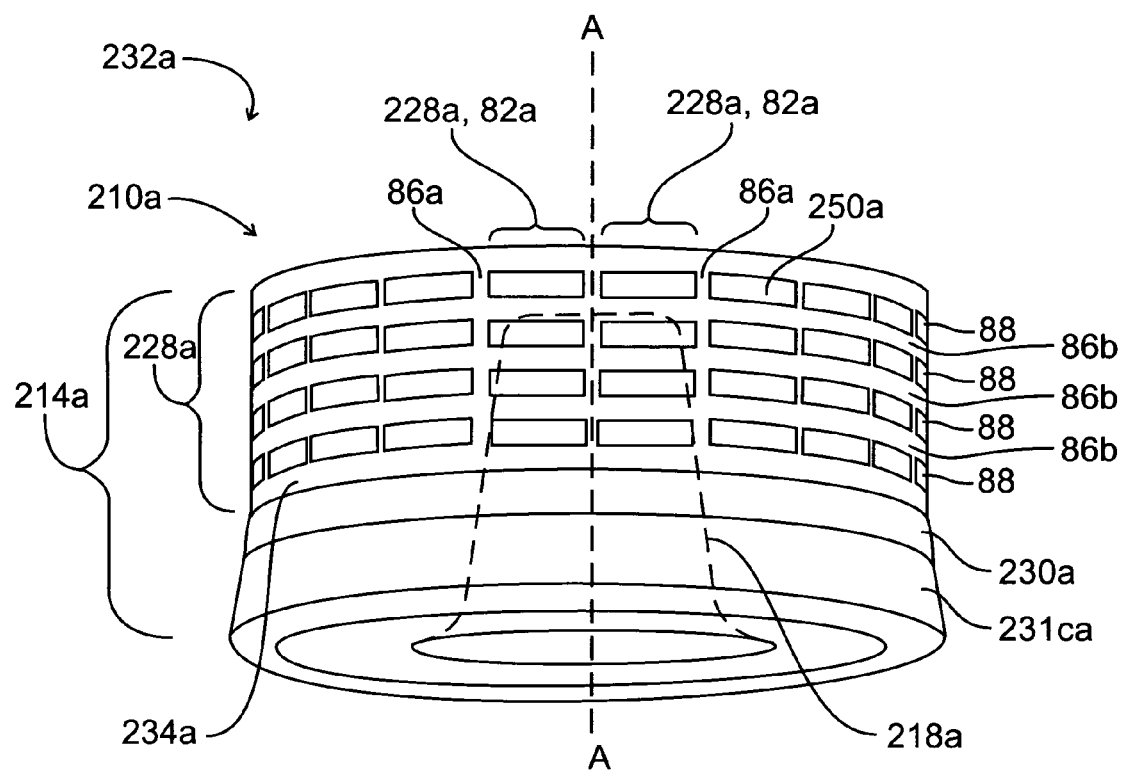
FIG. 10 is a diagrammatic perspective view of another embodiment of the optical assay cup of the present invention.

Axially Segmented Cup 210a (FIG. 10)

Turning now to FIG. 10, axially segmented cup 210a may be used with any of the assays described herein, and may have a cover 16 or a cover 316.

Cup 210a is the same as, or at least similar to, cups 10, 210, 310 and 410 in all respects, such as with respect to its respective mountings, locations, quantities (how many), sizes, shapes, designs, materials, compositions, constructions, manufactures, physical properties, dimensions, specifications, variations, operations, methods, and uses, except for those differences which will be made apparent by all of the disclosures herein. Accordingly, for clarity and simplicity, certain parts of cup 210a have been given the same reference numerals, with an "a" suffix, as the reference numerals used for the corresponding respective parts of cup 210.

As a conceptual starting point, cup 210a may be viewed as being made by first circumferentially segmenting waveguide 28 of cup 10's sidewall 14 into at least two circumferential waveguides 228a, in the manner that at least two circumferential waveguides 228 for cup 210 were conceptually made. Then inner surface 232a of at least one of the circumferential waveguides 228a may be axially segmented in a longitudinal direction that may be more or less parallel to cup 210a's A-axis, so that inner surface 232a comprises at least two axial testing segments 88.

Alternatively, the cup 210 may have only one circumferential waveguide 228a that extends entirely about the circumference of the cup 210, in the manner that waveguide 28 of cup 10 may extend entirely about the circumference of cup 10. Then inner surface 232a of that only one circumferential waveguide 228a may be axially segmented in a longitudinal direction that may be more or less parallel to cup 210a's A-axis, so that inner surface 232a comprises at least two axial testing segments 88.

In any event, axial testing segments 88 are the same as, or at least similar to, the circumferential testing segments 82, such as with respect to their respective mountings, locations, quantities (how many), sizes, shapes, designs, materials, compositions, constructions, manufactures, physical properties, dimensions, specifications, variations, operations, methods, and uses, except for those differences which will be made apparent by all of the disclosures herein.

Any particular axial testing segment 88 of any particular circumferential waveguide 228a may comprise a respective detection coating 250a on at least part of inner surface 232a of that particular circumferential waveguide 228a. Detection coating 250a may comprise respective detection layers (e.g., detection layers 251aa, 251ba, and 251ca). Detection coating 250a of any particular testing segment 82 may be different from detection coating 250a of one or more of the other testing segments 82. For clarity, detection coating 250a and detection layers 251aa, 251ba and 251ca are not illustrated in FIG. 10; but are analogous to cup 210's detection coating 250 and detection layers 251a, 251b and 251c, respectively.

Four axial testing segments 88 are illustrated in FIG. 10 for each waveguide 228a, by way of example. However, any particular circumferential waveguide 228a may not comprise the same number of axial testing segments 88 as one or more of the other circumferential waveguides 228a. Cup 210a may be provided with at least two axial testing segments 88 that extend partly, or wholly, around the circumference of cup 210a's sidewall 14.

Any particular pair of circumferentially adjacent axial testing segments 88 may be separated by any suitable axial demarcation 86a that extends more or less parallel to cup 10's A-axis, and any particular pair of axially adjacent axial testing segments 88 may be separated by any suitable circumferential demarcation 86b that extends more or less at a right angle with respect to cup 10's A-axis. Any particular demarcation 86a, 86b may be located on its respective circumferential waveguide 228a's inner or outer surfaces 232a, 234a. Any particular demarcation 86a, 86b may emit no, very little or an appreciable amount of marker indicating light, and may provide that function in any suitable way, such as by comprising a particular surface characteristic, such as, for example, grooves that scatter interrogation light 24a, 24b, or a coating that prevents the passage of an appreciable amount of signal light 58. Any particular demarcation 86a, 86b may be interrogated in any suitable way with any suitable marker interrogation light, which may or may not comprise waveguide interrogation light 24, 24a, 24b.

Each axial testing segment 88 and each demarcation 86a, 86b may be of any suitable respective size, shape, volume, construction, materials, compositions and orientation; and may not be uniform in any particular direction with respect to their respective size, shape, circumferential arc width, volume, construction, materials, compositions and orientation. Any particular axial testing segment 88 and any particular demarcation 86a, 86b may be different in size, shape, volume, construction, materials, compositions, and orientation from one or more of the other axial testing segments 88 and demarcations 86a, 86b, respectively.

The cup 210a's interior volume 268a may include a respective detection coating 250a on inner surface 232a of at least one of the circumferential waveguides 228a. Detection coating 250a may comprise respective detection layers (e.g., detection layers 251aa, 251ba, and 251ca). Detection coating 250a of any particular axial testing segment 88 may be different from detection coating 250a of one or more of the other testing segments 88. For clarity, detection coating 250a and detection layers 251aa, 251ba and 251ca are not illustrated in FIG. 10; but are analogous to cup 210's detection coating 250 and detection layers 251a, 251b and 251c, respectively.

Some of the benefits of providing axial testing segments 88 may be, for example, to increase the number of kinds of analytes 52, or the number of targeted distinguishing characteristics of a particular kind of analyte 52, that may be simultaneously detected by the present invention.

Other benefits of providing axial testing segments 88 may be, for example, to increase redundancy and statistical certainty of the measurements performed by using cup 210a. For example, if all four axial testing segments 88 in a particular circumferential waveguide 228a are designed to emit signal light 58 as a function of the presence of a particular analyte 52 in sample fluid 55 in cup 210a, and if the user requires that all four of those axial testing segments 88 must emit signal light 58 before that particular analyte 52 will be considered present in sample fluid 55, then the statistical accuracy will have been improved. For example, if it is assumed that the false-positive error rate associated with one of the four axial testing segments 88 emitting signal light 58 is 2%, then the overall statistical error for the four axial testing segments 88 in any particular circumferential waveguide 228a will be about $8 \times 10^{-8}$.

In addition, if a particular circumferential waveguide 228a's axial testing segments 88 are separated by one or more demarcations 86a, 86b, then any suitable conventional background subtracting protocol may be employed globally to null errors and increase accuracy, such as if high resolution drum-style imaging of signal light 58 by detector 60 is performed as described herein.

Cup 310 and Cover 316 (FIGS. 13-16)

Turning now to FIGS. 13-16, cup 310 and cover 316 may be used with any of the assays described herein. Cup 310 may have a cover 16 in lieu of cover 316. Cup 310 and cover 316 are, respectively, the same as, or at least similar to, cups 10, 210, 210a, and 410 and cover 16 in all respects, such as with respect to their respective mountings, locations, quantities (how many), sizes, shapes, designs, materials, compositions, constructions, manufactures, physical properties, dimensions, specifications, variations, operations, methods, and uses, except for those differences which will be made apparent by all of the disclosures herein.

Accordingly, for clarity and simplicity, certain parts of cup 310 and cover 316 have been given the same reference numerals, with a "3" prefix, as the reference numerals used for the corresponding respective parts of assay apparatus 11, cup 10 and its cover 16.

Cup 310 may comprise a base 312, a drive shaft holder 318, and a light conveying sidewall 314. Cover 316 may comprise an inlet port 100, an outlet port 102, an inner flange 104, and an outer flange 106, each of which may be of any suitable size and shape. Optional inlet and outlet fittings 110, 112 may be provided, respectively, for inlet and outlet ports 100, 102. Inner flange 104 may define a cavity 108 sized to receive cup 310's drive shaft holder 318.

Cup 310 and cover 316 may be releasably or permanently assembled together in any suitable way, such as by use of a fastener 114, for example. A leak-proof seal between cup 310 and cover 316 may be provided in any suitable way, such as by use of an O-ring 317, for example.

Figure 15:
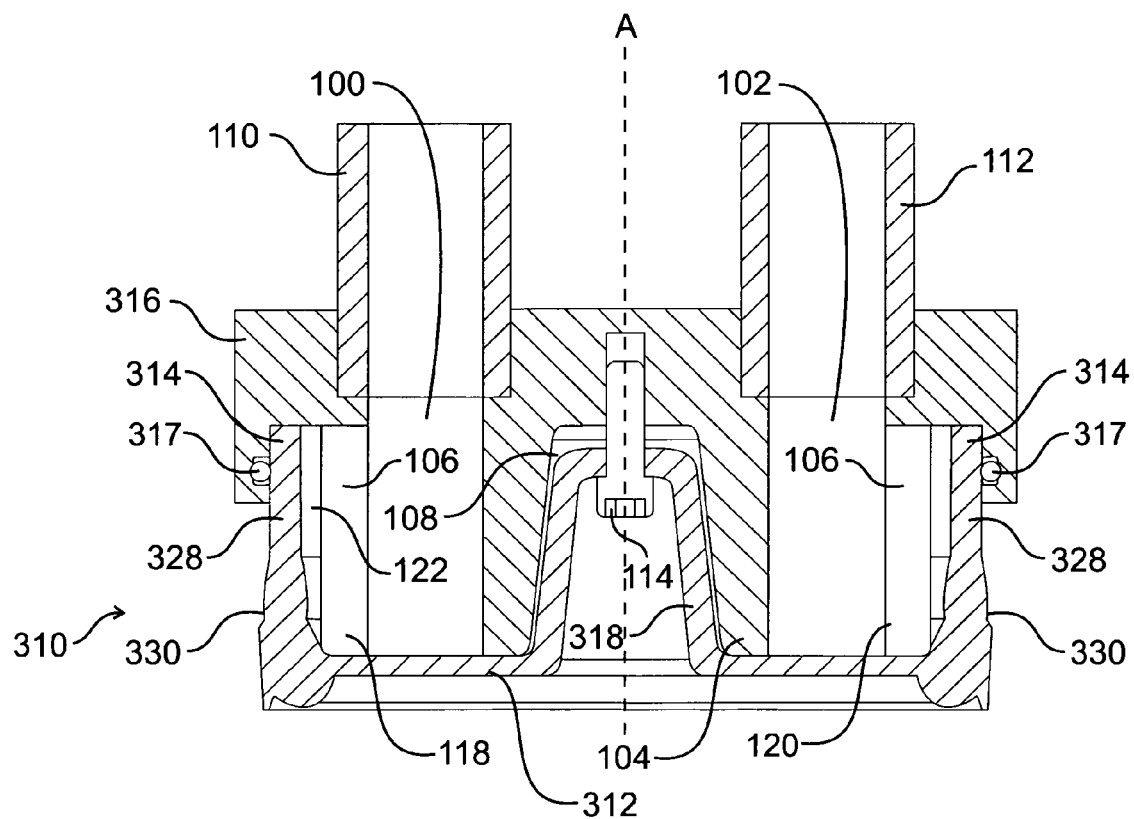
FIG. 15 is an assembled, cross-sectional view of the FIG. 13 embodiment, taken along line 15-15 of FIG. 13.

As best seen in FIG. 15, when cup 310 and cover 316 are assembled together, a leak-proof seal may be provided in any suitable way between cup 310's base 312 and the bottoms of cover 316's inner and outer flanges 104, 106, such as by use of flat contact surfaces therebetween, or by using any suitable sealing material (not illustrated, for clarity).

Figure 14:
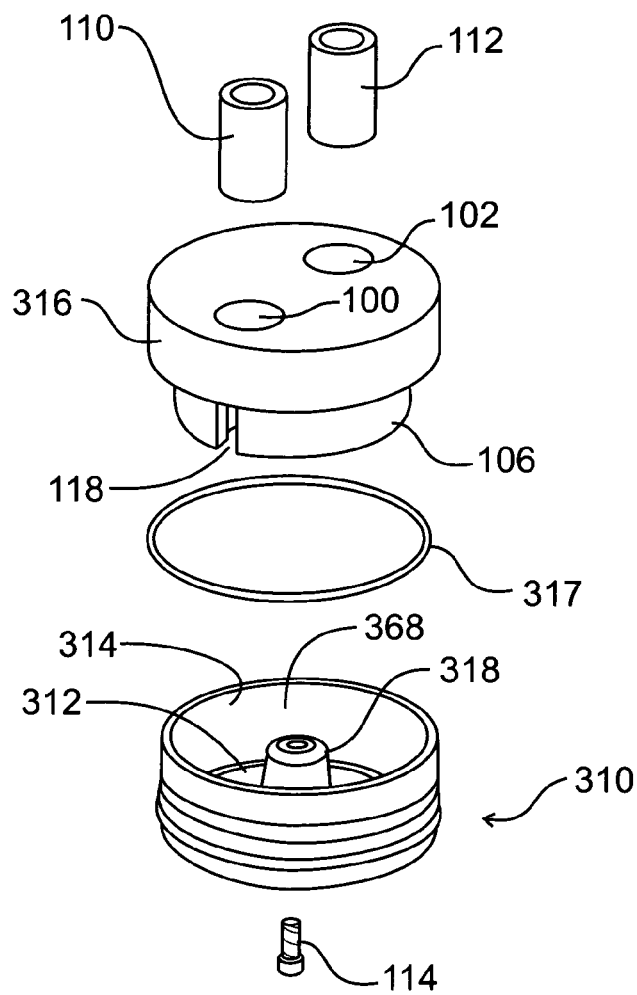
FIG. 14 is an exploded perspective view of the FIG. 13 embodiment.

As best seen in FIGS. 14 and 15, cup 310's sidewall 314 and cover 316's outer flange 106 may be sized with respect to each other so as to define therebetween an annular, circumferential flow chamber 122. Outer flange 106 may comprise an inlet slot 118 and an outlet slot 120 for flow chamber 122.

During use of the assembled cup 310 and cover 316, any suitable fluid (e.g., sample fluid 55, a reagent, a cleaning fluid, or water) may be introduced at any suitable time into cup 310 through cover 316's inlet fitting 110. The fluid may then travel sequentially through cup 310's inlet port 100; through flow chamber 122's inlet slot 118; and into flow chamber 122, where the fluid may then divide into two circumferential flows that travel through respective portions of flow chamber 122 in opposite directions from inlet slot 118 to outlet slot 120. From outlet slot 120 the fluid may then exit cup 310 through cover 316's outlet port 102 and outlet fitting 112.

By way of example, for a cup 310 having an inner radius of 1.5 cm, flow chamber 122 may have a radial width of about 1 mm, so that the fluid may flow through flow chamber 122 at a nominal rate of about 70 cc/min. Pressure drops of the fluid through inlet fitting 110 and inlet port 100 may be less than a few percent of the pressure drops across flow chamber 122 from its inlet slot 118 to its outlet slot 120, which may assure a moderately uniform flow of the fluid through flow chamber 122.

Any number of different fluids may be flowed through cup 310 and cover 316 in the manner indicated above, in any desired order, and in any desired quantities; such as while preparing cup 310's detection coating 350, or while performing any desired assay for a particular kind of analyte 52 with cup 310, for example.

Although cover 316 is illustrated as having only one inlet port 100 (with an optional inlet fitting 110), cover 316 may have more than one inlet port 100 (each of which may have an optional inlet fitting 110). Similarly, although cover 316 is illustrated as having only one outlet port 102 (with an optional outlet fitting 112), cover 316 may have more than one outlet port 102 (each of which may have an optional outlet fitting 112).

If cover 316 is provided with more than one inlet port 100 or outlet port 102, then its outer flange 106 may be provided with a respective inlet slot 118 for each such inlet port 100, and may be provided with a respective outlet slot 120 for each such outlet port 102.

Although cover 316's inlet and outlet ports 100, 102 (and outer flange 106's corresponding inlet and inlet slots 118, 120) are illustrated as being located about 180 degrees from each other about the periphery of cover 316, they may have any other suitable angular relationship with respect to each other; and may, or may not be spaced uniformly about the periphery of cover 316.

Figure 16:
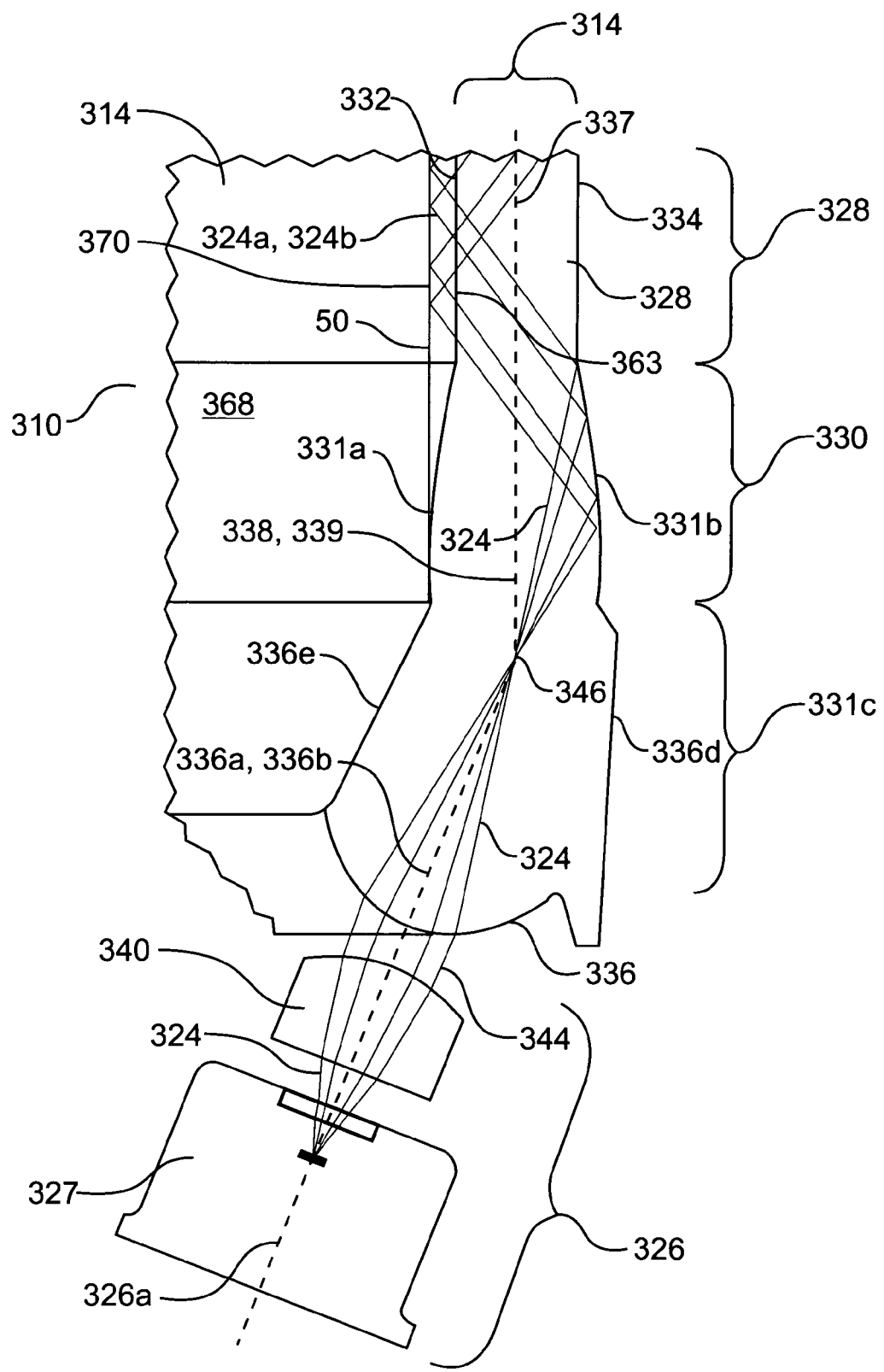
FIG. 16 is an enlarged side elevational view, partly in cross-section, of the light source and a portion of the sidewall of the FIG. 13 embodiment.

FIG. 16 illustrates an alternative way of creating either evanescent or darkfield interrogation light 324a or 324b for cup 310 from beam 344 of input interrogation light 324 from light source 326. The method for creating evanescent or darkfield interrogation light 324a, 324b would be apparent to a person of ordinary skill in the art, based all of the disclosures herein.

As seen in FIG. 16, cup 310's sidewall 314 may include a waveguide 328, a reflector 330, a lens support 331c, and an edge lens 336. Waveguide 328, reflector 330, and lens 336 may have respective optical surfaces of symmetry 337, 338, and 336b. Surfaces of symmetry 337 and 338 may coincide, as seen in FIG. 16, to form a common optical surface of symmetry 339. This is analogous to cup 10's surfaces of symmetry 37 and 38, which may coincide as seen in FIG. 4, to form common surface of symmetry 39.

Lens 336's optical surface of symmetry 336b and light source 326's optical axis 326a may not be parallel to cup 310's A-axis, but instead may be oriented at any suitable zero or non-zero angle relative to one another or relative to optical surface of symmetry 337, 338 or 339. For example, it may be preferred that light source 326's optical axis 326a be coincident with lens 336's optical surface of symmetry 336b (i.e., oriented at a zero angle relative to one another); because this usually provides the most effective energy transfer from light source 326's collimated beam 334 of interrogation light 324 to lens 336.

Lens 336 acts upon collimated beam 334 to create a bright, curved line segment (focal line 346 of lens 336 and reflector 330) on optical surface of symmetry 338. In this case, lens 336's optical surface of symmetry 336a and light source 326's optical axis 326a are oriented at a non-zero angle with respect to optical surface of symmetry 338. The focal line 346 lies at the intersection of optical surface of symmetry 336b with optical surface of symmetry 338, and is at a constant radius from cup 10's A-axis. Thus, the focal line 346 may act as a curvilinear, virtual line source of interrogation light 324. Interrogation light 324 thereafter expands from this virtual line source 346, is reflected from reflector 330's outer surface 331b, and enters waveguide 328. From that entry point rays of interrogation light 324 are reflected multiple times as they pass down waveguide 328.

The cup 310 and light source 326 may be designed to convert the interrogation light 324 into either evanescent or darkfield interrogation light 324a, 324b in any suitable way, such as in a manner similar to that previously discussed herein with respect to the FIGS. 1-5 embodiment of cup 10, light source 26 and interrogation light 24, 24a, 24b. There is no substantive difference in how light source 326, waveguide 328, lens 336, lens support 331c, and reflector 330 are designed or placed relative to each other as compared to the FIGS. 1-5 embodiment, since lens 336's internal focal line 346 is still on optical surface of symmetry 337, 338 or 339. As a result, design Equations 4-6 provided herein for cup 10 may be used for cup 310 and used for designing an outer surface 331b that will generate evanescent or darkfield interrogation light 324a, 324b with a distribution of reflected angles $\theta_{0i}$ (see FIG. 4). The fact that lens 336's optical surface of symmetry 336b and light source 326's optical axis 326a are oriented at a non-zero angle with respect to optical surface of symmetry 337, 338 or 339 will have no impact on the angle rays of evanescent or darkfield interrogation light 324a, 324b make with respect to waveguide 328's inner surface 332.

Several unique advantages may accrue from selecting a non-zero angular relationship between light source 326's optical axis 326a or lens 336's optical surface of symmetry 336b with respect to optical surfaces of symmetry 337, 338, or 339, or cup 310's A-axis. For example, it is apparent from FIGS. 14-16 that such a non-zero angular relationship may allow placement of the entire light source 326 within cup 310's radius, which may offer several advantages. For example, it may provide improved physical protection of light source 326 and lens 336 against damage and fouling of their optical surfaces. It may also reduce the overall radial extent of the combination of light source 326 and cup 310 for applications where lateral space is at a premium. It may also allow the design of a single, compact, light source 326 located on cup 310's A-axis that can simultaneously or sequentially inject collimated beams 344 of interrogation light 324 of the same or different wavelengths into selected circumferential segments of cup 310's reflector 330. This may allow the cup 310's interior volume 368 to be scanned more quickly and/or to be scanned at multiple wavelengths.

Another advantage of using a non-zero angular relationship between light source 326's optical axis 326a or lens 336's optical surface of symmetry 336b with respect to optical surfaces of symmetry 337, 338, or 338, or cup 310's A-axis is that it may also allow lens support 331c's outer surface 336d to be used as a robotic or human gripping area without compromising the optical performance of cup 310. This is because, as seen in FIG. 16, none of the excitation light 324 may impinge on outer surface 336d. Similar comments apply to the outer surface 31d of lens support 31c of cup 10 of FIG. 3.

A further advantage of using a non-zero angular relationship between light source 326's optical axis 326a or lens 336's optical surface of symmetry 336b with respect to optical surfaces of symmetry 337, 338, or 338, or cup 310's A-axis is that excitation light 324 from light source 326 does not impinge on lens support 331c's inner surface 336e or on reflector 330's inner surface 331a before entering waveguide 328. This prevents the generation of fluorescent signals from fluorescing materials or reagents that might be adsorbed onto inner surfaces 336e or 331a, and prevents the absorption of excitation light 324 by any light-absorbing debris that might be present on inner surfaces 336e, 331a.

Another advantage of using a non-zero angular relationship between light source 326's optical axis 326a or lens 336's optical surface of symmetry 336b with respect to optical surfaces of symmetry 337, 338, or 338, or cup 310's A-axis is that reflector 330's outer reflective surface 331b may be maintained more clean and consistent because sample debris cannot foul the reflective surface 331b.

Finally, a further advantage of using a non-zero angular relationship between light source 326's optical axis 326a or lens 336's optical surface of symmetry 336b with respect to optical surfaces of symmetry 337, 338, or 338, or cup 310's A-axis is that impingement of interrogation light 324 (e.g., evanescent or darkfield interrogation light 324a, 324b) from light source 326, on waveguide 328's inner surface 332 may be shaped in useful ways.

For example, as can be seen in FIG. 16, all of light source 326's interrogation light 324, 324a, 324b first impinges on waveguide 328's inner surface 332 over a certain axial distance. Because of this, the intensity of interrogation light 324, 324a, 324b impinging on waveguide 328's inner surface 332 over this axial distance is approximately twice what would be seen if a coaxial arrangement of light source 324, reflector 330 and waveguide 328 were used. Furthermore, interrogation light 324, 324a, 324b is alternately reflected at waveguide 328's inner surface 332 and outer surface 334 as it propagates in an axial direction down waveguide 328's length. As a result of these alternating reflections, a series of high intensity axial interrogation regions will be formed on waveguide 328's inner surface 332 by interrogation light 324, 324a, 324b. These high intensity axial interrogation regions may either overlap or be separated from one another, depending on such variables as the reflected angle $\theta_{Oi}$ (i.e., the angle a reflected ray of interrogation light 324, 324a, 324b from reflector 330's outer surface 331b makes with respect to reflector 330's optical surface of symmetry 338), and the thicknesses and compositions of waveguide 328 and detection layer 350 (e.g., detection layers 350a, 350b, 350c).

If the cup 310 is designed so that the high intensity axial interrogation regions overlap, then the interrogation of waveguide 328 and detection coating 350 by interrogation light 324, 324a, 324b may approximate a uniform condition. On the other hand, if cup 310 is designed so that the high intensity axial interrogation regions do not overlap, then the intervening non-interrogated axial regions may be used for reference purposes, since their output of signal light 58 should be very low. In addition, any such intervening non-interrogated axial regions are dark spaces that may advantageously reduce the levels of interrogation flare light injected into signal detector 60's optics by any interrogation light 324, 324a, 324b scattering from surface imperfections and debris of reflector 330, waveguide 328 and detection coating 350.

By way of example, a cup 310 capable of producing high intensity axial interrogation regions and non-interrogated axial regions for its waveguide 328 and detection coating 350 may be made from polystyrene, have a 3.6 cm inside diameter, and have a 1.4 mm thick waveguide 328. Light source 326 may have a laser diode light emitter 327 emitting at 635 nm, and a 1.8 mm diameter GRIN lens 340, sold by Nippon Sheet Glass of Somerset, N.J., that was cut and polished to a length of 1.95 mm. The angular orientation of lens support 336a's optical surface of symmetry 336b with respect to cup 310's A-axis and common optical surface of symmetry 339 may be 22 degrees. Collimated beam 344 of interrogation light 324 may have a circumferential width of about 0.45 mm and a radial width of about 1.3 mm. Annular lens 336 may have an internal focal length of about 3.5 mm. The reflected angle of interrogation light 324a, 324b at detection coating 350's curved inner surface 370 may be about 41.3 degrees relative to cup 310's A-axis (NA=0.91); and the size of the first high intensity axial interrogation region may be about 1.8 mm in length parallel to cup 310's A-axis, and 0.45 mm in width in a circumferential direction about cup 310.

It is to be understood that the darkfield interrogation methods described herein are not restricted to use in waveguides that are based on curved cylindrical walls, such as cup 10's waveguide 28 which may be part of cup 10's curved cylindrical wall 14, and have a circular cross-sectional profile with curved inner and outer surfaces 32, 34.

In view of all of the disclosures here, a person of ordinary skill in the art would understand that the darkfield interrogation methods described herein may be applied to waveguides having any suitable shape or cross-sectional profile such as, for example, a slab waveguide having at least substantially flat inner and outer surfaces which may be at least substantially parallel to each other, or a waveguide which is a solid cylinder having no inner surface, such as a fiber optic. Any such waveguide may be used in the darkfield interrogation methods described herein to form part of a composite sensing waveguide by applying to it in any suitable way any suitable detection coating (e.g., detection coating 50), which may comprise at least one fluid or non-fluid detection layer (e.g., detection layers 501, 50b, 50c). The transport of rays of darkfield interrogation light by such a composite sensing waveguide may be the same as, or at least similar to, the composite sensing waveguides that have already been described above in detail. It is understood that the foregoing forms of the invention were described and illustrated strictly by way of non-limiting example. As used herein, except in the claims, the words "and" and "or" are each defined to also carry the meaning of "and/or".

In addition, when the term "at least one of" is used in any of the claims, that term is defined to mean that any one, any more than one, or all, of the listed things or steps following that term is, or are, part of the claimed invention. For example, if a hypothetical claim recited "at least one of A, B, and C", then the claim is to be interpreted so that it may comprise (in addition to anything else recited in the claim), an A alone, a B alone, a C alone, both A and B, both A and C, both B and C, or all of A, B and C.

In view of all of the disclosures herein, these and further modifications, adaptations and, variations of the present invention will now be apparent to those of ordinary skill in the art to which it pertains, within the scope of the following claims.

The invention claimed is:

1. An optical assay apparatus for detecting an analyte in a sample fluid; wherein said assay apparatus comprises an optical assay cup;

wherein said cup comprises a sidewall and an interior volume;

wherein said interior volume is at least partially defined by said sidewall and is operable to receive said sample fluid;

wherein said sidewall comprises a waveguide having an input end, an inner surface and an outer surface; wherein said input end of said waveguide is operable to receive an input of waveguide interrogation light, and is operable to subject at least part of said interior volume to interrogation by use of at least part of said input of waveguide interrogation light; and wherein at least part of said outer surface of said waveguide is operable to emit an output of signal light as a function of said analyte;

wherein said output of signal light is at least primarily emitted through said at least of said outer surface of said waveguide; and wherein said output of signal light is not primarily emitted through said input end of said waveguide.

2. The assay apparatus of claim 1, wherein at least part of said input of waveguide interrogation light comprises an input of evanescent interrogation light; and wherein said interrogation of at least part of said interior volume comprises evanescent interrogation.

3. The assay apparatus of claim 1, wherein said at least part of said input of waveguide interrogation light comprises an input of darkfield interrogation light; and wherein said interrogation of at least part of said interior volume comprises darkfield interrogation.

4. The assay apparatus of claim 1, wherein said assay apparatus further comprises a spinning apparatus that is operable to spin said cup, to centrifugally-concentrate said analyte onto at least part of said inner surface of said waveguide.

5. The assay apparatus of claim 1, wherein said cup further comprises an innermost non-fluid detection layer on at least part of said inner surface of said waveguide; wherein said innermost non-fluid detection layer comprises an inner surface; and wherein said assay apparatus further comprises a spinning apparatus that is operable to spin said cup, to centrifugally-concentrate said analyte onto said inner surface of said innermost non-fluid detection layer.

6. The assay apparatus of claim 1, wherein said assay apparatus further comprises a spinning apparatus that is operable to spin said cup during said interrogation.

7. The assay apparatus of claim 1, wherein said assay apparatus further comprises a light source operable to produce said input of waveguide interrogation light, and a mounting apparatus operable to mount said light source and said cup with respect to each other.

8. The assay apparatus of claim 1, wherein said assay apparatus further comprises an optical detector operable to receive at least part of said output of signal light, and to produce an electrical output signal as a function of said signal light that is received by said optical detector.

9. The assay apparatus of claim 1, wherein said sidewall further comprises a reflector; wherein said reflector has a focal line; wherein said reflector is operable to receive an input of reflector interrogation light from said reflector focal line, and to produce in response thereto an output of reflector interrogation light; and wherein said input of waveguide interrogation light comprises at least part of said output of reflector interrogation light.

10. The assay apparatus of claim 9, wherein said assay apparatus further comprises a light source for said reflector; wherein said light source has an optical axis that is disposed so as to intersect with said reflector's focal line.

11. The assay apparatus of claim 1, wherein said interior volume of said cup comprises an analyte detection coating on at least part of said inner surface of said waveguide.

12. The assay apparatus of claim 11, wherein at least part of said analyte detection coating comprises a non-fluid detection layer.

13. The assay apparatus of claim 11, wherein at least part of said analyte detection coating comprises a fluid detection layer.

14. The assay apparatus of claim 13, wherein at least part of said fluid detection layer comprises at least part of said sample fluid.

15. The assay apparatus of claim 11, wherein at least part of said analyte detection coating comprises a non-fluid detection layer having an inner surface, and further comprises a fluid detection layer located on at least part of said inner surface of said non-fluid detection layer.

16. The assay apparatus of claim 11, wherein said cup further comprises a sensing waveguide comprising at least part of said analyte detection coating; wherein said sensing waveguide is operable to receive at least part of said input of waveguide interrogation light; wherein said sensing waveguide is operable to subject at least part of said analyte detection coating to interrogation by use of at least part of said input of waveguide interrogation light; and wherein at least part of said outer surface of said waveguide of said sidewall is operable to emit an output of said signal light as a function of said analyte.

17. The assay apparatus of claim 16, wherein said sensing waveguide further comprises at least part of said waveguide of said sidewall.

18. The assay apparatus of claim 16, wherein at least part of said analyte detection coating comprises a non-fluid detection layer.

19. The assay apparatus of claim 18, wherein said sensing waveguide further comprises at least part of said waveguide of said sidewall.

20. The assay apparatus of claim 16, wherein at least part of said analyte detection coating comprises a fluid detection layer.

21. The assay apparatus of claim 20, wherein said sensing waveguide further comprises at least part of said waveguide of said sidewall.

22. The assay apparatus of claim 20, wherein at least part of said fluid detection layer comprises at least part of said sample fluid.

23. The assay apparatus of claim 22, wherein said sensing waveguide further comprises at least part of said waveguide of said sidewall.

24. The assay apparatus of claim 16, wherein at least part of said analyte detection coating comprises a non-fluid detection layer having an inner surface, and further comprises a fluid detection layer located on at least part of said inner surface of said non-fluid detection layer.

25. The assay apparatus of claim 24, wherein said sensing waveguide further comprises at least part of said waveguide of said sidewall.

26. The assay apparatus of claim 1, wherein said waveguide comprises at least two circumferential waveguides; wherein each said circumferential waveguide comprises a circumferential arc width, an outer surface, and an inner surface that comprises a circumferential testing segment; and wherein at least part of each said outer surface of said circumferential waveguides is operable to emit an output of said signal light as a function of said analyte.

27. The assay apparatus of claim 26, wherein said interior volume of said cup comprises an analyte detection coating on at least part of each said circumferential testing segment.

28. The assay apparatus of claim 27, wherein said cup further comprises at least two sensing waveguides; wherein each said sensing waveguide comprises at least part of said analyte detection coating on a respective one of said circumferential testing segments; wherein each said sensing waveguide is operable to receive at least part of said input of waveguide interrogation light; and wherein each said sensing waveguide is operable to subject at least part of said analyte detection coating on said respective one of said circumferential testing segments to interrogation by use of at least part of said input of waveguide interrogation light.

29. The assay apparatus according to claim 28, wherein each said sensing waveguide further comprises at least part of said respective one of said circumferential waveguides.

30. The assay apparatus of claim 26 wherein there are at least two kinds of said analyte in said sample fluid; and wherein at least part said outer surface of each of said circumferential waveguides is operable to emit a respective output of said signal light as a function of a respective one of said kinds of said analyte.

31. The assay apparatus of claim 26, wherein said analyte comprises at least two targeted distinguishing characteristics; and wherein at least part of said outer surface of each of said circumferential waveguides is operable to emit a respective output of said signal light as a function of a respective one of said targeted distinguishing characteristics.

32. The assay apparatus of claim 26, wherein said cup further comprises at least one demarcation and at least one adjacent pair of said circumferential waveguides; and wherein each said demarcation is located between a respective said adjacent pair of said circumferential waveguides.

33. The assay apparatus of claim 32, wherein at least one of said at least one demarcation comprises a null reference zone.

34. The assay apparatus of claim 26, wherein said cup further comprises a base connected to said sidewall; wherein said base comprises at least two reservoirs; and wherein each said reservoir is operable to hold a respective reservoir fluid for at least a respective one of said circumferential testing segments.

35. The assay apparatus of claim 34, wherein said cup further comprises at least two demarcations; wherein at least two of said demarcations form at least one adjacent pair of said demarcations, and wherein a respective one of said reservoirs and a corresponding respective one of said circumferential testing segments are located between a respective said adjacent pair of said demarcations.

36. The assay apparatus of claim 35, wherein said assay apparatus further comprises a spinning apparatus that is operable to spin said cup; and wherein said respective said adjacent pair of said demarcations are operable to channel said reservoir fluid from said respective one of said reservoirs onto said corresponding respective one of said circumferential testing segments when said cup is spun by said spinning apparatus.

37. The assay apparatus of claim 1, wherein said inner surface of said waveguide comprises at least two axial testing segments; and wherein respective portions of said outer surface of said waveguide that correspond to said axial testing segments are operable to emit respective outputs of said signal light as a function of said analyte.

38. The assay apparatus of claim 1, wherein said waveguide comprises at least two circumferential waveguides; and wherein each said circumferential waveguide comprises a circumferential arc width, an outer surface, and an inner surface that comprises at least two axial testing segments; and wherein respective portions of said outer surfaces of said circumferential waveguides that correspond to said axial testing segments are operable to emit respective outputs of said signal light as a function of said analyte.

39. The assay apparatus of claim 38, wherein said interior volume of said cup comprises an analyte detection coating on at least part of each of said axial testing segments.

40. The assay apparatus of claim 39, wherein said cup further comprises at least two sensing waveguides; wherein each said sensing waveguide comprises at least part of said analyte detection coating on a respective one of said axial testing segments; wherein each said sensing waveguide is operable to receive at least part of said input of waveguide interrogation light; and wherein each said sensing waveguide is operable to subject at least part of said analyte detection coating on said respective one of said axial testing segments to interrogation by use of at least part of said input of waveguide interrogation light.

41. The assay apparatus according to claim 40, wherein each said sensing waveguide further comprises at least part of a respective one of said circumferential waveguides.

42. The assay apparatus of claim 38, wherein there are at least two kinds of said analyte in said sample fluid; and wherein each of said respective outputs of said signal light are emitted as a function of a respective one of said kinds of said analyte.

43. The assay apparatus of claim 38, wherein said analyte comprises at least two targeted distinguishing characteristics; and wherein each of said respective outputs of said signal light are emitted as a function of a respective one of said targeted distinguishing characteristics.

44. The assay apparatus of claim 38, wherein said cup further comprises at least one demarcation and at least one adjacent pair of said axial testing segments; and wherein each said demarcation is located between a respective said adjacent pair of said axial testing segments.

45. The assay apparatus of claim 44, wherein at least one of said at least one demarcation comprises a null reference zone.

46. The assay apparatus of claim 1, wherein said assay apparatus further comprises a cover for said cup; and a fluid-tight seal between said cover and said cup.

47. The assay apparatus of claim 46, wherein said cover comprises a cover inlet port, a cover outlet port, and an annular flange; wherein said annular flange comprises a flange inlet port and a flange outlet port;

wherein, when assembled together, said cover and said cup define a peripheral flow chamber between said annular flange and said sidewall of said cup; and wherein, when assembled together, said cover and said cup are operable to permit a fluid to flow sequentially into said cover through said cover inlet port, through said flange inlet port, through said peripheral flow chamber, through said flange outlet port and out through said cover outlet port.

48. The assay apparatus of claim 1, wherein said assay apparatus further comprises a heater operable to transfer heat into at least part of said cup, and a mounting apparatus operable to mount said heater and said cup with respect to each other.

49. The assay apparatus of claim 1, wherein said assay apparatus further comprises a cooler operable to remove heat from at least part of said cup, and a mounting apparatus operable to mount said cooler and said cup with respect to each other.

50. An optical assay apparatus for detecting an analyte in a sample fluid by luminescence detection; wherein said assay apparatus comprises an optical assay cup and a spinning apparatus that is operable to spin said cup during said luminescence detection;

wherein said cup comprises a sidewall and an interior volume;

wherein said sidewall comprises an outer surface;

wherein said interior volume is at least partially defined by said sidewall and is operable to receive said sample fluid and a luminescent indicator for said analyte; and wherein at least part of said outer surface of said sidewall is operable to emit an output of luminescent signal light as a function of said analyte during said luminescence detection.

51. A composite sensing waveguide for detecting an analyte in a sample fluid; wherein said composite sensing waveguide comprises a support waveguide having a surface, and an analyte detection coating on at least part of said surface of said support waveguide;

wherein at least part of said analyte detection coating is operable to be in contact with said sample fluid during use of said composite sensing waveguide;

wherein said composite sensing waveguide is operable to receive an input of waveguide interrogation light, is operable to subject at least part of said sample fluid to interrogation by use of at least part of said input of waveguide interrogation light, and is operable to emit an output of signal light as a function of said analyte; and wherein at least part of said input of waveguide interrogation light comprises an input of darkfield interrogation light; and wherein said interrogation comprises darkfield interrogation.

* * * * *

UNITED STATES PATENT AND TRADEMARK OFFICE
CERTIFICATE OF CORRECTION

PATENT NO.         : 7,651,869 B2                                          Page 1 of 1
APPLICATION NO. : 11/374934
DATED              : January 26, 2010
INVENTOR(S)        : Saaski et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 669 days.

Signed and Sealed this

Twenty-eighth Day of December, 2010

David J. Kappos
*Director of the United States Patent and Trademark Office*